United States Patent
Yadav et al.

(10) Patent No.: US 12,414,972 B2
(45) Date of Patent: Sep. 16, 2025

(54) HUMAN ORIGIN PROBIOTIC LACTOBACILLUS RHAMNOSUS HL-200 TO REDUCE LEAKY GUT BY METABOLIZING ETHANOLAMINE

(71) Applicant: University of South Florida, Tampa, FL (US)

(72) Inventors: Hariom Yadav, Tampa, FL (US); Shalini Jain, Tampa, FL (US); Sidharth Mishra, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 17/973,909

(22) Filed: Oct. 26, 2022

(65) Prior Publication Data
US 2023/0131140 A1    Apr. 27, 2023

Related U.S. Application Data

(60) Provisional application No. 63/263,017, filed on Oct. 26, 2021.

(51) Int. Cl.
*A61K 35/747* (2015.01)
*A61K 45/06* (2006.01)
*A61P 1/00* (2006.01)

(52) U.S. Cl.
CPC ............ *A61K 35/747* (2013.01); *A61K 45/06* (2013.01); *A61P 1/00* (2018.01)

(58) Field of Classification Search
None
See application file for complete search history.

(56) References Cited

U.S. PATENT DOCUMENTS

2005/0074440 A1* 4/2005 Lin ............... A61K 35/747
                                                         435/252.9
2018/0333442 A1* 11/2018 Owyang .............. C07K 14/32
(Continued)

FOREIGN PATENT DOCUMENTS

CN      12322554 A  *  2/2021  ............ C12N 1/205
KR    102297271 B1  *  9/2021  ............. C12N 1/20

OTHER PUBLICATIONS

Singh et al., Beneficial Microbes, 8(2): 243-255 (2017) (Year: 2017).*
(Continued)

*Primary Examiner* — David W Berke-Schlessel
(74) *Attorney, Agent, or Firm* — Meunier Carlin & Curfman LLC

(57) ABSTRACT

The present disclosure provides for a method of treating increased gut permeability, including administering a therapeutically effective amount of a human-derived probiotic to a patient in need thereof. Further provided herein is a method of increasing a patient's metabolism of ethanolamine, including administering a therapeutically effective amount of human derived probiotics to the patient in need thereof. Also provided herein is a pharmaceutical composition, including a first strain of *Lactobacillus* and a second probiotic strain. The present disclosure also provides for a pharmaceutical composition, including *Lactobacillus* and an antidiabetic drug. Additionally, provided herein is a pharmaceutical composition, including *Lactobacillus* and a weight management drug.

13 Claims, 66 Drawing Sheets

(56) References Cited

U.S. PATENT DOCUMENTS

2019/0037902 A1* 2/2019 Fischer ................ C12N 1/205
2020/0046781 A1* 2/2020 Friedland .............. A61P 25/16

OTHER PUBLICATIONS

Odijk et al., Lab Chip, 15:745-752 (2015) (Year: 2015).*
Agbu et al., "MicroRNA-mediated regulation of glucose and lipid metabolism," Author Manuscript, Nature Reviews Molecular Cell Biology, Jun. 2021, vol. 22, No. 6, pp. 425-438.
Ahmad et al., "Gut permeability and mucosal inflammation: bad, good or context dependent," Author Manuscript, Mucosal Immunology, Mar. 2017, vol. 10, Issue 2, pp. 307-317.
Ahmadi et al., "A human-origin probiotic cocktail ameliorates aging-related leaky gut and inflammation via modulating the microbiota/taurine/tight junction axis," JCI Insight, May 2020, vol. 5, No. 9, pp. 1-18.
Ahmadi et al., "Metformin Reduces Aging-Related Leaky Gut and Improves Cognitive Function by Beneficially Modulating Gut Microbiome/Goblet Cell/Mucin Axis," Journals of Gerontology: Biological Sciences, Jun. 2020, vol. 75, No. 7, pp. e9-e21.
Ahmadi et al., "Prebiotics from acorn and sago prevent high-fat diet-induced insulin resistance via microbiome-gut-brain axis modulation," Author Manuscript, Journal of Nutritional Biochemistry, May 2019, vol. 67, pp. 1-13.
Andre et al., "Metabolic Endotoxemia: A Potential Underlying Mechanism of the Relationship between Dietary Fat Intake and Risk for Cognitive Impairments in Humans?" Nutrients, Aug. 2019, vol. 11, No. 8, pp. 1-23.
Beaumont et al., "Gut microbiota derived metabolites contribute to intestinal barrier maturation at the suckling-to-weaning transition," Gut Microbes, Apr. 2020, vol. 11, No. 5, pp. 1268-1286.
Bettcher et al., "Peripheral and central immune system crosstalk in Alzheimer disease—a research prospectus," Nature Reviews Neurology, Nov. 2021, vol. 17, pp. 689-701.
Buford, Thomas W., "(Dis)Trust your gut: the gut microbiome in age-related inflammation, health, and disease," Microbiome, Jul. 2017, vol. 5, No. 80, pp. 1-11.
Cani et al., "Metabolic Endotoxemia Initiates Obesity and Insulin Resistance," Diabetes, Jul. 2007, vol. 56, No. 7, pp. 1761-1772.
Caporaso et al., "QIIME allows analysis of high-throughput community sequencing data," Author Manuscript, Nature Methods, May 2010, vol. 7, No. 5, pp. 335-336.
Chakraborty et al., "Therapeutic advances of miRNAs: A preclinical and clinical update," Journal of Advanced Research, Feb. 2021, vol. 28, pp. 127-138.
Czech, Michael P. "Insulin action and resistance in obesity and type 2 diabetes," Author Manuscript, Nature Medicine, Jul. 2017, vol. 23, No. 7, pp. 804-814.
Deboer et al., "Therapy Insight: use of melanocortin antagonists in the treatment of cachexia in chronic disease," Nature Clinical Practice Endocrinology & Metabolism, Aug. 2006, vol. 2, No. 8, pp. 459-466.
Feng et al., "Short-Chain Fatty Acids Manifest Stimulative and Protective Effects on Intestinal Barrier Function Through the Inhibition of NLRP3 Inflammasome and Autophagy," Cellular Physiology and Biochemistry, Aug. 2018, vol. 49, pp. 190-205.
Franceschi et al., "Inflammaging: a new immune-metabolic viewpoint for age-related diseases," Nature Reviews Endocrinology, Oct. 2018, vol. 14, No. 10, pp. 576-590.
Garton et al., "New Frontiers: ARID3a in SLE," Cells, Sep. 2019, vol. 8, No. 10, pp. 1-16.
Ghosh et al., "Regulation of Intestinal Barrier Function by Microbial Metabolites," Cellular and Molecular Gastroenterology and Hepatology, 2021, vol. 11, No. 5, pp. 1463-1482.
Gratton et al., "An optimized sample handling strategy for metabolic profiling of human feces," Analytical Chemistry, Apr. 2016, vol. 88, No. 9, pp. 4661-4668.
Hackl et al., "miR-17, miR-19b, miR-20a, and miR-106a are down-regulated in human aging," Aging Cell, Apr. 2010, vol. 9, No. 2, pp. 291-296.
Henning, Robert J., "Obesity and obesity-induced inflammatory disease contribute to atherosclerosis: a review of the pathophysiology and treatment of obesity," American Journal of Cardiovascular Disease, Aug. 2021, vol. 11, No. 4, pp. 504-529.
Huang et al., "MicroRNA-101 attenuates pulmonary fibrosis by inhibiting fibroblast proliferation and activation," Journal of Biological Chemistry, Oct. 2017, vol. 292, No. 40, pp. 16420-16439.
Kennedy et al., "Geroscience: Linking Aging to Chronic Disease," Cell, Nov. 2014, vol. 159, No. 4, pp. 709-713.
Kuczynski et al., "Experimental and analytical tools for studying the human microbiome," Author Manuscript, Nature Reviews Genetics, Dec. 2011, vol. 13, No. 1, pp. 47-58.
Kumari et al., "Health-promoting role of dietary bioactive compounds through epigenetic modulations: a novel prophylactic and therapeutic approach," Critical Reviews in Food Science and Nutrition, Oct. 2020, vol. 62, Issue 3, pp. 1-21.
Ley et al., "Human gut microbes associated with obesity," Nature, Dec. 2006, vol. 444, pp. 1022-1023.
Li et al., "The immunological and metabolic landscape in primary and metastatic liver cancer," Nature Reviews Cancer, Jul. 2021, vol. 21, pp. 541-557.
Li et al., "The roles of the gut microbiota-miRNA interaction in the host pathophysiology," Molecular Medicine, Nov. 2020, vol. 26, No. 101, pp. 1-9.
Li et al., "Zonulin Regulates Intestinal Permeability and Facilitates Enteric Bacteria Permeation in Coronary Artery Disease," Science Reports, Jun. 2016, vol. 6, No. 29142, pp. 1-10.
Lippi et al., "MicroRNA-101 Regulates Multiple Developmental Programs to Constrain Excitation in Adult Neural Networks," Neuron, Dec. 2016, vol. 92, No. 6, pp. 1337-1351.
Liu et al., "The Host Shapes the Gut Microbiota via Fecal MicroRNA," Cell Host & Microbe, Jan. 2016, vol. 19, pp. 32-43.
Mathewson et al., "Gut microbiome derived metabolites modulate intestinal epithelial cell damage and mitigate Graft-versus-Host Disease," Author Manuscript, Nature Immunology, May 2016, vol. 17, No. 5, pp. 505-513.
Mishra et al., "Probiotics and Prebiotics for the Amelioration of Type 1 Diabetes: Present and Future Perspectives," Microorganisms, Mar. 2019, vol. 7, No. 67, pp. 1-26.
Monlun et al., "Chronic Low Grade Inflammation in Type 2 Diabetes—Activation of the Inflammasomes by Circulating Metabolites," Diabetes, Jul. 2018, vol. 67, Supp. 1, pp. 1726-P.
Nagpal et al., "Human-origin probiotic cocktail increases short-chain fatty acid production via modulation of mice and human gut microbiome," Scientific Reports, Aug. 2018, vol. 8, No. 12649, pp. 1-15.
Nagpal et al., "Obesity-Linked Gut Microbiome Dysbiosis Associated with Derangements in Gut Permeability and Intestinal Cellular Homeostasis Independent of Diet," Journal of Diabetes Research, Sep. 2018, vol. 2018, Article ID 3462092, pp. 1-9.
Nagpal et al., "Unique Gut Microbiome Signatures Depict Diet-Versus Genetically Induced Obesity in Mice," International Journal of Molecular Sciences, May 2020, vol. 21, No. 3434, pp. 1-17.
Navas-Molina et al., "Advancing our understanding of the human microbiome using QIIME," Author Manuscript, Methods in Enzymology, 2013, vol. 531, pp. 371-444.
Odenwald et al., "The intestinal epithelial barrier: a therapeutic target?" Author Manuscript, Nature Reviews Gastroenterology & Hepatology, Jan. 2017, vol. 14, No. 1, pp. 9-21.
Ondee et al., "Lactobacillus acidophilus LA5 improves saturated fat-induced obesity mouse model through the enhanced intestinal Akkermansia muciniphila," Scientific Reports, Mar. 2021, vol. 11, No. 6367, pp. 1-16.
Patel et al., "Ethanolamine and Phosphatidylethanolamine: Partners in Health and Disease," Oxidative Medicine and Cellular Longevity, Jul. 2017, vol. 2017, Article ID 4829180, pp. 1-18.
Petrie et al., "Diabetes, Hypertension, and Cardiovascular Disease: Clinical Insights and Vascular Mechanisms," Canadian Journal of Cardiology, May 2018, vol. 34, Issue 5, pp. 575-584.

(56) References Cited

OTHER PUBLICATIONS

Roy et al., "How the immune system shapes atherosclerosis: roles of innate and adaptive immunity," Nature Reviews Immunology, Aug. 2021, vol. 22, pp. 251-265.
Scheithauer et al., "Gut Microbiota as a Trigger for Metabolic Inflammation in Obesity and Type 2 Diabetes," Frontiers in Immunology, Oct. 2020, vol. 11, No. 571731, pp. 1-29.
Singh et al., "Enhancement of the gut barrier integrity by a microbial metabolite through the Nrf2 pathway," Nature Communications, Jan. 2019, vol. 10, No. 89, pp. 1-18.
Sturgeon et al., "Zonulin transgenic mice show altered gut permeability and increased morbidity/mortality in the DSS colitis model," Author Manuscript, Annals of the New York Academy of Science, Jun. 2017, vol. 1397, Issue 1, pp. 130-142.
Thaiss et al., "Hyperglycemia drives intestinal barrier dysfunction and risk for enteric infection," Science, Mar. 2018, vol. 359, pp. 1376-1383.
Tilg et al., "The intestinal microbiota fuelling metabolic inflammation," Nature Reviews Immunology, Jan. 2020, vol. 20, pp. 40-54.
Turnbaugh et al., "An obesity-associated gut microbiome with increased capacity for energy harvest," Nature, Dec. 2006, vol. 444, pp. 1027-1031.
Ulluwishewa et al., "Regulation of Tight Junction Permeability by Intestinal Bacteria and Dietary Components," The Journal of Nutrition Critical Review, Mar. 2011, vol. 141, No. 5, pp. 769-776.
Wang et al., "Lipoteichoic acid from the cell wall of a heat killed Lactobacillus paracasei D3-5 ameliorates aging-related leaky gut, inflammation and improves physical and cognitive functions: from C. elegans to mice," Geroscience, Feb. 2020, vol. 42, No. 1, pp. 333-352.
Wang et al., "MiR-101: a potential therapeutic target of cancers," American Journal of Translational Research, Nov. 2018, vol. 10, No. 11, pp. 3310-3321.
Wilsker et al., "ARID Proteins: A Diverse Family of DNA Binding Proteins Implicated in the Control of Cell Growth, Differentiation, and Development," Cell Growth & Differentiation, Mar. 2002, vol. 13, No. 3, pp. 95-106.
Yadav et al., "Antidiabetic effect of probiotic dahi containing Lactobacillus acidophilus and Lactobacillus casei in high fructose fed rats," Nutrition, Jan. 2007, vol. 23, No. 1, pp. 62-68.
Yadav et al., "Beneficial Metabolic Effects of a Probiotic via Butyrate-induced GLP-1 Hormone Secretion," The Journal of Biological Chemistry, Aug. 2013, vol. 288, No. 35, pp. 25088-25097.
Yadav et al., "Gut Microbiome Derived Metabolites to Regulate Energy Homeostasis: How Microbiome Talks to Host," Metabolomics, 2016, vol. 6, Issue 2, pp. 1-2.
Yadav et al., "Herbo-probiotic therapy in cardioprotection: a new way of nature to nurture," Nutrition, Jul.-Aug. 2013, vol. 29, Issues 7-8, pp. 1070-1071.
Yadav et al., "Protection from Obesity and Diabetes by Blockade of TGF-β/Smad3 signaling," Cell Metabolism, Jul. 2011, vol. 14, No. 1, pp. 67-79.
Zhang et al., "Demystifying the manipulation of host immunity, metabolism, and extraintestinal tumors by the gut microbiome," Signal Transduction and Targeted Therapy, Oct. 2019, vol. 4, No. 41, pp. 1-34.
Zhang et al., "Fecal microbiota transplantation alters the susceptibility of obese rats to type 2 diabetes mellitus," Aging (Albany NY), Sep. 2020, vol. 12, No. 17, pp. 17480-17502.
Zhu et al., "Inflammation, epigenetics, and metabolism converge to cell senescence and ageing: the regulation and Intervention," Signal Transduction and Targeted Therapy, Jun. 2021, vol. 6, No. 245, pp. 1-29.

\* cited by examiner

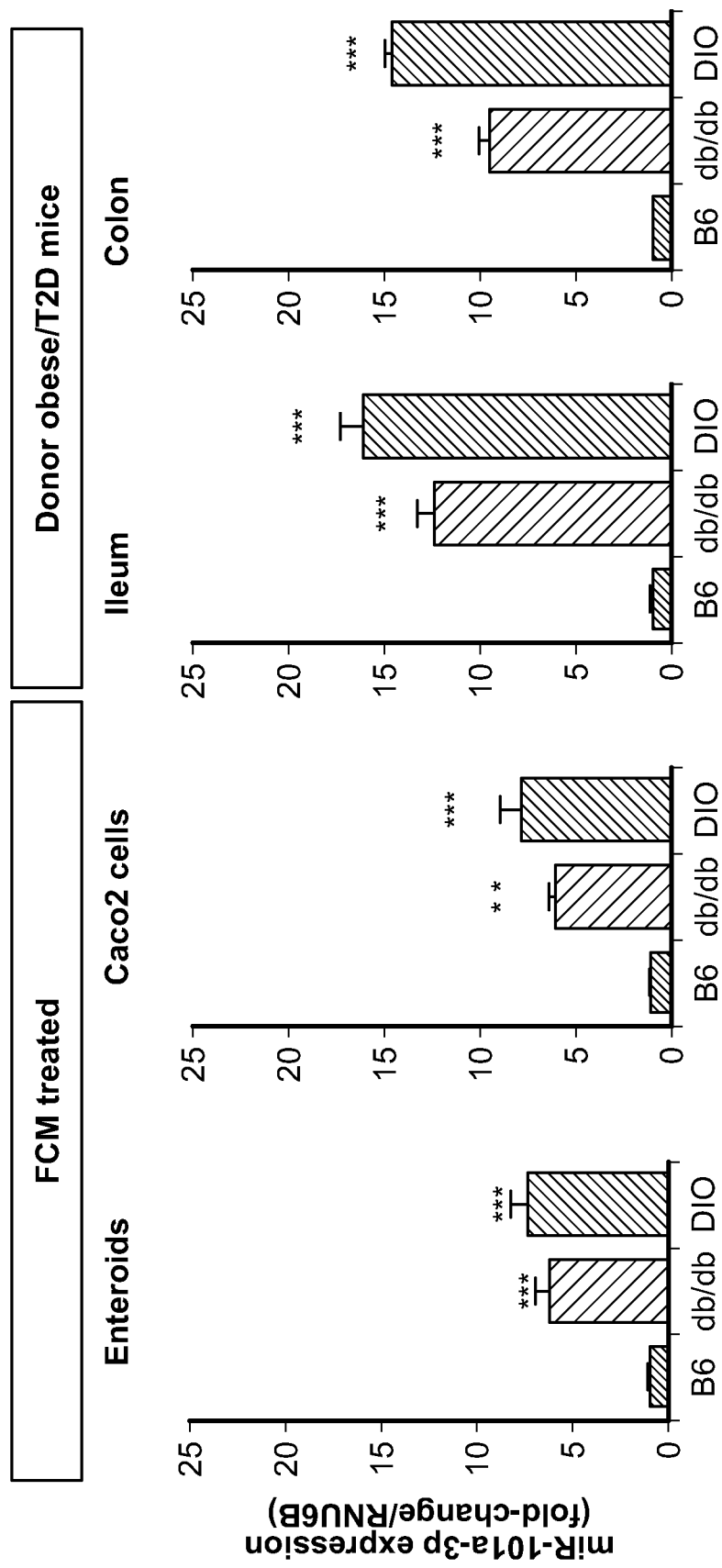

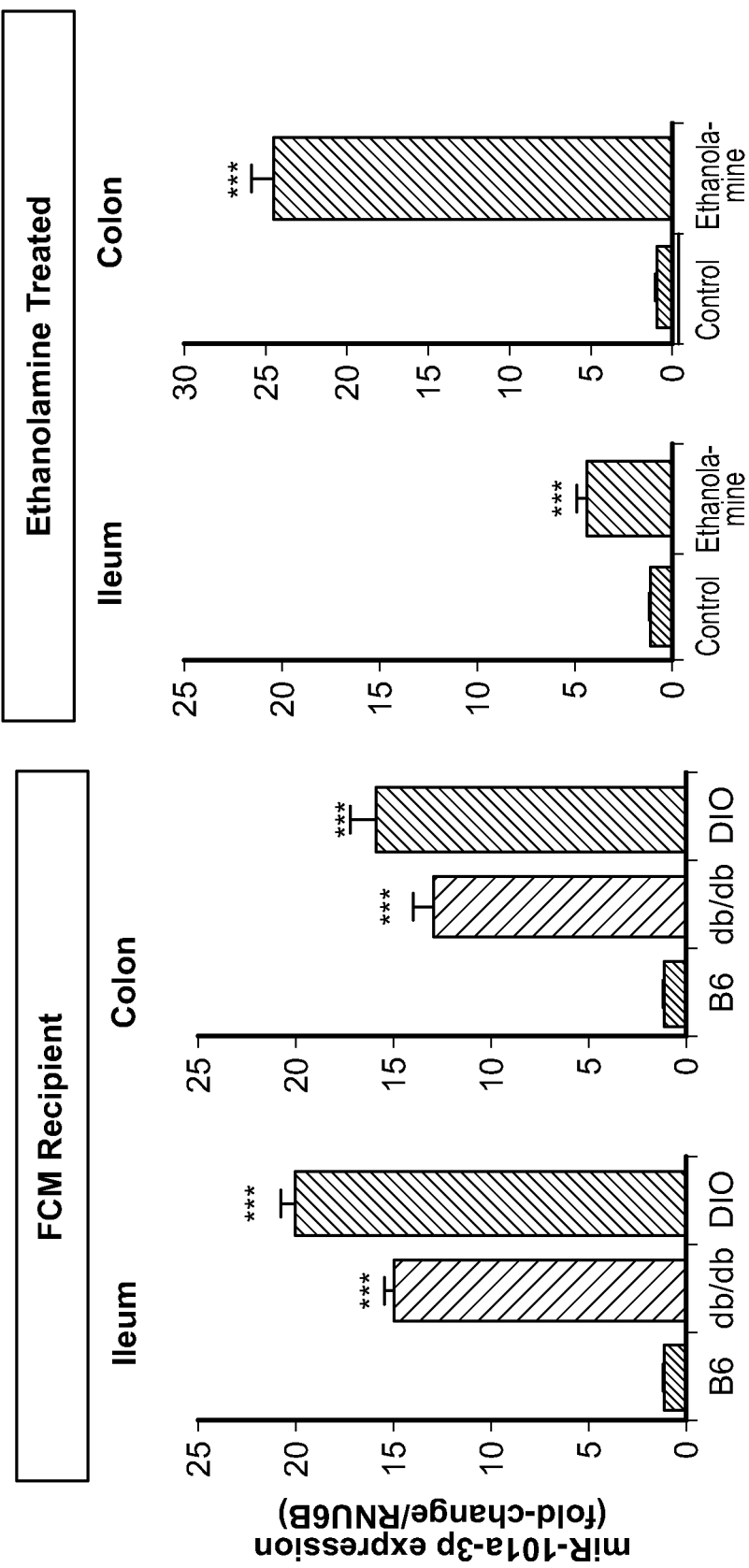

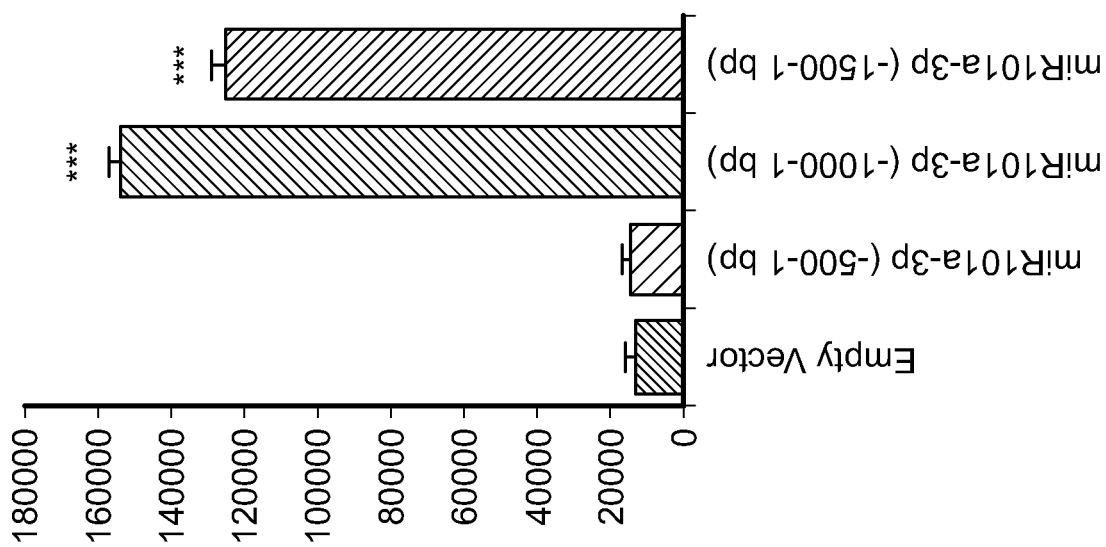
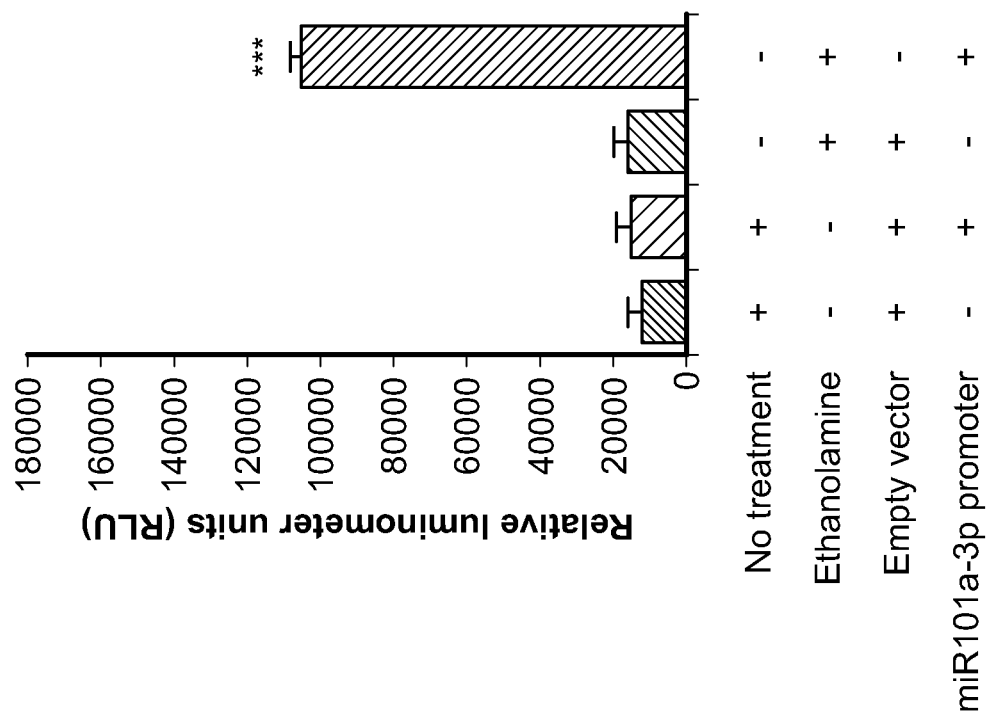
FIG. 5A
FIG. 5B

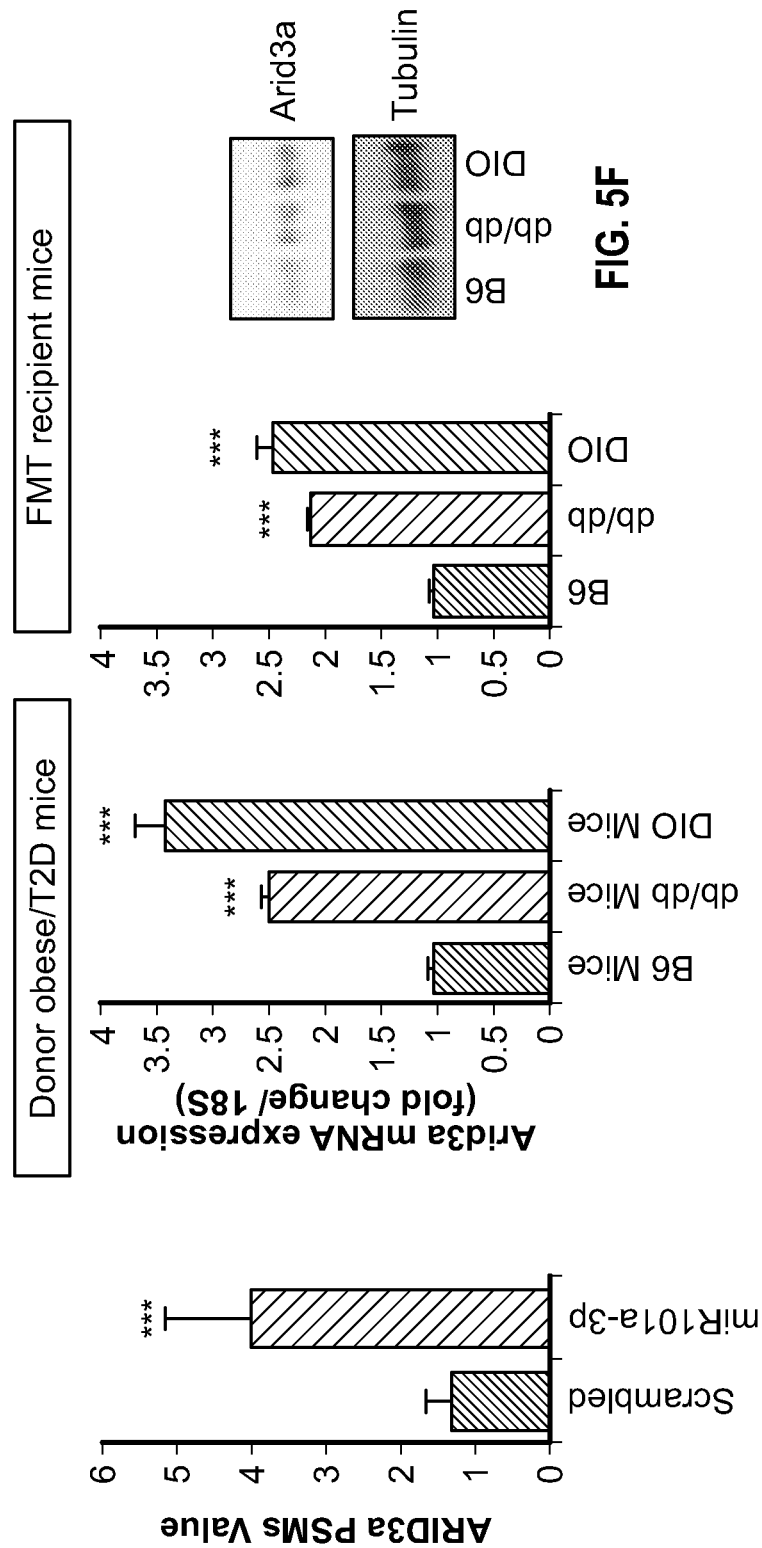

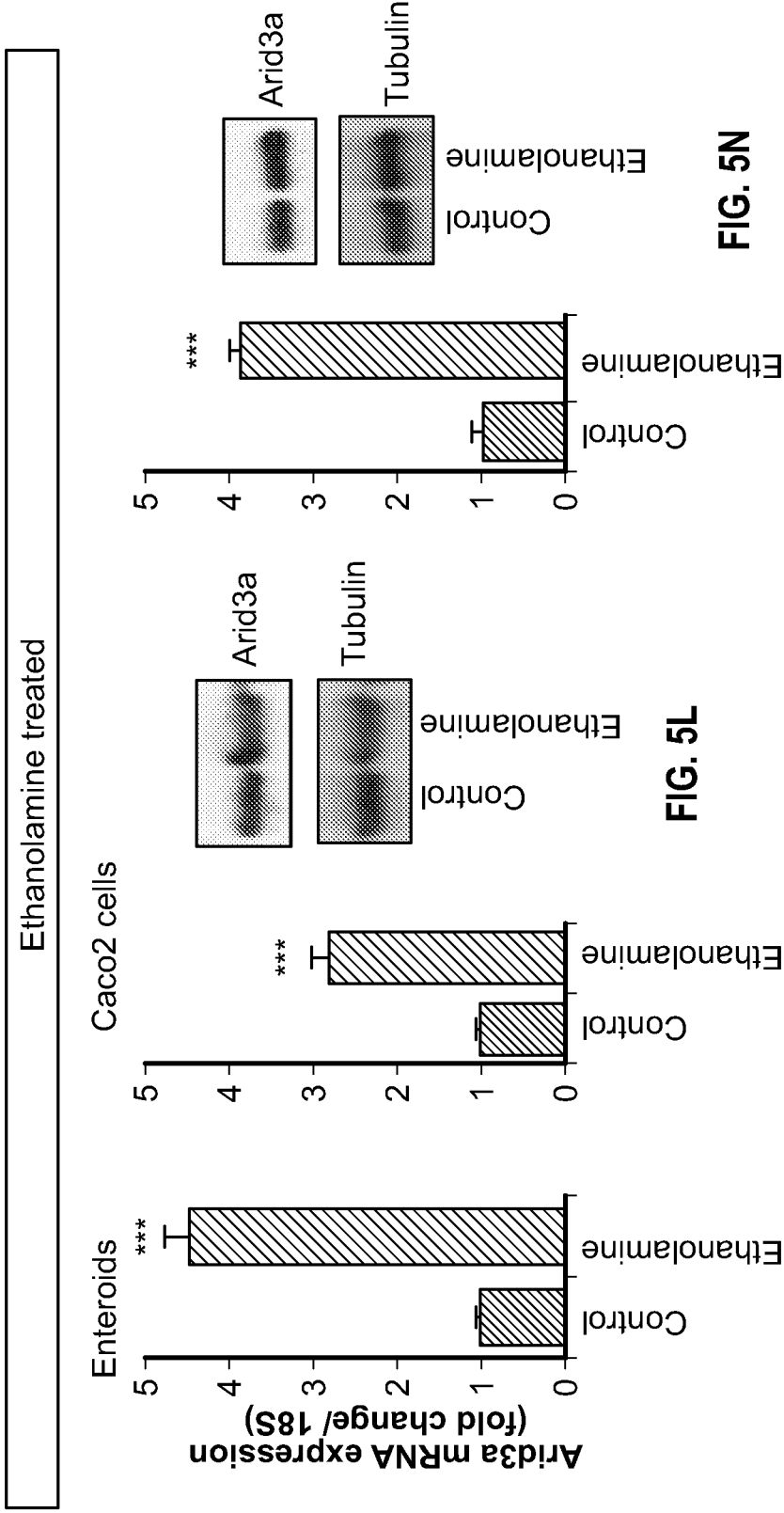

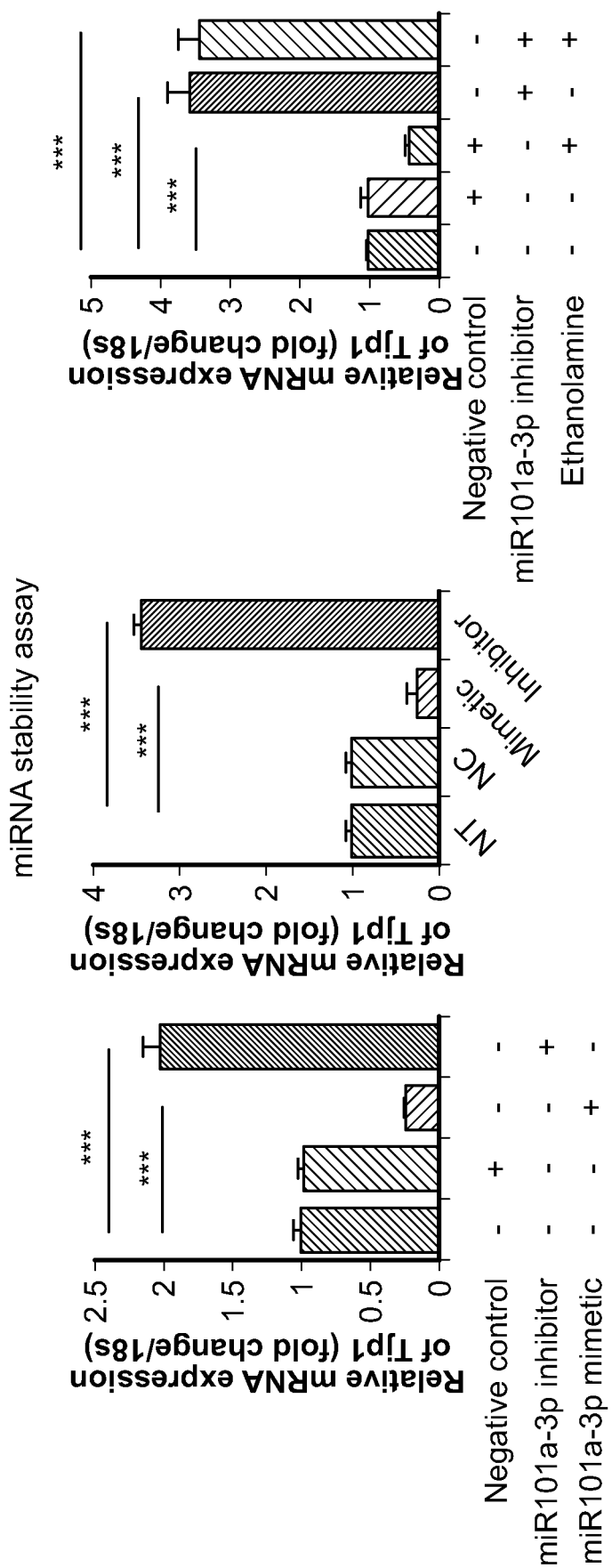

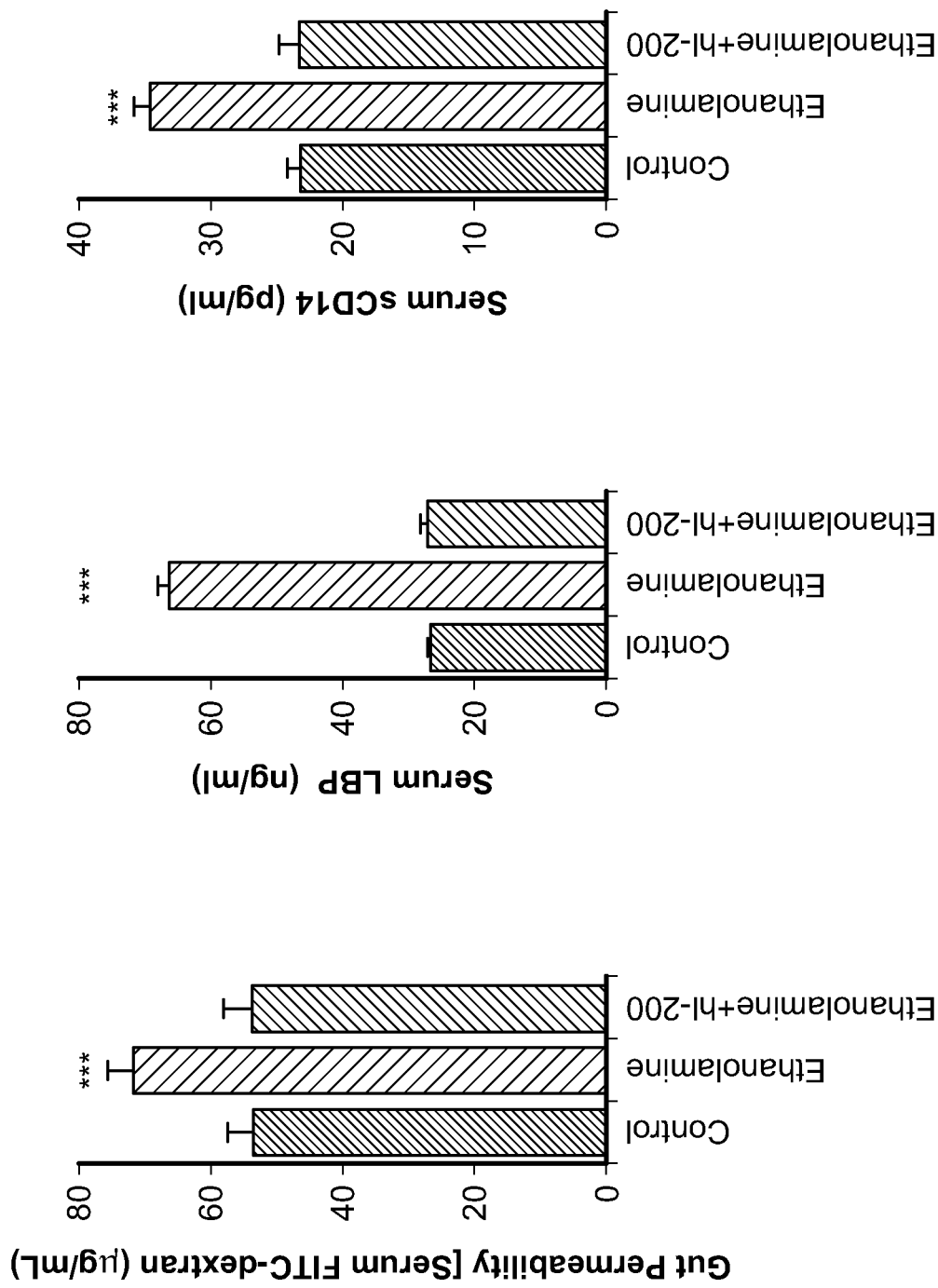

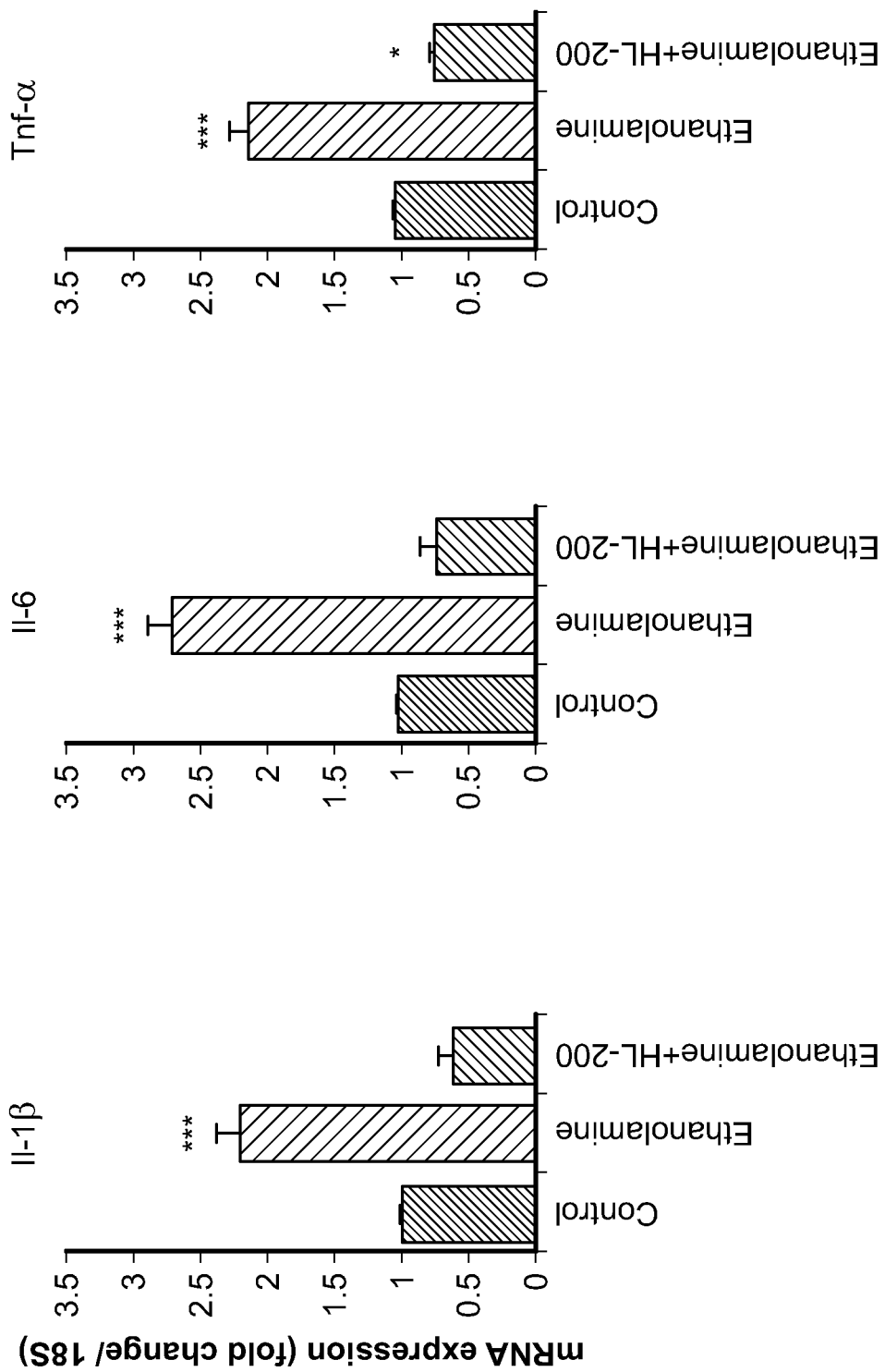

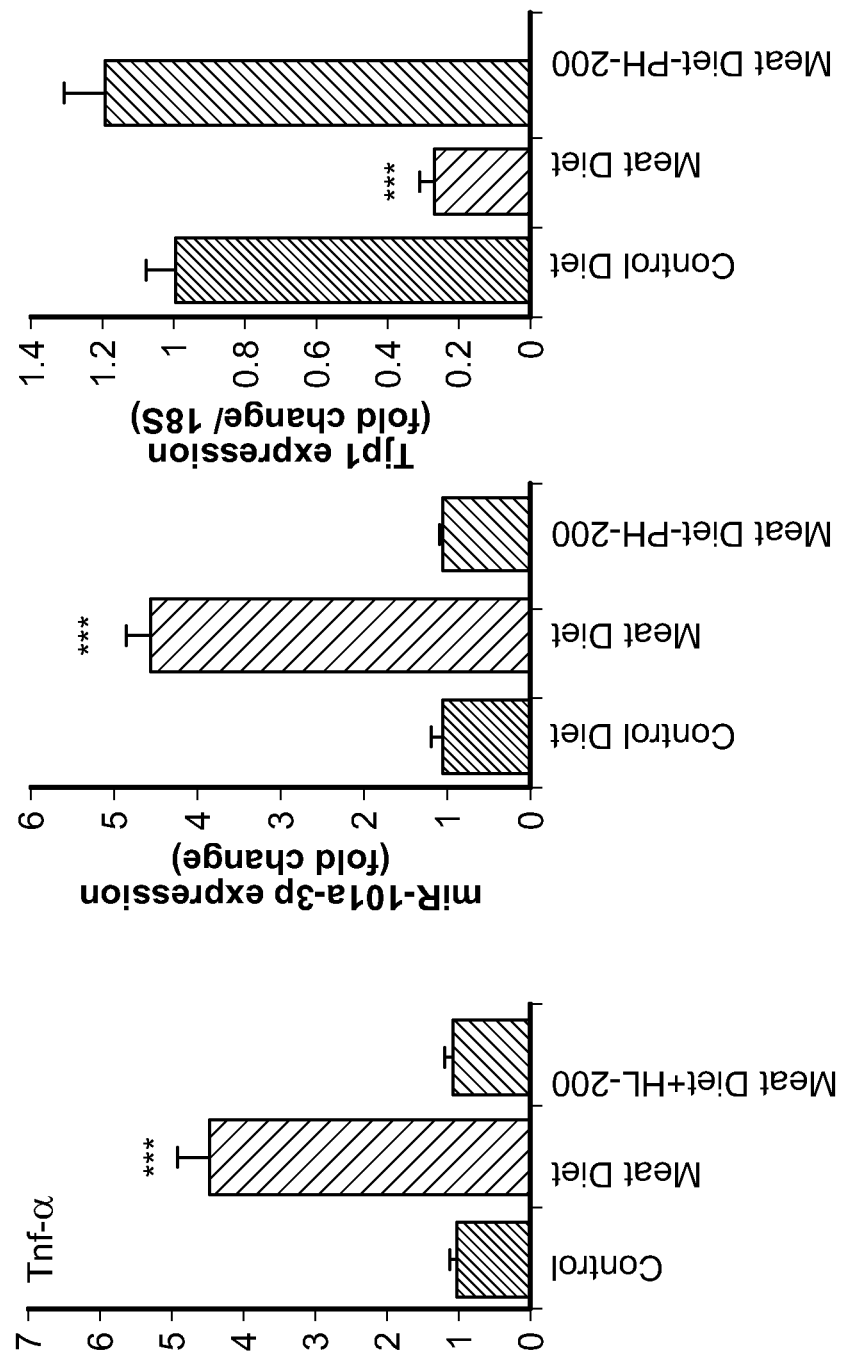

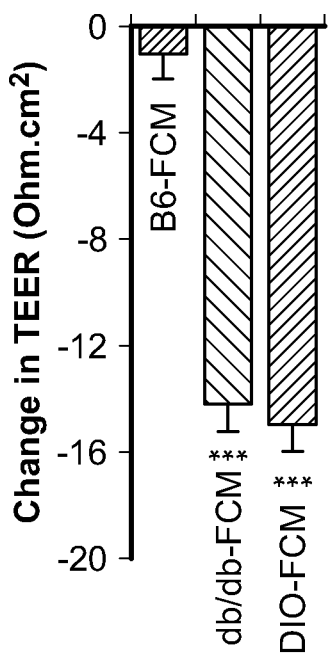
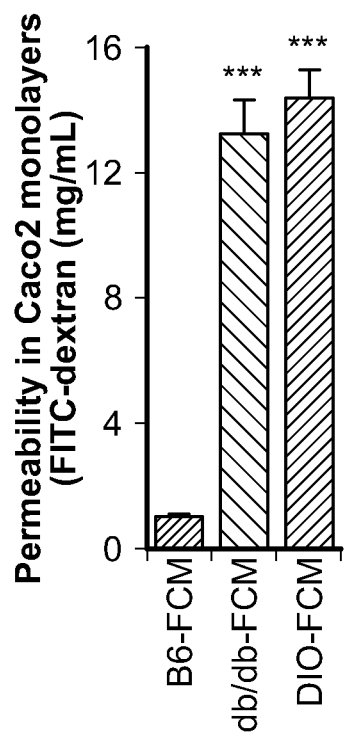
FIG. 10A  FIG. 10B
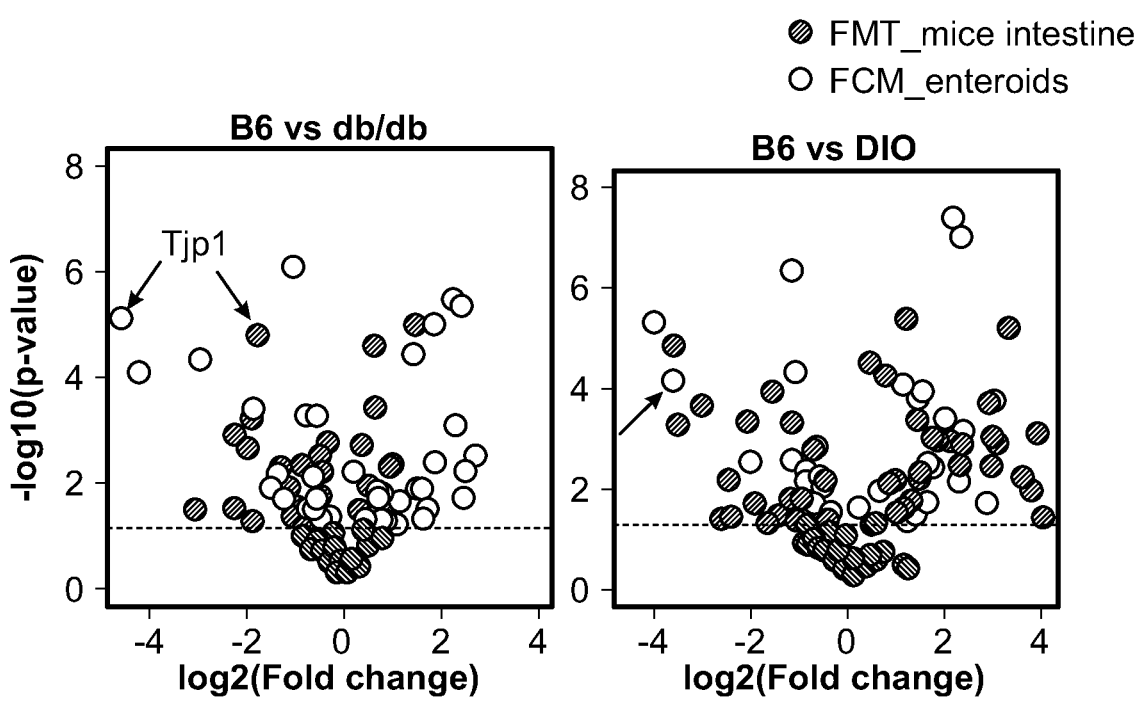
FIG. 10C

BIM of human obese subjects

| Measures | Normal weight | Obese |
|---|---|---|
| Participants (n) | 10 | 10 |
| Age (years) | 31.8±10.5 | 57.3±7.2 |
| Gender | | |
| Female | 4 | 8 |
| Male | 6 | 2 |
| Body mass index (kg/m²) | 22.8±2.1 | 36.29±4.7 |
| Values are presented as mean ± standard deviation. | | |
| Body mass index was calculated using body weight in kg and height in meters. | | |

Scrambled miR101a.3p

| Description | Gene Name | Accession | Fold Change (peptide-to-spectrum matches [PSM] values) | | p-Value |
| --- | --- | --- | --- | --- | --- |
| | | | Scrambled | miR101a-3p | |
| Proline-, glutamic acid- and leucine-rich protein 1 | PELP1 | Q8IZL8 | 1 | 4 | 0.0506 |
| At-rich interactive domain-containing protein 3A | ARID3A | Q99856 | 1 | 3 | 0.0454 |
| WD repeat-containing protein 43 | WDR43 | Q15061 | 1 | 3 | 0.1870 |
| Nuclear pore meambrane glycoprotein 210 | NUP210 | Q8TEM1 | 1 | 2.285 | 0.0370 |
| Elongation factor 1-alpha 1 | EEF1A1 | P68104 | 1 | 1.674 | 0.0428 |

FIG. 16C oPOSSOM V3 Result

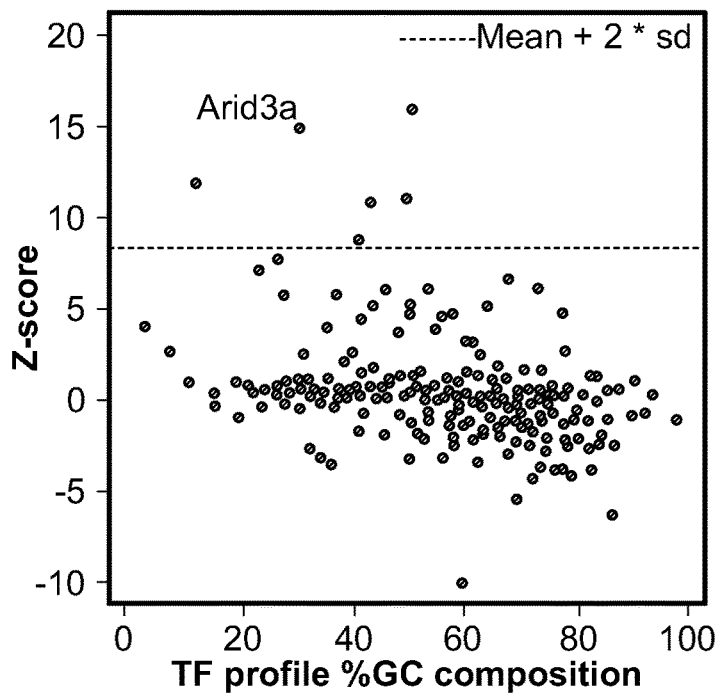

FIG. 17A

ConTra V3 Result

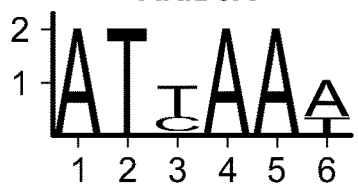

ARID3A

Type of analysis: visualization
Reference orgainsm: Human (homo sapiens)
Genomic position: chr1:65070204-65067704
Transcription factors: ARID3A
Homo-sapiens,M6147_1.02,M6147_1.02
Stringenecy: core = 0.95, similarity matrix = 0.85

> Promoter sequence from -1000 to -500 bp of miR101a-3p
> NC_000001.11:c65068704-65068204 Homo sapiens chromosome 1, GRCh38.p13 Primary Assembly

```
5`  ACTCACGAAAAACAAAAGTGAAAGT
    GCCTGAAGGGAACCCAGTAGTAAAC
    AAGAGTACAAAATTCTATATCTCAC
    CGGAAAACAGTGGCAGAGTTCCCAA
    ATATTTTTTTTTCAGCAACTGTGAA
    CTTCGGAAAGAATGAAATGTCTATC
    ACTCCCTTTGAATGTGAATAAGATC
    AGTGTAACACGAATCCACCTTGCTC
    TATGCAACTGTCTTCTGAAACAATC
    CTCTGACCCTGAACACCACTTATTT
    AAATAAGCGGTTCTTAAA*ATCAAT*CA
    ATCCGTAGTGAATGGTCCATCCCCA
    CAAAACCAATCCCCATTGAAGACCA
    CACCAAGTTGTGCCCCACTTTGGGA
    AAAGGGGGAAAGCGGGGGTAGAGAA
    AGAGGGGAAGGATTGGAACCAACAT
    TAGATTGTGCCTGGTGTTGCCACGC
    GGTTGTCATAAACAACGGCGTCGAA
    GCAAACTGTTTTAAAACTTAGAAAA
    TACGGCGGCCTTTAAACTCTATTAT  3`
```

FIG. 17B

| Targeted Bacterial Species | Cumulative cut operon gene Correlation with Bacterial Species | | | Relative Abundance (R.A.) | | | | p-Value | | | Fold Change | | | | NC abundance ranking |
|---|---|---|---|---|---|---|---|---|---|---|---|---|---|---|---|
| | NC | dbdb | DIO | Obese | NC | dbdb | DIO | Obese | dbdb | DIO | Obese | NC | dbdb | DIO | Obese | |
| Pedobacter kwangyangensis | -0.777 | 0.766 | 0.889 | 0.828 | 21.00 | 12.54 | 0.051 | 6.297 | 3.8E-08 | 1.77E-12 | 7.9E-11 | 1 | 0.597 | 0.002 | 0.299 | 1 |
| Akkermansia muciniphila | -0.826 | 0.812 | 0.869 | 0.841 | 18.90 | 0.185 | 2.157 | 1.171 | 3.22E-10 | 1.01E-09 | 5.54E-10 | 1 | 0.009 | 0.114 | 0.061 | 2 |
| Alkaliphilus crotonatoxidans | -0.525 | 0.706 | 0.852 | 0.779 | 5.564 | 1.331 | 0.043 | 0.687 | 1.11E-06 | 8.96E-08 | 2.9E-07 | 1 | 0.239 | 0.007 | 0.123 | 3 |
| Johnsonella ignava | -0.440 | 0.705 | 0.835 | 0.770 | 2.259 | 0.543 | 0.238 | 0.390 | 2.98E-06 | 6.25E-07 | 1.28E-06 | 1 | 0.240 | 0.105 | 0.172 | 4 |
| Bacteroides thetaiotaomicron | -0.477 | 0.206 | 0.804 | 0.505 | 2.093 | 1.734 | 0.004 | 0.869 | 0.073 23 | 1.46E-06 | 0.0001 41 | 1 | 0.828 | 0.001 | 0.415 | 5 |
| Clostridium termitidis | -0.530 | 0.318 | 0.853 | 0.585 | 0.492 | 0.425 | 0.006 | 0.215 | 0.034 849 | 5.76E-09 | 1.7E-06 | 1 | 0.864 | 0.013 | 0.438 | 6 |
| Clostridium frigoris | -0.523 | 0.646 | 0.835 | 0.741 | 0.397 | 0.177 | 0.014 | 0.096 | 3.13E-05 | 1.04E-07 | 1.09E-06 | 1 | 0.446 | 0.037 | 0.241 | 7 |
| Lachnospira pectinoschiza | -0.429 | 0.471 | 0.568 | 0.519 | 0.262 | 0.114 | 0.098 | 0.106 | 0.010 537 | 0.096 | 0.0078 24 | 1 | 0.436 | 0.375 | 0.406 | 8 |
| Coprobacillus cateniformis | -0.487 | 0.644 | 0.851 | 0.748 | 0.155 | 0.072 | 0.002 | 0.037 | 8.7E-06 | 8.63E-09 | 1.46E-07 | 1 | 0.465 | 0.015 | 0.240 | 9 |
| Luteolibacter algae | -0.526 | 0.769 | 0.885 | 0.827 | 0.142 | 0.002 | 0.019 | 0.010 | 1.32E-07 | 6.25E-07 | 2.51E-07 | 1 | 0.016 | 0.137 | 0.076 | 10 |
| Peptococcus niger | -0.507 | 0.616 | 0.778 | 0.697 | 0.065 | 0.021 | 0.014 | 0.017 | 8.11E-05 | 4.57E-05 | 3.15E-05 | 1 | 0.325 | 0.226 | 0.276 | 11 |
| Bifidobacterium choerinum | -0.433 | 0.444 | 0.096 | 0.270 | 0.039 | 0.016 | 0.035 | 0.025 | 0.097 1 | 0.026 | 0.033 | 1 | 0.409 | 0.892 | 0.650 | 12 |

FIG. 21

HUMAN ORIGIN PROBIOTIC LACTOBACILLUS RHAMNOSUS HL-200 TO REDUCE LEAKY GUT BY METABOLIZING ETHANOLAMINE

CROSS-REFERENCE TO RELATED APPLICATIONS

This application claims the benefit of priority to U.S. Provisional Application No. 63/263,017, filed on Oct. 26, 2021, the disclosure of which is expressly incorporated by reference herein in its entirety.

BACKGROUND

The prevalence of obesity and type-2 diabetes (T2D) and their complications are increasing, and no safe, inexpensive, and sustainable prevention and/or treatment is available. Low grade chronic inflammation is recognized as an important driver of obesity-mediated development of insulin resistance and T2D and their life-threatening complications such as cardiovascular disorders, neuropathy, nephropathy, retinopathy, dementia and cancer. (Li et al., 2021; DeBoer et al., 2006; Czech, 2017; Roy et al., 2021; Bettcher et al., 2021; Henning et al., 2021; Petrie et al., 2018). Evidence now exists for elevated gut permeability ("leaky gut") being an important source of systemic inflammation. (Cani et al., 2007; André et al., 2019). Indeed, leaky gut allows non-specific transfer of proinflammatory antigens, metabolites, and microbes from gut lumen to gut mucosa and blood, which, in turn, stimulates inflammatory response through local and systemic immune cells. (Buford, 2017; Zhang et al., 2019; Ahmad et al., 2017). However, the origin of leaky gut is not fully understood, and no prevention and treatments are available to reduce it. Microbiota is abnormal in the gut of patients with obesity/T2D. Fecal microbiota transplantation (FMT) studies have demonstrated that abnormal microbiota is causal to the risk of obesity and T2D. (Turnbaugh et al., 2006; Ley et al., 2006; Zhang et al., 2020). While leaky gut and inflammation co-occur with abnormal gut microbiota, (Tilg et al., 2020; Ulluwishewa et al., 2011), how an abnormal gut microbiota contributes to instigate leaky gut has so far remained largely unknown.

Gut permeability is maintained by the formation of abundant and healthy tight junction complex that clinch epithelial cells to sustain normal intestinal integrity. (Singh et al., 2019). Tight junction complexes are made from tight junction protein-1 (Tjp1) or zonulin-1 (Zo1), occludins, and claudins. Mice lacking Tjp1 show increased leaky gut and inflammation, (Sturgeon et al., 2017), thus indicating that Tjp1 expression helps maintain normal gut barrier functions and permeability. The expression of Tjp1 is significantly reduced in the obese/T2D gut and associates to leaky gut, inflammation, and abnormal gut microbiota (Li et al., 2016); however, the mechanisms involved in the decreased Tjp1 expression leading to leaky gut are not known. Evidence indicates that the metabolites produced by gut microbiota influences the expression of Tjp1 and thus gut permeability. (Singh et al., 2019; Mathewson et al., 2016). Anti-inflammatory microbial metabolites like short-chain fatty acids, indole derivatives, bile acid derivatives, and conjugated fatty acids promote expression of Tjp1 and reduce leaky gut (Feng et al., 2018; Beaumont et al., 2020; Ondee et al., 2021; Ghosh et al., 2021). There is poor knowledge of whether and how microbiota metabolites reduce Tjp1 expression and instigate leaky gut. The fine mechanisms which drive accumulation of these various metabolites are not known, nor are the mechanism(s) by which they impact Tjp1 expression and gut barrier functions understood.

In this context, it is known that epigenetic modifications in the intestinal cells are induced by host-microbes interactions and that they play a key role in maintaining intestinal barrier functions and thus host health. (Zhu et al., 2021; Kumari et al., 2020). In particular, host-produced micro (mi)-RNAs shape the gut microbiota while gut microbiota and its metabolites influence the expression of miRNAs in gut epithelial cells; this mechanism indicates continuous and bidirectional interactions between the gut microbiota and the host through miRNAs. (Liu et al., 2016; Li et al., 2020). The miRNAs are small endogenous non-coding, (Singh et al., 2019; Sturgeon et al., 2017; Li et al., 2016; Mathewson et al., 2016; Feng et al., 2018; Beaumont et al., 2020; Ondee et al., 2021; Ghosh et al., 2021), nucleotides RNAs that control gene expression by binding on the 3'-untranslated region (UTR) of the target mRNA due to base complementarity; thus, inducing translational repression, degradation, or both, of target mRNA. (Agbu et al., 2021). It is not understood, however, which and how microbial metabolites regulate those miRNAs involved in driving intestinal tight junctions and gut barrier function.

Chronic inflammation is a key risk factor for obesity and type 2 diabetes (T2D) and their complications. Ample evidence exists for chronic inflammation's role in abnormal gut microbiota composition and the increased gut permeability ("leaky gut") that can co-occur in obese/T2D gut; yet the fine mechanisms involved in this process have remained elusive. The causal role of the gut microbiota has been substantiated by fecal microbiota transplantation and through fecal conditioned media use. Moreover, the reduced capacity of microbiota of obese/T2D patients to metabolize ethanolamine results in ethanolamine accumulation, accounting for the leaky gut induction. Elevated ethanolamine-induced expression of microRNA-miR101a-3p by increasing ARID3a binding on the miR promoter; and miR101a-3p decreased the stability of tight junction protein-1 (Tjp1) mRNA, which in turn, weakens gut barrier functions and induces leaky gut.

SUMMARY

In accordance with the purposes of the disclosed compositions and methods, as embodied and broadly described herein, the disclosed subject matter, in one aspect, relates to compositions and methods of use thereof.

Thus, in one example, a method of treating increased gut permeability is provided, including administering a therapeutically effective amount of human derived probiotic to a patient in need thereof.

In a further example, a method of increasing a patient's metabolism of ethanolamine is provided, including administering a therapeutically effective amount of human derived probiotics to the patient in need thereof.

Additionally, a pharmaceutical composition is provided, including a first strain of *Lactobacillus* and a second probiotic strain.

In a further example, a pharmaceutical composition is provided, including *Lactobacillus* and an antidiabetic drug.

Further, a pharmaceutical composition is provided, including *Lactobacillus* and a weight management drug.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The accompanying figures, which are incorporated in and constitute a part of this specification, illustrate several aspects of the disclosure, and together with the description, serve to explain the principles of the disclosure.

FIG. 4C shows the real-time PCR analyses in enteroids that verified that miR101a-3p expression was significantly increased enteroids treated with FCMs of db/db and DIO mice compared to B6 controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4D shows the real-time PCR analyses in Caco2 cells that verified that miR101a-3p expression was significantly increased enteroids treated with FCMs of db/db and DIO mice compared to B6 controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4E shows that the expression of miR101a-3p was also significantly increased in the ileum of donor db/db compared to their controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4F shows that the expression of miR101a-3p was also significantly increased in the colon of donor DIO compared to their controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4G shows that the expression of miR101a-3p was also significantly increased in the ileum of FMT recipients compared to their controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4H The expression of miR101a-3p expression was also significantly increased in the colon of FMT recipients compared to their controls. Values presented are mean of n=6-8 mice in each group and error bars are standard error of means. PCA (a), and random forest analyses (b) show individual sample values. P values with *<0.05; <0.01 and *<0.001 are statistically significant.

FIG. 4I shows that ethanolamine treatment also significantly increased the expression of miR101a-3p expression in the ileum of mice. Values presented are mean of n=6-8 mice in each group and error bars are standard error of means. PCA (a), and random forest analyses (b) show individual sample values. P values with *<0.05; <0.01 and *<0.001 are statistically significant.

FIG. 4J shows that ethanolamine treatment also significantly increased the expression of miR101a-3p expression in the colon of mice. Values presented are mean of n=6-8 mice in each group and error bars are standard error of means. PCA (a), and random forest analyses (b) show individual sample values. P values with *<0.05; <0.01 and *<0.001 are statistically significant.

FIG. 5A shows that ethanolamine increased miR101a-3p expression by increasing its promoter activity through enhancing transcription factor ARID3a binding. Ethanolamine increased miR101a-3p promoter depicted by luciferase assay in Caco2 cells transfected with vector carrying miR101a-3p promoter (−1 to −2000 bp of transcript start site [TSS]) compared to empty vector transfected cells.

FIG. 5B shows that ethanolamine treatment significantly increased miR101a-3p promoter activity in the Caco2 cells transfected with vectors carrying −1 to −1000 bp and −1 to 1500 bp fragments, while no change was observed in cells transfected with vector carrying −1 to 500 bp and empty vector.

FIG. 5C shows that unbiased and untargeted ChiP—pull down analyses revealed that a transcription factor—ARID3a was highest protein pulled out with −500-1000 bp fragment compared to scrambled nucleotide DNA sequence.

FIG. 5D shows that expression of Arid3a mRNA was found significantly higher in the gut of donor db/db and DIO mice.

FIG. 5E shows that expression of Arid3a mRNA was found significantly higher in the gut of donor db/db and DIO mice as well as in FMT recipients.

FIG. 5F shows that expression of protein was found significantly higher in the gut of recipients.

FIG. 5J shows the effect of ethanolamine treatments in enteroids.

FIG. 5K shows the effect of ethanolamine treatments in Caco2 cells.

FIG. 5L shows that ethanolamine treatments significantly increased the expression of Arid3a in the enteroids.

FIG. 5M shows that ethanolamine treatments significantly increased the expression of Caco2 cells and mouse intestine compared to controls.

FIG. 5N shows that ethanolamine treatments significantly increased the expression of Caco2 cells and mouse intestine compared to controls.

FIG. 6D shows that miR101a-3p mimetic (Agomir) significantly reduced expression of Tjp1 mRNA while miR101a-3p inhibitor oligonucleotide (Antagomir) reversed it. Values presented are mean of n=2-3 repeated triplicate of Caco2 culture experiments in each group and error bars are standard error of means. P values with *<0.05; <0.01 and *<0.001 are statistically significant.

FIG. 6E shows that the miR101a-3p mimetic significantly reduced the stability of Tjp1 mRNA, while miR101a-3p inhibitor reversed it. Values presented are mean of n=2-3 repeated triplicate of Caco2 culture experiments in each group and error bars are standard error of means. P values with *<0.05; <0.01 and *<0.001 are statistically significant.

FIG. 6F shows that the ethanolamine effects to reduce Tjp1 mRNA expression were abolished by miR101a-3p inhibitor. Values presented are mean of n=2-3 repeated triplicate of Caco2 culture experiments in each group and error bars are standard error of means. P values with *<0.05; <0.01 and *<0.001 are statistically significant.

FIG. 7B shows that feeding of HL-200 to mice significantly reduced the ethanolamine mediated leaky gut (FITC-dextran) in the gut compared to controls.

FIG. 7C shows that feeding of HL-200 to mice significantly reduced the ethanolamine mediated leaky gut (LBP) in the gut compared to controls.

FIG. 7D shows that feeding of HL-200 to mice significantly reduced the ethanolamine mediated leaky gut (sCD-14) in the gut compared to controls.

FIG. 7E shows that feeding of HL-200 to mice significantly reduced inflammation (IL-1 $\beta$) in the gut compared to controls.

FIG. 7F shows that feeding of HL-200 to mice significantly reduced inflammation (IL-6) in the gut compared to controls.

FIG. 7G shows that feeding of HL-200 to mice significantly reduced inflammation (TNF-$\alpha$) in the gut compared to controls.

FIG. 7O shows that meat supplemented diet significantly increased inflammation (TNF-$\alpha$).

FIG. 7P shows that meat supplemented diet significantly increased expression of miR101a-3p.

FIG. 7Q shows that meat supplemented diet reduced expression of Tjp1 mRNA, while HL-200 probiotic therapy reverses these abnormalities.

FIG. 10A shows the change in TEER, FITC-dextran diffusion, and gene expression when treated with FCMs. Fecal conditioned media of db/db and DIO mice significantly decreased the TEER through Caco2 cells monolayers compared to B6 FCM control treated cells. Values presented are mean (n=6-8 mice per group) and average of enteroids and Caco2 culture experiments performed in triplicates and repeated 2-3 times. Error bars as standard error of means. P values with ***<0.001 are statistically significant.

FIG. 10B shows the change in TEER, FITC-dextran diffusion, and gene expression when treated with FCMs. Fecal conditioned media of db/db and DIO mice significantly increased FITC-dextran diffusion through Caco2 cells monolayers compared to B6 FCM control treated cells. Values presented are mean (n=6-8 mice per group) and average of enteroids and Caco2 culture experiments performed in triplicates and repeated 2-3 times. Error bars as standard error of means. P values with ***<0.001 are statistically significant.

FIG. 10C shows the change in TEER, FITC-dextran diffusion, and gene expression when treated with FCMs. The gene expression in the intestines of FMT-recipients and enteroids treated with FCMs from db/db and DIO mice compared to their controls. Values presented are mean (n=6-8 mice per group) and average of enteroids and Caco2 culture experiments performed in triplicates and repeated 2-3 times. Error bars as standard error of means. P values with ***<0.001 are statistically significant.

FIG. 16C shows the top 5 proteins that are abundantly binding to miR101a-3p promoter. (FIG. 16C)

FIG. 17A show in-silico analyses on search engines such as oPOSSOM V3 (FIG. 17A) that found that ARID3a has a predictive binding sequence on the miR101a-3p promoter.

FIG. 17B shows in-silico analyses on ConTra V3 (FIG. 17B) that found that ARID3a has a predictive binding sequence on the miR101a-3p promoter.

FIG. 20C shows a screen of Eut operon present in common probiotic bacterial using nucleotide BLAST analyses.

FIG. 20D shows a screen of Eut operon present in common probiotic bacterial using protein BLAST analyses.

FIG. 21 shows the predictive abundance of Eut operon expressing bacterial species and the abundance of bacterial species itself that were different in obese/T2D (both db/db and DIO) compared to B6 normal chow fed controls.

Figure 22A:
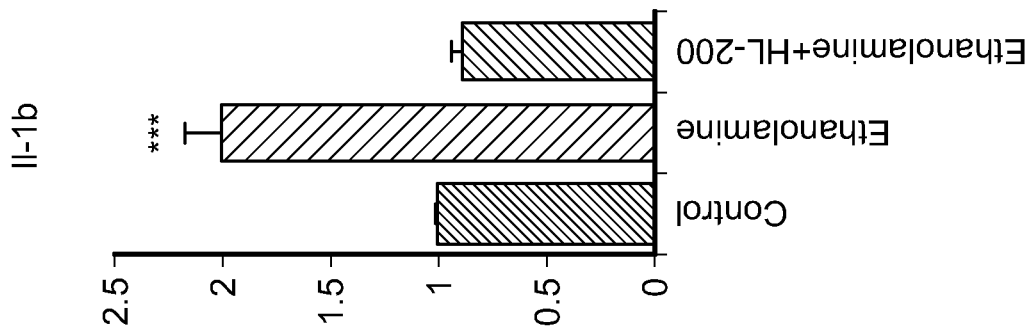

FIG. 22A shows the impact of probiotic *Lactobacillus rhamnosus* HL-200 [HL-200] expression of miR101a-3p in mice treated with ethanolamine, compared to their control groups. Values presented are mean (n=6-8 mice per group) and error bars as standard error of means. P values with ***<0.001 are statistically significant.

Figure 22B:
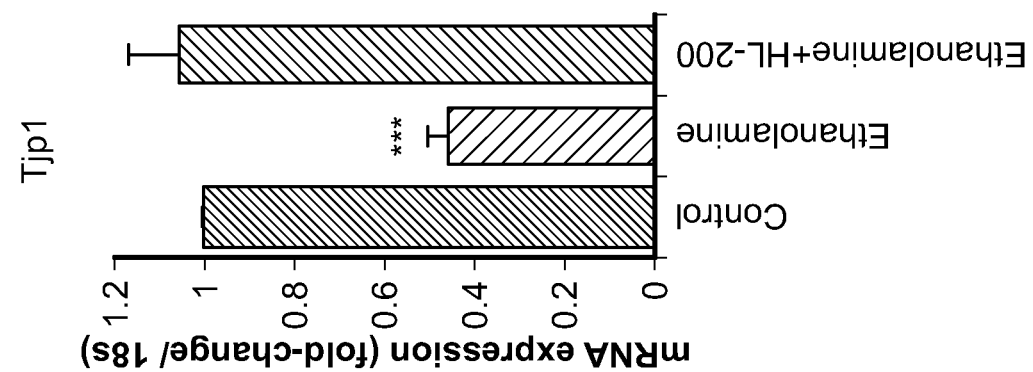

FIG. 22B shows the impact of probiotic *Lactobacillus rhamnosus* HL-200 [HL-200] expression of Tjp1 in mice treated with ethanolamine, compared to their control groups.

Values presented are mean (n=6-8 mice per group) and error bars as standard error of means. P values with ***<0.001 are statistically significant.

Figure 22C:
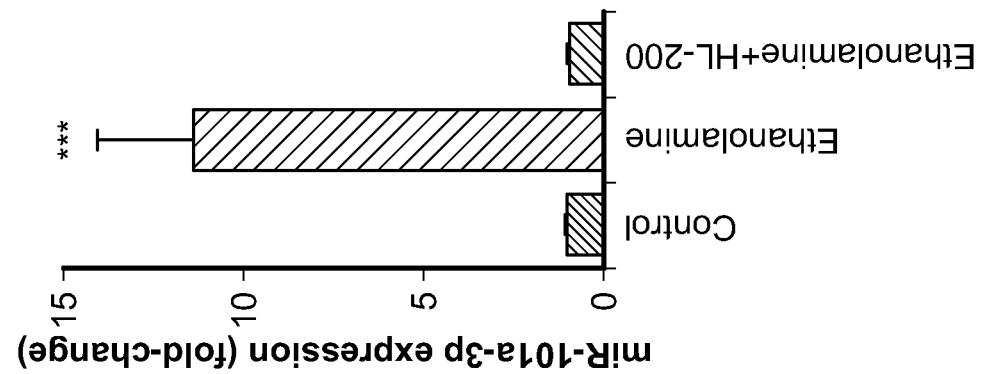

FIG. 22C shows the impact of probiotic *Lactobacillus rhamnosus* HL-200 [HL-200] expression of inflammatory marker IL1β in mice treated with ethanolamine, compared to their control groups. Values presented are mean (n=6-8 mice per group) and error bars as standard error of means. P values with ***<0.001 are statistically significant.

Figures 22D, 22E:
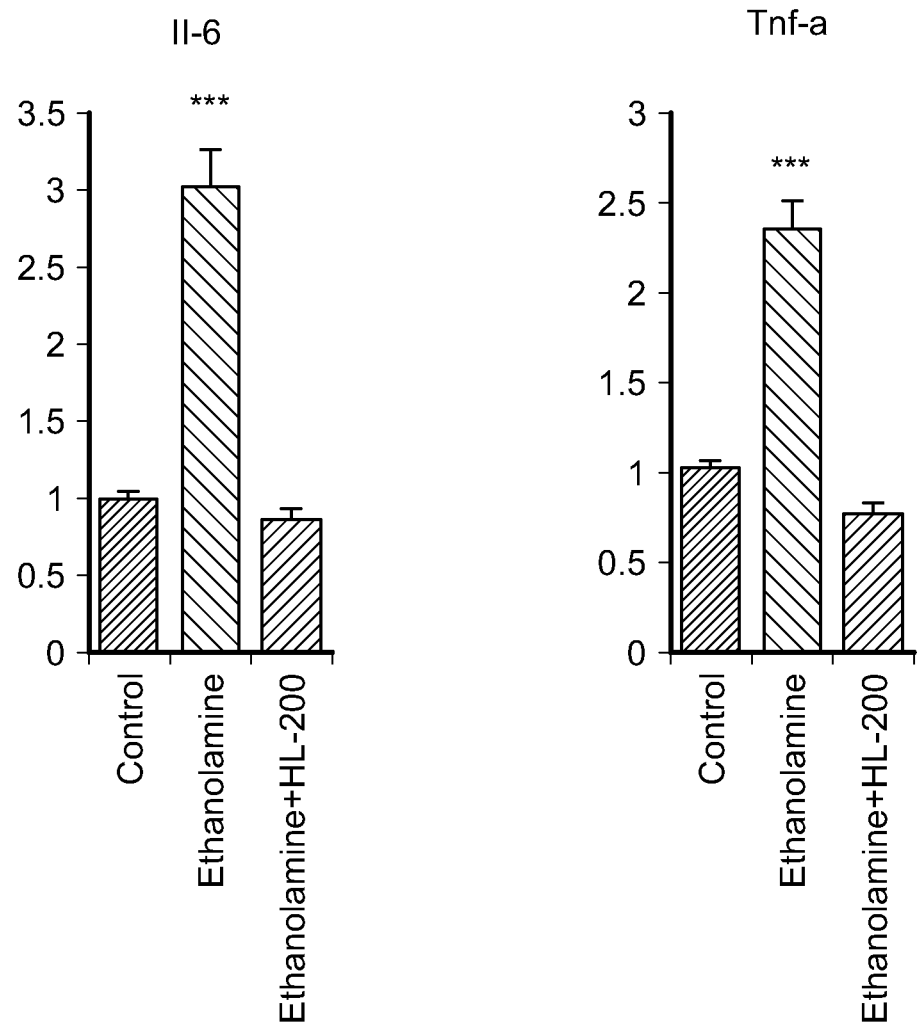

FIG. 22D shows the impact of probiotic *Lactobacillus rhamnosus* HL-200 [HL-200] expression of inflammatory marker IL-6 in mice treated with ethanolamine, compared to their control groups. Values presented are mean (n=6-8 mice per group) and error bars as standard error of means. P values with ***<0.001 are statistically significant.

FIG. 22E shows the impact of probiotic *Lactobacillus rhamnosus* HL-200 [HL-200] expression inflammatory markers TNF-α in mice treated with ethanolamine, compared to their control groups. Values presented are mean (n=6-8 mice per group) and error bars as standard error of means. P values with ***<0.001 are statistically significant.

DETAILED DESCRIPTION

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a microorganism", "a composition", or "a disorder", includes, but is not limited to, two or more such microorganisms, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise. As used herein, the term "substantially free," when used in the context of a composition or component of a composition that is substantially absent, is intended to refer to an amount that is then about 1% by weight or less, e.g., less than about 0.5% by weight, less than about 0.1% by weight, less than about 0.05% by weight, or less than about 0.01% by weight of the stated material, based on the total weight of the composition.

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control (e.g., an untreated tumor).

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those microorganisms, compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

Method

Method of Treating Increased Gut Permeability

The present disclosure, in one aspect, provides for a method of treating increased gut permeability, comprising administering a therapeutically effective amount of human derived probiotic to a patient in need thereof.

Increased gut permeability, also referred to as "leaky gut", can be a source of systemic inflammation, as it can allow for non-specific transfer of proinflammatory antigens, metabolites, and microbes from gut lumen to gut mucosa and blood. This, in turn, can stimulate an inflammatory response through local and systemic immune cells. When a patient has leaky gut, the lining of the small intestine becomes damaged and can cause undigested food particles, toxic waste products, and bacteria to leak through the intestines and flood the blood stream. The immune system can then react to the particles, waste products, and bacteria to cause inflammation. Symptoms of leaky gut can include bloating, gas, cramps, food sensitivities, aches and pains, or any combination thereof.

Human derived probiotics are strains of bacteria found in the human body. In some examples, the strains of bacteria can be found to live in the human digestive tract. In further examples, the strains of bacteria can be beneficial to a patient. In certain examples, human derived probiotics can include, but are not limited to, bacteria from the species *Lactobacillus, Bifidobacterium*, or any combination thereof.

In some examples, the human derived probiotic can include *Lactobacillus*. In specific examples, the disclosed methods and pharmaceutical compositions comprise a probiotic organism that is a *Lactobacillus* species, such as *L. acidophilus, L. amylovorus, L. brevis, L. casei, L. casei* subsp. *rhamnosus* (*Lactobacillus* GG), *L. caucasicus, L. crispatus, L. delbrueckii* subsp. *bulgaricus* (*L. bulgaricus*), *L. fermentum* (*L. fermenti*), *L. gasseri, L. helveticus, L. johnsonii, L. lactis, L. leichmannii, L. paracasei, L. plantarum, L. reuteri*, and *L. rhamnosus*.

In further examples, the *Lactobacillus* can include *L. rhamnosus*. *L. rhamnosus* (*Lactobacillus rhamnosus*) is a type of bacteria that produces the enzyme lactase. *L. rhamnosus* can survive in acidic and basic conditions within the body and therefore can adhere to and colonize the intestinal walls. *L. rhamnosus* is a lactic acid bacterium found in a large variety of ecological habitats, including artisanal and industrial dairy products, the oral cavity, intestinal tract, and vagina. There are numerous strains of *L. rhamnosus* which include, but are not limited to, F0435, H0006, H4692, H4690, H0033, AKRO, GG, IDOF, and VIFIT. These strains include dairy isolates, intestinal isolates, oral isolates, vaginal isolates, and clinical/other isolates.

In certain examples, *L. rhamnosus* can include *L. rhamnosus* strain HL-200. *Lactobacillus rhamnosus* HL-200 is one strain of *L. rhamnosus* and it can decrease ethanolamine-induced leaky gut. HL-200 can be incorporated into probiotic therapy, more specifically human-origin probiotic therapy, to reverse leaky gut and inflammation. The *L. rhamnosus* strain HL-200 was deposited with the American Type Culture Collection (ATCC), 10801 University Boulevard, Manassas, VA, USA, on Feb. 20, 2024, under the terms of the Budapest Treaty and assigned Patent Deposit—Designation PTA-127735.

In other examples, the disclosed methods and pharmaceutical compositions can include a probiotic organism that is a *Bifidobacterium* species, such as *B. adolescentis, B. bifidum, B. breve, B. infantis, B. lactis* (*B. animalis*), *B. licheniformis*, and *B. longum*. In still other examples, the disclosed methods and pharmaceutical compositions can include a probiotic organism that is lactic acid bacteria, such as *Enterococcus faecium, Lactococcus lactis, Leuconstoc mesenteroides, Pediococcus acidilactici*, and *Streptococcus thermophilus*. In yet other examples, the disclosed methods and compositions can include a probiotic organism that is a nonlactic acid bacteria such as *Bacillus subtilis, Saccharomyces boulardii*, and *Saccharomyces cerevisiae*. In further examples, the disclosed methods and pharmaceutical compositions can include a probiotic organism such as *Saccharomyces* or *Escherica*, wherein a strain of *Escherica* is *E. coli Nissle* 1917.

In specific examples, the patient can have diabetes. Diabetes is a chronic disease that occurs when the pancreas is no longer able to make insulin, or when the body cannot effectively use the insulin it produces. Types of diabetes can include Type 1 diabetes, Type 2 diabetes, or gestational diabetes. Type 1 diabetes can develop at any age, though it occurs more frequently in children and adolescents. When a patient has type 1 diabetes, their body produces very little to no insulin. This can require daily insulin injections in order to maintain healthy blood glucose levels. Gestational diabetes is a type of diabetes that includes high blood glucose during pregnancy. Gestational diabetes can disappear after pregnancy, but the women and child can be at an increased risk of developing type 2 diabetes later in life.

In some examples, the diabetes can be Type 2 diabetes. Type 2 diabetes is more common in adults and accounts for approximately 90% of all diabetes cases. A patient with type 2 diabetes does not make good use of the insulin that their body produces and as such, can require oral drugs and/or insulin to keep blood glucose levels under control. Type 2 diabetes treatment can include a healthy lifestyle, including physical activity and a healthy diet.

In further examples, the patient can be obese. A patient is obese when the subject has a body mass index (BMI) of approximately 30 or greater.

In certain examples, the therapeutically effective amount of *Lactobacillus* can be administered to the patient orally. In specific examples, the therapeutically effective amount of *Lactobacillus* can be administered to the patient in a tablet, troche, pill, or capsule. In some examples, the therapeutically effective amount of *Lactobacillus* can be administered to the patient in a solution, suspension, or emulsion. In further examples, the suspension can be a bacterial suspension.

The term "administration" and variants thereof (e.g., "administering" a microorganism) in reference to a microorganism disclosed herein means introducing the microorganism into the system of the patient in need of treatment. When a microorganism disclosed herein is provided in combination with one or more other active agents (e.g., a cytotoxic agent, etc.), "administration" and its variants are each understood to include concurrent and sequential introduction of the microorganism or prodrug thereof and other agents.

The disclosed microorganisms can be administered either sequentially or simultaneously in separate or combined pharmaceutical formulations. When one or more of the disclosed microorganisms is used in combination with a second therapeutic agent, the dose of the microorganism can be either the same as or differ from that when the microorganism is used alone. Appropriate doses will be readily appreciated by those skilled in the art.

Administration can be accomplished by any suitable method and technique presently or prospectively known to those skilled in the art. For example, the disclosed microorganisms can be formulated in a physiologically- or pharmaceutically-acceptable form and administered by any suitable route known in the art including, for example, oral routes of administration. Administration of the disclosed microorganisms or compositions can be a single administration, or at continuous or distinct intervals as can be readily determined by a person skilled in the art.

The microorganisms disclosed herein, and compositions comprising them, can also be administered utilizing liposome technology, slow release capsules, implantable pumps, and biodegradable containers. These delivery methods can, advantageously, provide a uniform dosage over an extended period of time. The microorganisms can also be administered in their crystalline forms.

The microorganisms disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the microorganisms disclosed herein can be formulated such that an effective amount of the microorganism is combined with a suitable carrier in order to facilitate effective administration of the microorganism. The compositions used can also be in a variety of forms. These include, for example, solid, semi-solid, and liquid dosage forms, such as tablets, pills, powders, liquid solutions or suspension, suppositories, injectable and infusible solutions, and sprays. The form depends on the intended mode of administration and therapeutic application. Examples of carriers or diluents for use with the microorganisms include ethanol, dimethyl sulfoxide, glycerol, alumina, starch, saline, and equivalent carriers and diluents. To provide for the administration of such dosages for the desired therapeutic treatment, compositions disclosed herein can advantageously comprise from 0.1% and 100% by weight of the total of one or more of the subject microorganisms based on the weight of the total composition including carrier or diluent.

Formulations suitable for administration include, for example, aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier prior to use. It should be understood that in addition to the ingredients particularly mentioned above, the compositions disclosed herein can include other agents conventional in the art having regard to the type of formulation in question.

Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Microorganisms and compositions disclosed herein can be systemically administered, such as orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active microorganism can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the microorganism, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the microorganism can be incorporated into sustained-release preparations and devices.

Alternatively, the microorganism can be suspended or emulsified in a non-solvent to form a suspension or emulsion. Other ingredients or components such as anti-microbial agents, stabilizing agents, dyes, and agents assisting with the drying process may optionally be added at this stage. Examples of liquid preparations include, but are not limited to, aqueous, organic, or aqueous-organic solutions, suspensions, and emulsions. The microorganism may be administered in the form of a bacterial suspension, before or after freezing, or in the form of concentrates, either in dry, lyophilized, or frozen form. Whatever the form used, the strain can be frozen.

Useful dosages of the microorganisms and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any counterindications. Dosage can vary, and can be administered in one or more dose administrations daily, for one or several days.

The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

In certain examples, the therapeutically effective amount of *Lactobacillus* can include a pharmaceutical formulation comprising a combination of *Lactobacillus* or a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use.

Pharmaceutically acceptable carriers can include, but are not limited to, inert diluents, assimilable edible carriers, binders, excipients, disintegrating agents, sweetening agents, lubricants, or flavoring agents. Examples of suitable aqueous and nonaqueous carriers, diluents, inert diluents, solvents, assimilable edible carriers, or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

In specific examples, the pharmaceutically acceptable carrier can include a binder, excipient, disintegrating agent, sweetening agent, lubricant, flavoring agent, inert diluent, assimilable edible carrier, or any combination thereof.

In some embodiments, binder can include gum tragacanth, acacia, corn starch, gelatin, or any combination thereof. In further embodiments, excipients can include dicalcium phosphate, lactose, starch, cellulose, milk sugar, or high molecular weight polyethylene glycols. In certain embodiments, disintegrating agent can include corn starch, potato starch, alginic acid, or any combination thereof. In specific embodiments, sweetening agent can include sucrose, fructose, lactose, aspartame, or any combination thereof. In some embodiments, lubricant can include magnesium stearate. In further embodiments, flavoring agent can include peppermint, oil of wintergreen, cherry flavoring, or any combination thereof. In certain embodiments, inert diluent can include anhydrous lactose, lactose monohydrate, sugar alcohols, such as sorbitol, xylitol, or mannitol, or any combination thereof. In specific embodiments, assimilable edible carrier can include polysaccharides, polymers, pectin, polypeptides, or any combination thereof.

In some examples, the therapeutically effective amount of *Lactobacillus* is from $10^6$ to $10^9$ CFU in the pill. In further examples, the therapeutically effective amount of *Lactobacillus* is from $10^6$ to $10^7$, $10^7$ to $10^8$, or $10^8$ to $10^9$ CFU in the pill. In further examples, the therapeutically effective amount of *Lactobacillus* is from $10^6$ to $5 \times 10^6$, $5 \times 10^6$ to $10^7$, $10^7$ to $5 \times 10^7$, $5 \times 10^7$ to $10^8$, $10^8$ to $5 \times 10^8$, or $5 \times 10^8$ to $10^9$ CFU in the pill. In certain examples, $10^6$ to $2.5 \times 10^6$, $2.5 \times 10^6$ to $5 \times 10^6$, $5 \times 10^6$ to $7.5 \times 10^6$, $7.5 \times 10^6$ to $10^7$, $10^7$ to $2.5 \times 10^7$, $2.5 \times 10^7$ to $5 \times 10^7$, $5 \times 10^7$ to $7.5 \times 10^7$, $7.5 \times 10^7$ to $10^8$, $10^8$ to $2.5 \times 10^8$, $2.5 \times 10^8$ to $5 \times 10^8$, $5 \times 10^8$ to $7.5 \times 10^8$, or $7.5 \times 10^8$ to $10^9$ CFU in the pill.

In further examples, the therapeutically effective amount of *Lactobacillus* is from $10^6$ to $10^9$ CFU per day. In some examples, the therapeutically effective amount of *Lactobacillus* is from $10^6$ to $10^7$, $10^7$ to $10^8$, or $10^8$ to $10^9$ CFU per day. In further examples, the therapeutically effective amount of *Lactobacillus* is from $10^6$ to $5 \times 10^6$, $5 \times 10^6$ to $10^7$, $10^7$ to $5 \times 10^7$, $5 \times 10^7$ to $10^8$, $10^8$ to $5 \times 10^8$, or $5 \times 10^8$ to $10^9$ CFU per day. In certain examples, $10^6$ to $2.5 \times 10^6$, $2.5 \times 10^6$ to $5 \times 10^6$, $5 \times 10^6$ to $7.5 \times 10^6$, $7.5 \times 10^6$ to $10^7$, $10^7$ to $2.5 \times 10^7$, $2.5 \times 10^7$ to $5 \times 10^7$, $5 \times 10^7$ to $7.5 \times 10^7$, $7.5 \times 10^7$ to $10^8$, $10^8$ to $2.5 \times 10^8$, $2.5 \times 10^8$ to $5 \times 10^8$, $5 \times 10^8$ to $7.5 \times 10^8$, or $7.5 \times 10^8$ to $10^9$ CFU per day.

In certain examples, the therapeutically effective amount of *Lactobacillus* is from $5 \times 10^4$ to $10^{11}$ CFU/kg. In some examples, the therapeutically effective amount of *Lactobacillus* is from $5 \times 10^4$ to $10^5$, $10^5$ to $10^6$, $10^6$ to $10^7$, $10^7$ to $10^8$, $10^8$ to $10^9$, $10^9$ to $10^{10}$, or $10^{10}$ to $10^{11}$ CFU/kg. In further examples, the therapeutically effective amount of *Lactobacillus* is from $5 \times 10^4$ to $10^5$, $10^5$ to $5 \times 10^5$, $5 \times 10^5$ to $10^6$, $10^6$ to $5 \times 10^6$, $5 \times 10^6$ to $10^7$, $10^7$ to $5 \times 10^7$, $5 \times 10^7$ to $10^8$, $10^8$ to $5 \times 10^8$, $5 \times 10^8$ to $10^9$, $10^9$ to $5 \times 10^9$, $5 \times 10^9$ to $10^{10}$, $10^{10}$ to $5 \times 10^{10}$, or $5 \times 10^{10}$ to $10^{11}$ CFU/kg. In certain examples, $5 \times 10^4$ to $7.5 \times 10^4$, $7.5 \times 10^4$ to $10^5$, $10^5$ to $2.5 \times 10^5$, $2.5 \times 10^5$ to $5 \times 10^5$, $5 \times 10^5$ to $7.5 \times 10^5$, $7.5 \times 10^5$ to $10^6$, $10^6$ to $2.5 \times 10^6$, $2.5 \times 10^6$ to $5 \times 10^6$, $5 \times 10^6$ to $7.5 \times 10^6$, $7.5 \times 10^6$ to $10^7$, $10^7$ to $2.5 \times 10^7$, $2.5 \times 10^7$ to $5 \times 10^7$, $5 \times 10^7$ to $7.5 \times 10^7$, $7.5 \times 10^7$ to $10^8$, $10^8$ to $2.5 \times 10^8$, $2.5 \times 10^8$ to $5 \times 10^8$, $5 \times 10^8$ to $7.5 \times 10^8$, $7.5 \times 10^8$ to $10^9$, $10^9$ to $2.5 \times 10^9$, $2.5 \times 10^9$ to $5 \times 10^9$, $5 \times 10^9$ to $7.5 \times 10^9$, $7.5 \times 10^9$ to $10^{10}$, $10^{10}$ to $2.5 \times 10^{10}$, $2.5 \times 10^{10}$ to $5 \times 10^{10}$, $5 \times 10^{10}$ to $7.5 \times 10^{10}$, or $7.5 \times 10^{10}$ to $10^{11}$ CFU/kg.

Method of Increasing a Patient's Metabolism of Ethanolamine

Also provided herein is a method of increasing a patient's metabolism of ethanolamine, comprising administering a therapeutically effective amount of human derived probiotics to the patient in need thereof. In some examples, the probiotic can include *Lactobacillus*. In further examples, the *Lactobacillus* can include *L. rhamnosus*. In certain examples, the *L. rhamnosus* can include *L. rhamnosus* strain HL-200.

Composition
Pharmaceutical Composition

Provided herein is a pharmaceutical composition, comprising a first strain of *Lactobacillus* and a second probiotic strain. In some examples, the first strain of *Lactobacillus* can include *L. rhamnosus*. In further examples, *L. rhamnosus* can include *L. rhamnosus* strain HL-200.

In certain examples, the second probiotic strain can include a probiotic strain of *Lactobacillus plantarum*, *Lactobacillus reuteri*, *Lactobacillus casei*, *Lactobacillus helveticus*, or any combination thereof.

In specific examples, the second probiotic strain can include *Lactobacillus rhamnosus* GG. In some examples, the second probiotic strain can include a probiotic strain of *Bifidobacterium infantis*. In further examples, the second probiotic strain can include a probiotic strain of *Saccharomyces boulardii*. In certain examples, the second probiotic strain can include a probiotic strain of *Escherica coli Nissle* 1917.

Also provided herein is a pharmaceutical composition, comprising *Lactobacillus* and an antidiabetic drug. Antidiabetic drugs help a person with diabetes control the levels of glucose in the blood. Antidiabetic drugs include insulin and oral hypoglycemic agents. Classes of oral antidiabetic medications can include, but are not limited to, biguanides, sulfonylureas, meglitinide, thiazolidinedione, dipeptidyl peptidase 4 inhibitors, sodium-glucose cotransporter inhibitors, and α-glucosidase inhibitors.

In certain examples, the antidiabetic drug can include metformin, carbutamide, chlorpropamide, glibenclamide, gliclazide, glimepiride, glipizide, gliquidone, tolazamide, tolbutamide), acarbose, miglitol, voglibose, pioglitazone, rivoglitazone, rosiglitazone, nateglinide, repaglinide, mitiglinide, alogliptin, saxagliptin, sitagliptin, vildagliptin, exenatide, liraglutide, albiglutide, pramlintide, insulin lispro, insulin aspart, insulin glulisine, insulin glargine, insulin detemir, aleglitazar, dapagliflozin, remogliflozin, sergliflozin, or any combination thereof.

In some examples, *Lactobacillus* can include *L. rhamnosus*. In further examples, *L. rhamnosus* can include *L. rhamnosus* strain HL-200.

In specific examples, the antidiabetic drug comprises biguanide, a sulfonylurea, an alpha-glucosidase inhibitor, a thiazolidinedione, a meglitinide, a dipeptidyl peptidase-4 (DPP-4) inhibitor, a glucagon-like peptide-1 analog, an amylin, a fast acting insulin analog, a long acting insulin analog, a dual PPAR agonist, an SGLT2 inhibitor, or any combination thereof.

Further provided herein is a pharmaceutical composition, comprising *Lactobacillus* and a weight management drug. In certain examples, the weight management drug can include orlistat, phentermine-topiramate, naltrexone-bupropion, liraglutide, semaglutide, setmelanotide, phentermine, benzphetamine, diethylpropion, phendimetrazine, or any combination thereof. Weight management drugs are meant to help people who have health problems related to overweight or obesity. Weight management drugs can work via different mechanisms, while some drugs help the patient to feel less hungry or full sooner (e.g., phentermine-topiramate, naltrexone-bupropion, liraglutide, semaglutide, setmelanotide, phentermine, benzphetamine, diethylpropion, phendimetrazine) and others can make it harder for the body to absorb fat from foods that are eaten by the patient (e.g., orlistat).

In some examples, *Lactobacillus* can include *L. rhamnosus*. In further examples, *L. rhamnosus* can include *L. rhamnosus* strain HL-200.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

A Mechanism by which Obese/Diabetic Microbiota Instigates Leaky Gut and Inflammation Obesity/T2D Microbiota Instigated Leakiness and Inflammation in Gut by Reducing Tight Junctions, Which in Turn Triggered Metabolic Dysfunction.

Figure 1A:
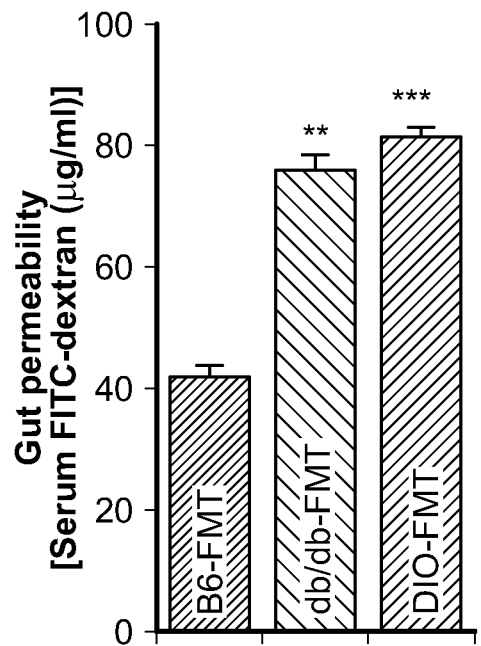
FIG. 1A shows mice receiving FMT from both db/db and DIO mice show significantly increased FITC-dextran leakage from gut to blood compared to their control C57BL/6J (B6) FMT recipient mice.
Figure 1B:
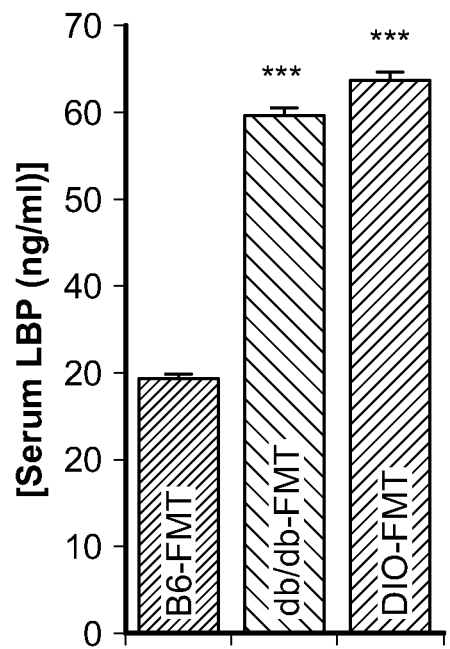
FIG. 1B shows that these mice also show significantly increased levels of a systemic marker of leaky gut: LBP.
Figure 1C:
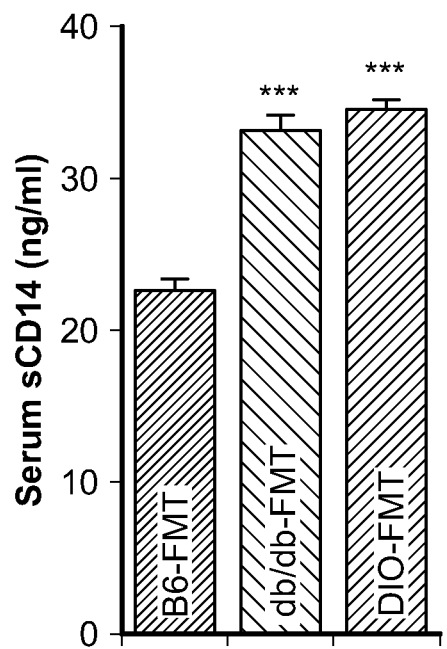
FIG. 1C shows that these mice also show significantly increased levels of a systemic marker of leaky gut: sCD14.
Figure 1D:
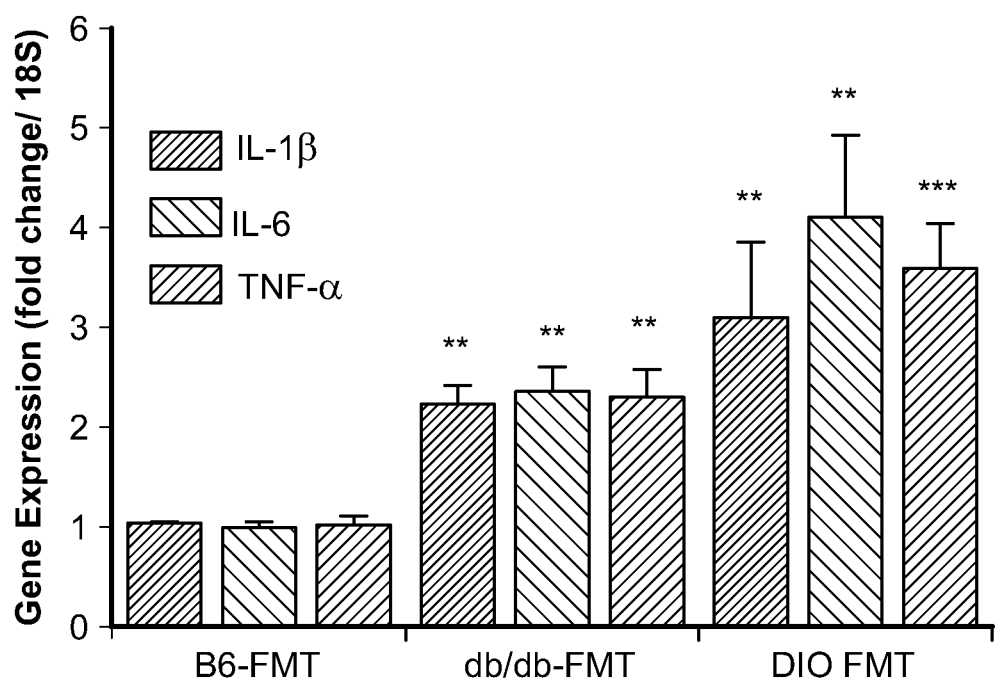
FIG. 1D shows the mRNA expression of inflammatory markers (IL-1 β, IL-6, and TNF-α).
Figure 1E:
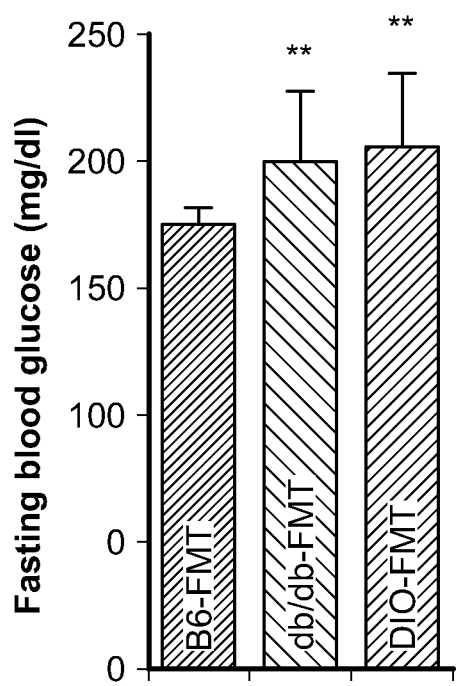
FIG. 1E shows that the mice also showed increased fasting hyperglycemia.
Figure 1F:
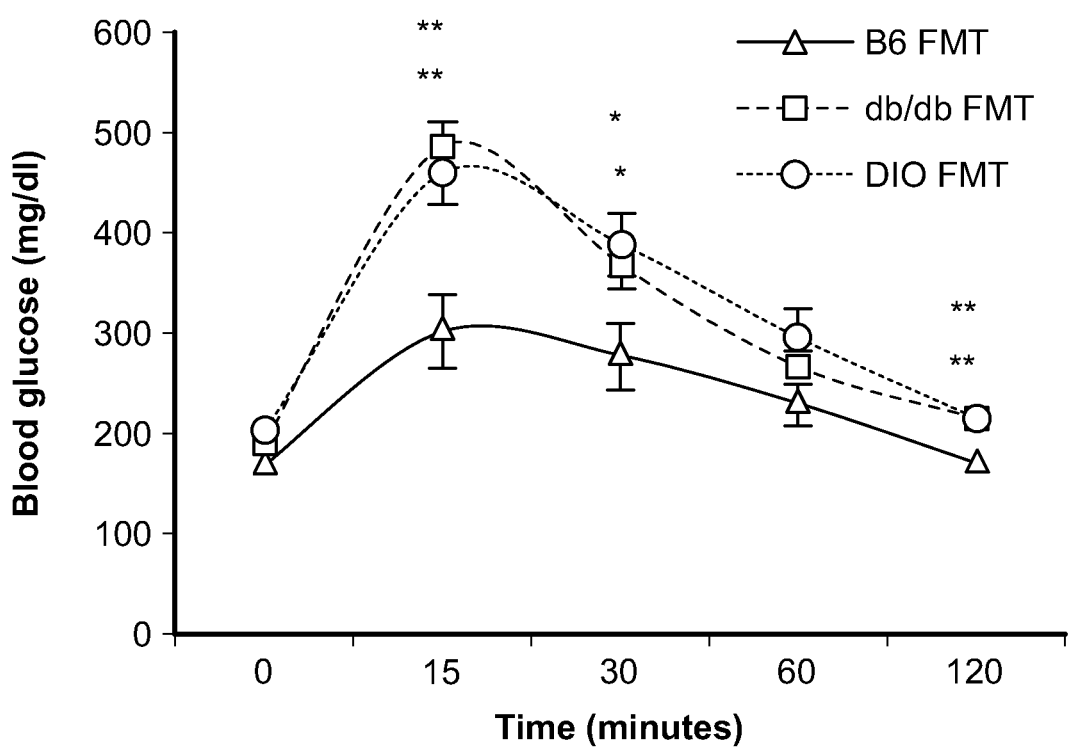
FIG. 1F shows that the mice showed an impaired meal tolerance test when compared to their B6 control recipients.
Figure 8A:
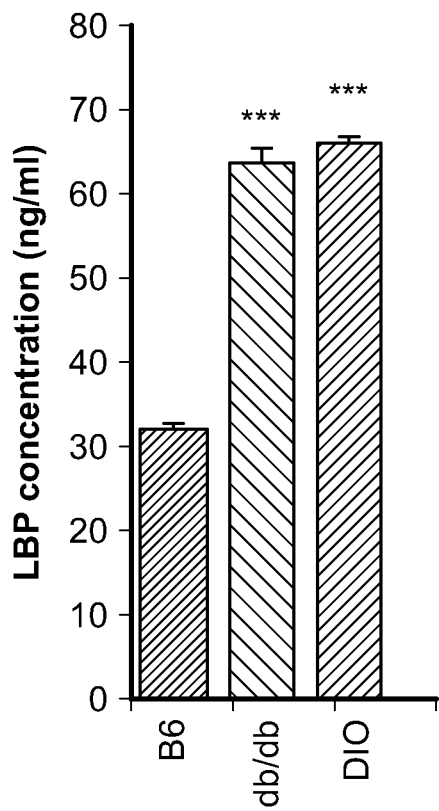
FIG. 8A shows that Obese/T2D mice have increased systemic markers of leaky gut in their serum. The levels of lipopolysaccharide binding protein, LBP were significantly higher in obese (db/db and DIO-diet induced obese) mice vs. control (B6 NC [normal chow]) mice. Values presented are mean (n=6-8 mice per group) and error bars as standard error of means. P values with ***<0.001 are statistically significant.
Figure 8B:
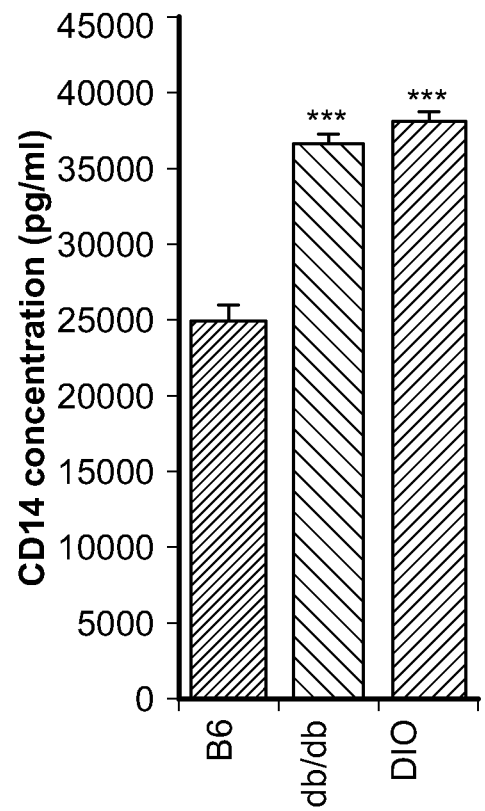
FIG. 8B shows that Obese/T2D mice have increased systemic markers of leaky gut in their serum. The levels of sCD14 were significantly higher in obese (db/db and DIO-diet induced obese) mice vs. control (B6 NC [normal chow]) mice. Values presented are mean (n=6-8 mice per group) and error bars as standard error of means. P values with ***<0.001 are statistically significant.
Figure 9A:
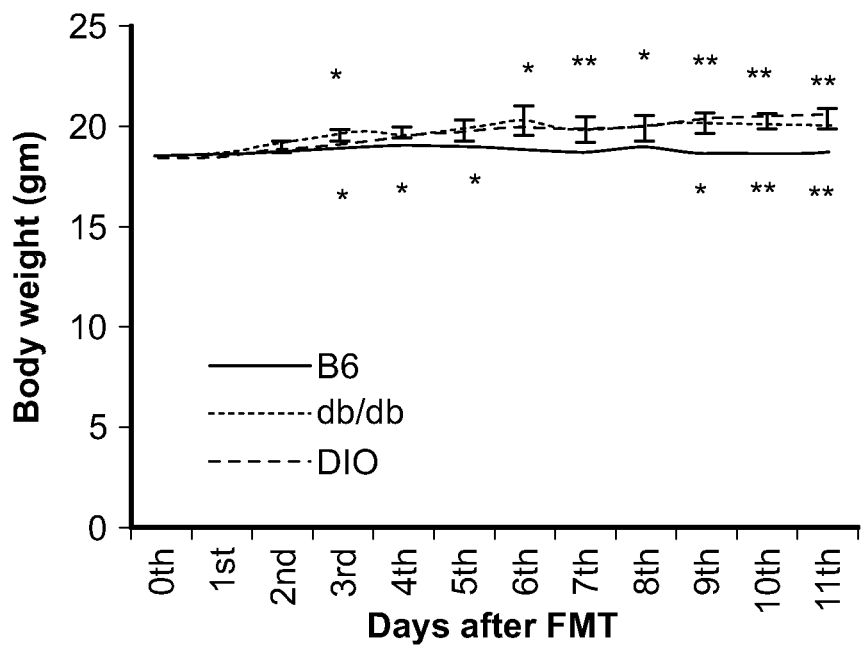
FIG. 9A shows the impact of fecal microbiome transplantation from db/db and DIO mice on body weight in recipient mice. Values presented are mean (n=6-8 mice per group) and error bars as standard error of means. P values with *<0.05; 0.001; *<0.001 are statistically significant.
Figure 9B:
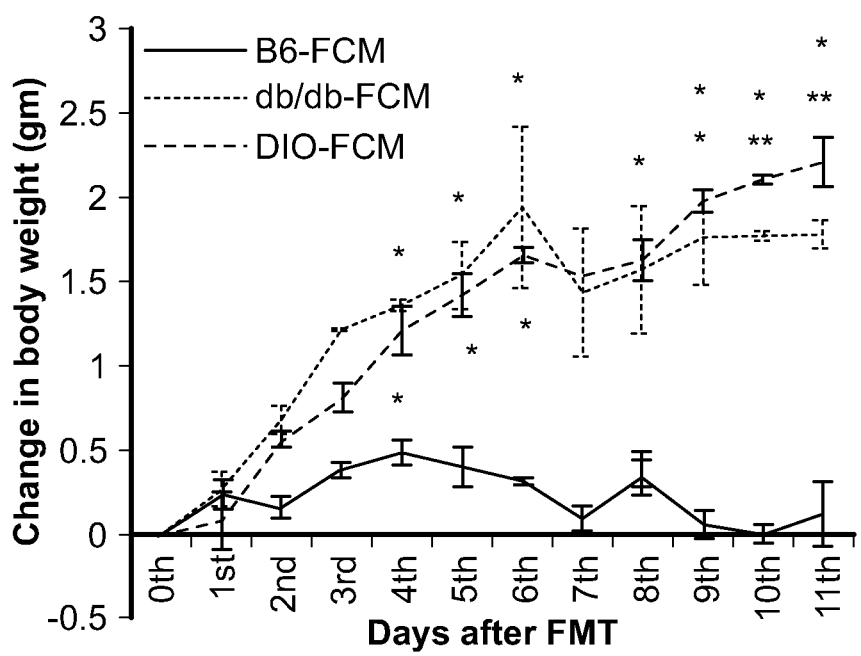
FIG. 9B shows the impact of fecal microbiome transplantation from db/db and DIO mice on change in body weight in recipient mice. Values presented are mean (n=6-8 mice per group) and error bars as standard error of means. P values with *<0.05; 0.001; *<0.001 are statistically significant.
Figure 9C:
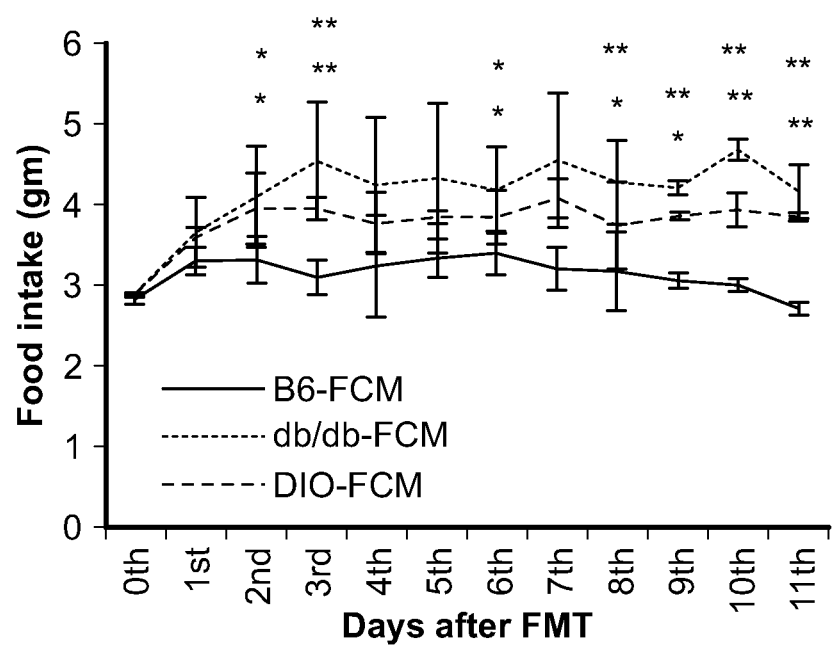
FIG. 9C shows the impact of fecal microbiome transplantation from db/db and DIO mice on food intake in recipient mice. Values presented are mean (n=6-8 mice per group) and error bars as standard error of means. P values with *<0.05; 0.001; *<0.001 are statistically significant.

Obese/T2D FMTs induce leaky gut, inflammation, and metabolic dysfunctions in mice. Despite knowing that the obese/T2D gut harbors an abnormal microbiota along with increased leaky gut and inflammation (Tilg et al., 2020; Turnbaugh et al., 2006; Ley et al., 2006) the direct evidence of whether gut microbiota induces leaky gut remained elusive. Interestingly, the FMTs of obese/T2D (both DIO and db/db) significantly increased leaky gut (measured by increased diffusion of FITC-dextran from gut to blood; and levels of lipopolysaccharide binding protein [LBP] and soluble CD14 [sCD14] in serum) and expression of inflammatory markers (interleukin-1beta [IL-1β], IL-6 and tumor necrosis factor factor-alpha [TNF-α]) in the gut of normal conventional recipient mice (FIGS. 1A-1D). These changes in leaky gut markers and inflammation were similar to the donor mice (FIGS. 8A-8B; see also Nagpal et al., 2018 and Nagpal et al., 2020). Obese/T2D FMTs also significantly increased metabolic dysfunctions such as increases in body weight gain and food intake, fasting blood glucose, and meal intolerance in recipient mice (FIGS. 1E-1F; FIGS. 9A-9C). These results demonstrate that FMTs of obese/T2D microbiota instigated leaky gut and inflammation along with metabolic dysfunctions in recipient mice.

Fecal conditioned media (FCM) recapitulates FMT in intestinal monolayer cells model. Further, treatment of FCM prepared from feces of DIO and db/db mice significantly reduced the trans-epithelial exchange ratio (TEER) and increased diffusion of FITC-dextran through Caco2 cell monolayers compared to control mice FCM (FIGS. 10A-10B). These results indicated that FCM treatments exhibit similar results of obese/T2D FMTs in intestinal monolayer cell model, indicating FCM recapitulated FMT effects on intestinal barrier functions.

Both obese/T2D FMT and FCM reduces expression of tight junctions in mouse intestines, cells, and enteroid models. To decipher the mechanism(s) by which obese/T2D microbiota instigates leaky gut and inflammation, a gene array was used to determine key genes (n=53) of intestinal epithelia and inflammatory markers; and unbiased random forest analysis revealed that the tight junction protein-1

Figure 1G:
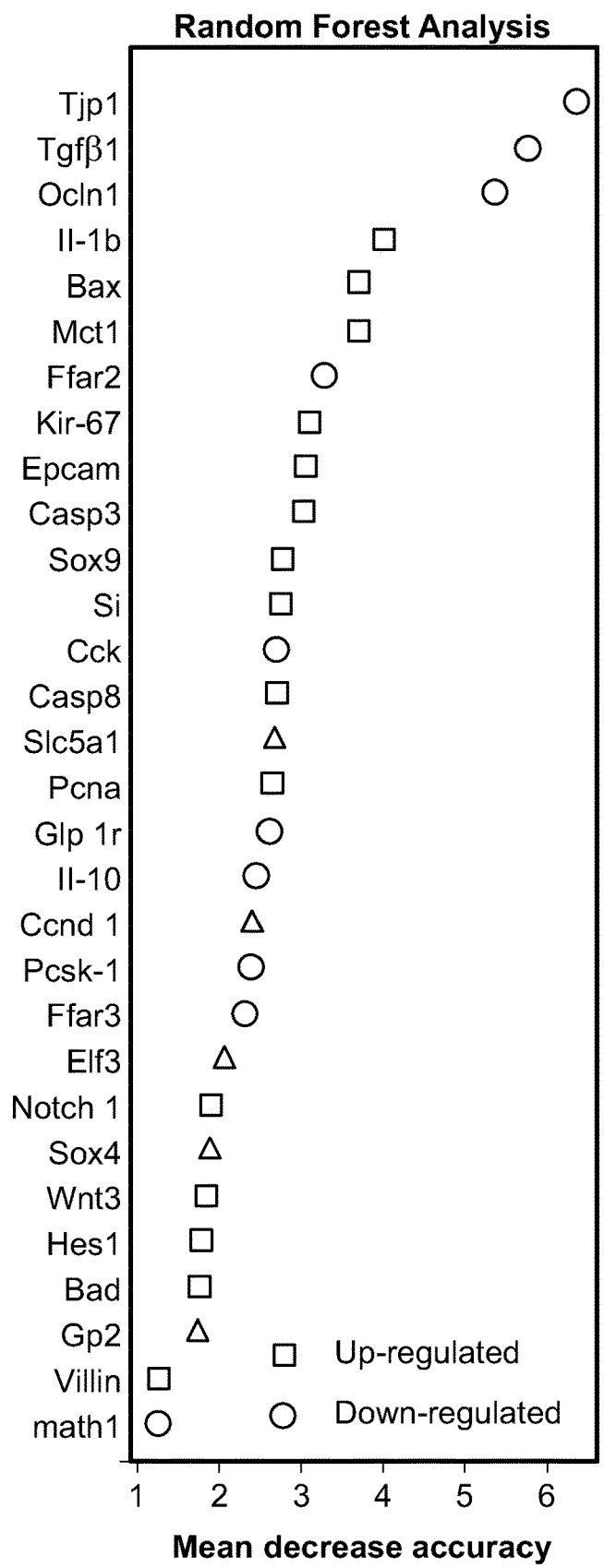
FIG. 1G shows random forest analysis of gene expression data that revealed that FMTs and FCMs of obese/T2D mice dramatically reduced Tjp1 expression in intestine and enteroids, respectively, compared to their B6 recipient controls.
Figure 1H:
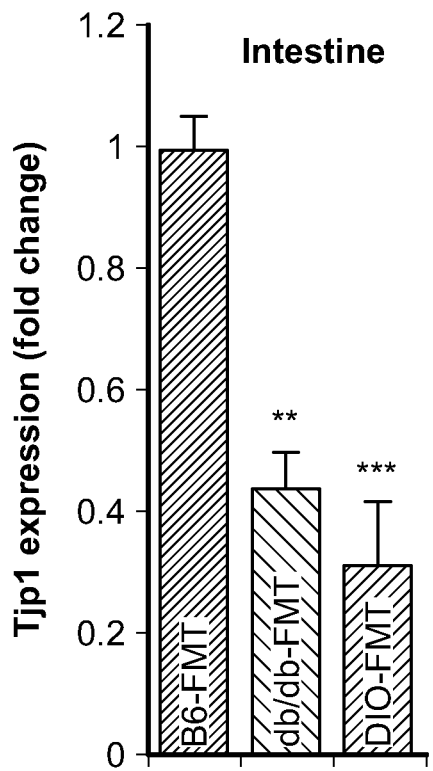
FIG. 1H shows the expression of reduced TJp1 mRNA in the ileum of obese/T2D FMTs recipient mice and FCMs treated enteroids and Caco2 cells, respectively compared to their controls. Values presented are mean (n=6-8 mice per group) and error bars as standard error of means. Enteroids and Caco2 culture experiments were performed in triplicates and repeated 2-3 times. P values with *<0.05; <0.01 and *<0.001 are statistically significant.
Figure 1I:
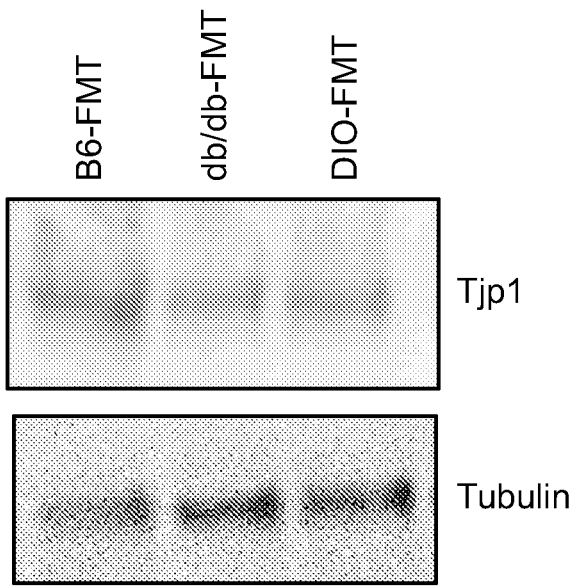
FIG. 1I shows the expression of reduced protein in the ileum of obese/T2D FMTs recipient mice and FCMs treated enteroids and Caco2 cells, respectively compared to their controls. Values presented are mean (n=6-8 mice per group) and error bars as standard error of means. Enteroids and Caco2 culture experiments were performed in triplicates and repeated 2-3 times. P values with *<0.05; <0.01 and *<0.001 are statistically significant.
Figure 1J:
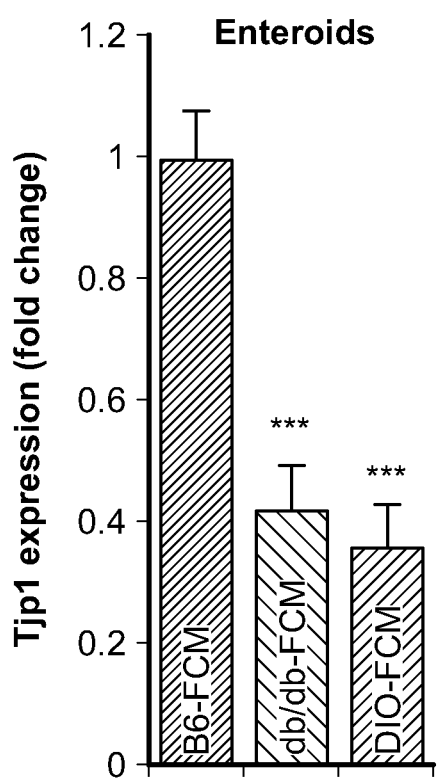
FIG. 1J shows the expression of reduced Tjp1 and mRNA and enteroids of obese/T2D FMTs recipient mice and FCMs treated enteroids and Caco2 cells, respectively compared to their controls. Values presented are mean (n=6-8 mice per group) and error bars as standard error of means. Enteroids and Caco2 culture experiments were performed in triplicates and repeated 2-3 times. P values with *<0.05; <0.01 and *<0.001 are statistically significant.
Figure 1K:
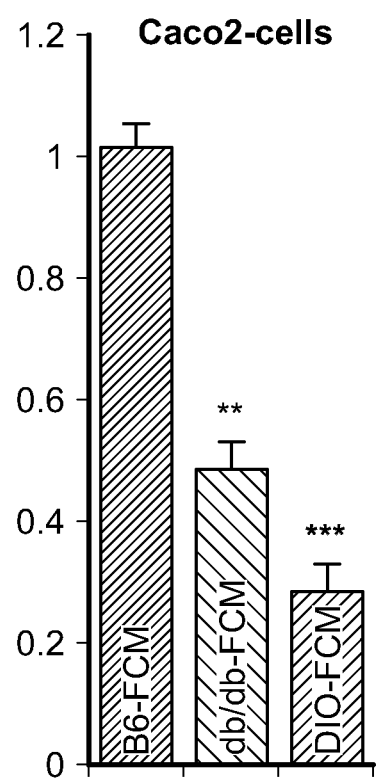
FIG. 1K shows the expression of reduced Tjp1 mRNA and Caco2 cells of obese/T2D FMTs recipient mice and FCMs treated enteroids and Caco2 cells, respectively compared to their controls. Values presented are mean (n=6-8 mice per group) and error bars as standard error of means. Enteroids and Caco2 culture experiments were performed in triplicates and repeated 2-3 times. P values with *<0.05; <0.01 and *<0.001 are statistically significant.

(Tjp1; also known as zonulin) expression was most significantly reduced in the intestine of FMT recipients and intestinal organoids (enteroids) treated with FCM of obese/T2D feces compared to controls (FIG. 1G). Further, differential gene expression analysis (volcano graphs) also showed that the Tjp1 along with other tight junction genes like occludin 1 (Ocln1) were significantly decreased in the intestine and enteroids treated with obese/T2D FMTs and FCMs, respectively (FIG. 10C); a conclusion which was further confirmed to be significantly decreased in the intestine, enteroids, and Caco2 cells treated with obese/T2D FMT and FCM, respectively (FIGS. 1H-1K). Overall, these results demonstrated that the obese/T2D microbiota instigated leaky gut by reducing the expression of Tjp1, thus weakening intestinal barrier functions.

Figure 2A:
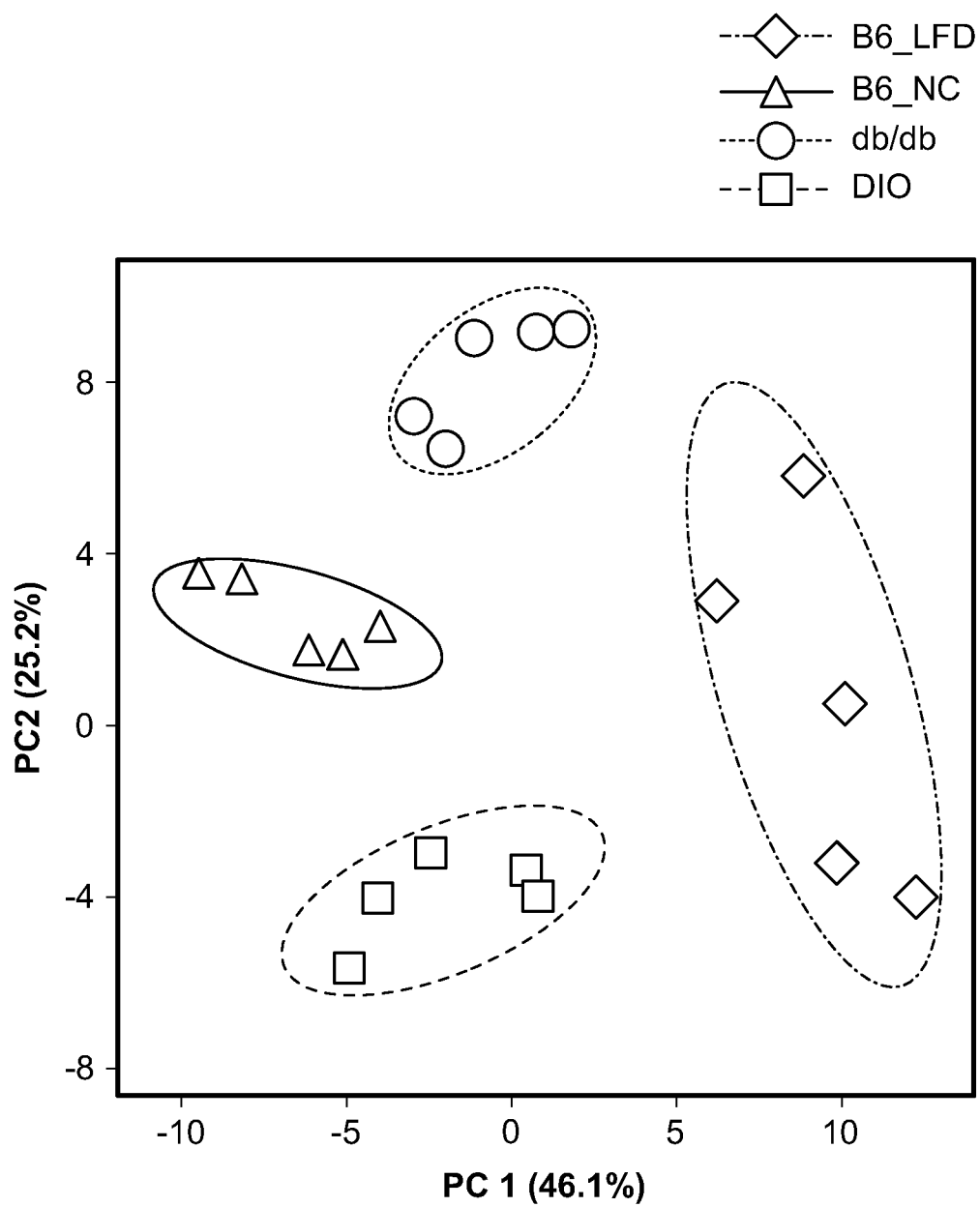
FIG. 2A shows principal component analysis (PCA) of metabolomics data which shows that metabolites in the feces of obese/T2D (db/db [red] and DIO [blue]) mice compared to their controls (B6 NC [black] and B6 LFD [gold accent]) mice are significantly distinct.
Figure 2B:
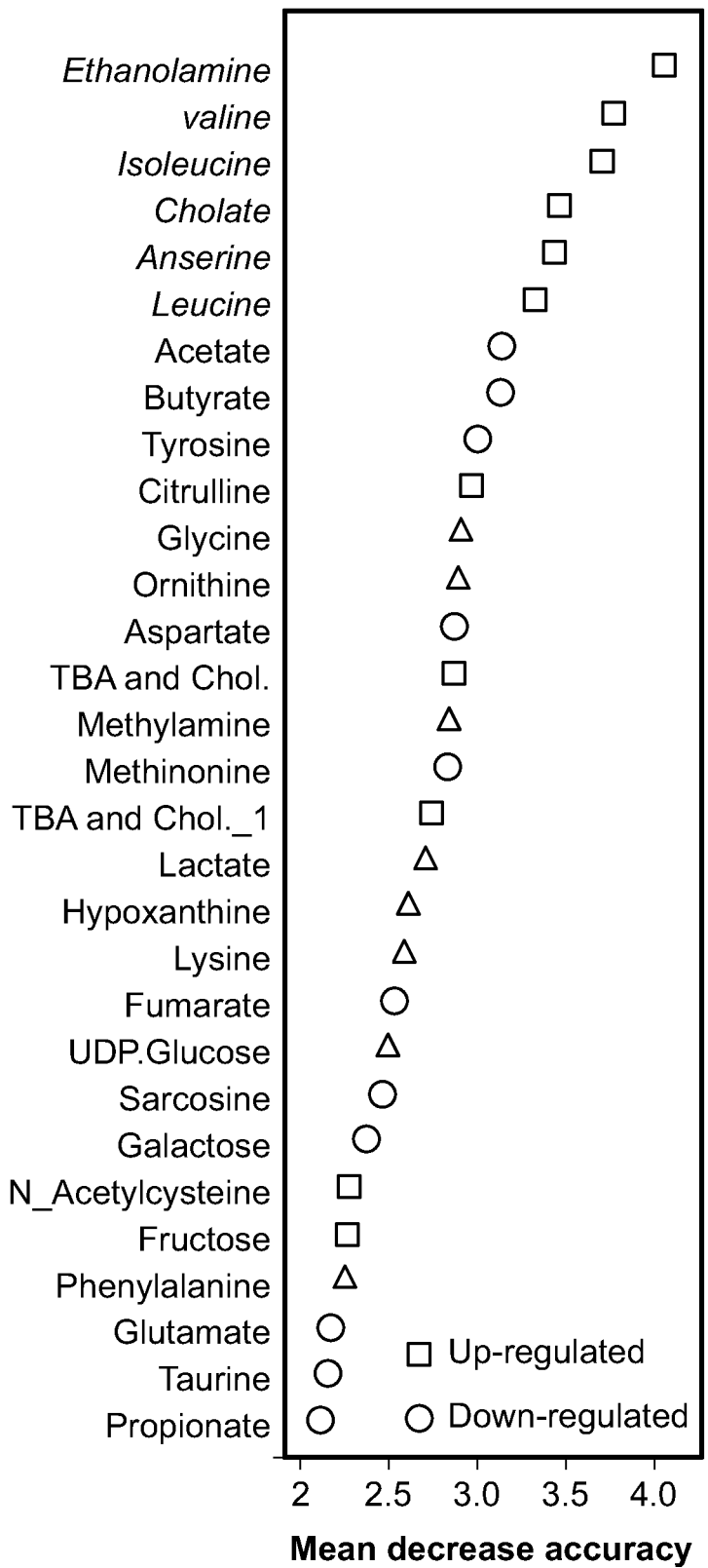
FIG. 2B shows unbiased random forest analysis that shows that ethanolamine abundance was significantly higher in obese/T2D gut compared to their controls.
Figure 11A:
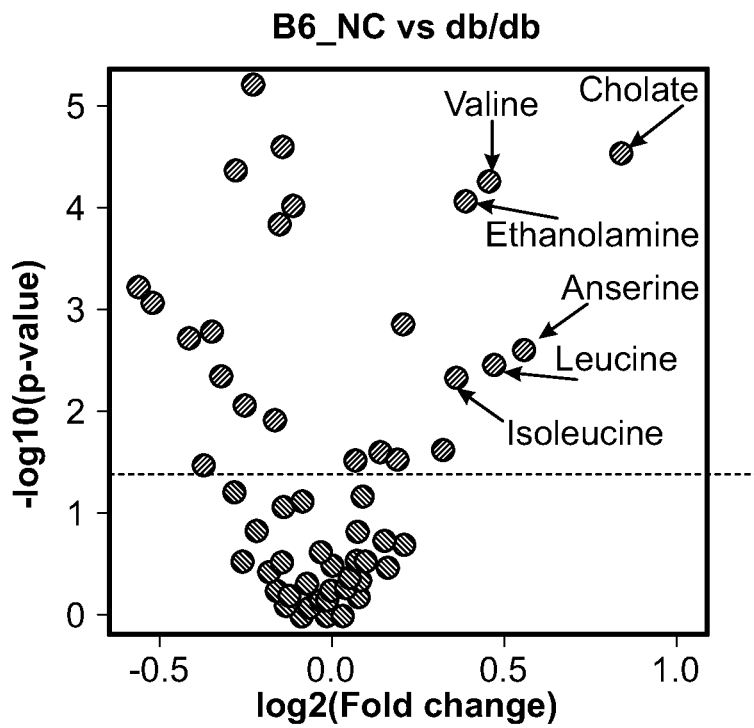
FIG. 11A show volcano graphs depicting the abundance of metabolites in the feces of donor db/db mice compared to their controls. Values presented are mean (n=6-8 mice per group).
Figure 11B:
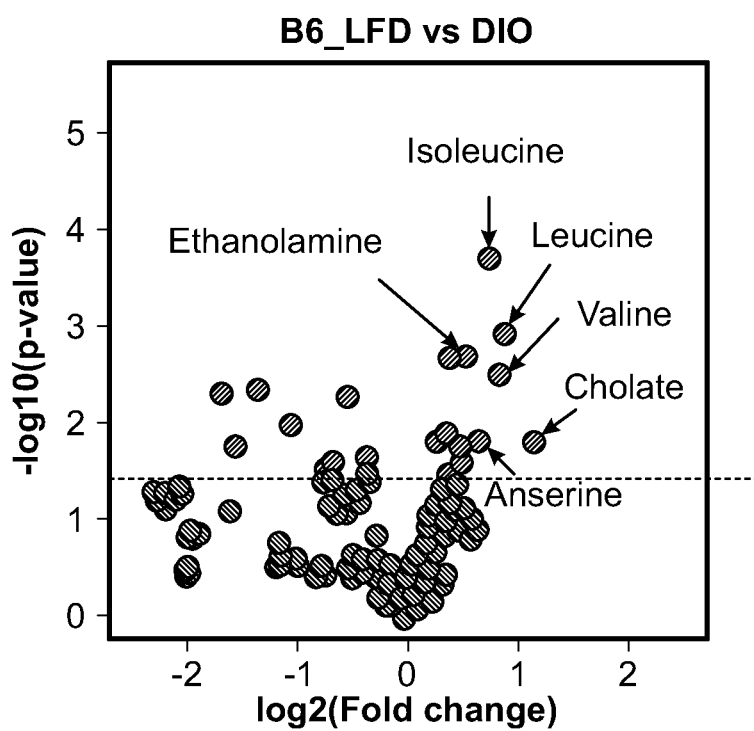
FIG. 11B shows volcano graphs depicting the abundance of metabolites in the feces of donor DIO mice compared to their controls. Values presented are mean (n=6-8 mice per group).

Obese/T2D gut has higher ethanolamine, which induced leaky gut and inflammation. To determine how gut microbiota decreases Tjp1 expression in the intestine, our unbiased, untargeted global metabolomics and principal component analysis showed that obese/T2D (both DIO and db/db) gut harbors a unique and significantly distinct metabolite signature compared to their controls (LFD-fed and NC fed, respectively) (FIG. 2A). Further, unbiased random forest and differential abundance analyses revealed that the six metabolites named ethanolamine, valine, isoleucine, cholate, anserine, and leucine were highest in the gut of DIO and db/db mice compared to the age, sex, and diet-matched controls (FIG. 2B; FIGS. 11A-11B).

Figure 2C:
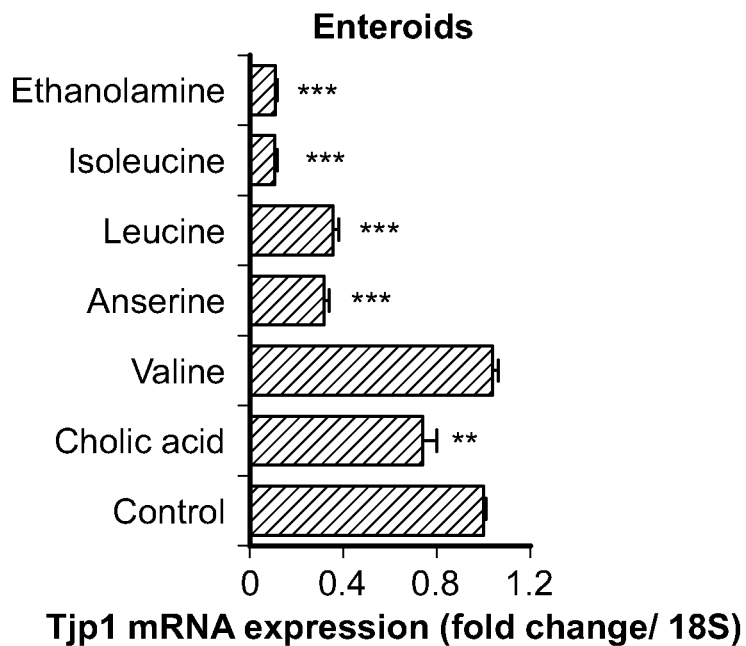
FIG. 2C shows that ethanolamine most dramatically reduced the expression of Tjp1 mRNA in the enteroids among top 6 selected metabolites such as isoleucine, leucine, anserine, valine and cholic acid.
Figure 2D:
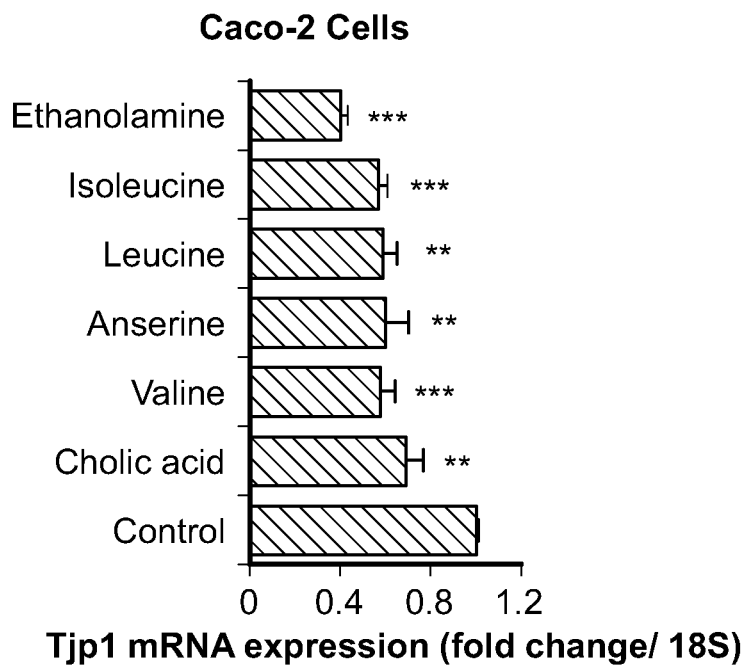
FIG. 2D shows that ethanolamine most dramatically reduced the expression of Tjp1 mRNA in the Caco2 cells among top 6 selected metabolites such as isoleucine, leucine, anserine, valine and cholic acid.
Figures 2E, 2F:
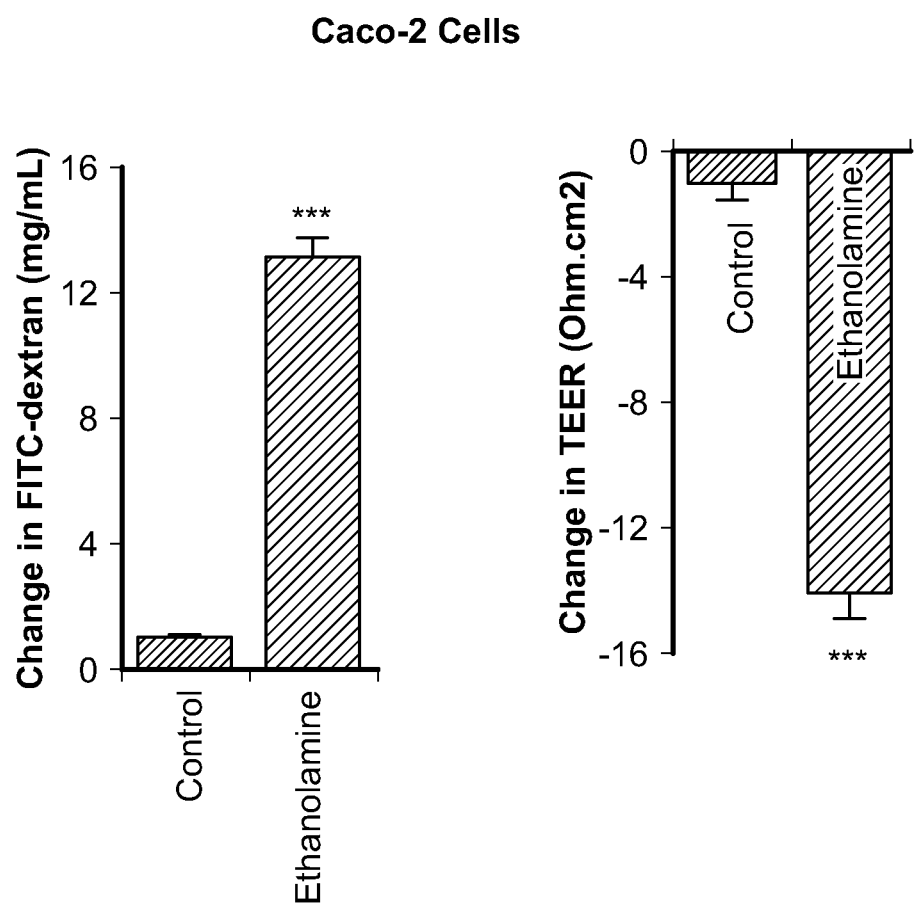
FIG. 2E shows that ethanolamine treatment also dramatically increased the permeability of FITC-dextran in the monolayers of Caco2 cells.
FIG. 2F shows reduced TEER in the monolayers of Caco2 cells.
Figure 2G:
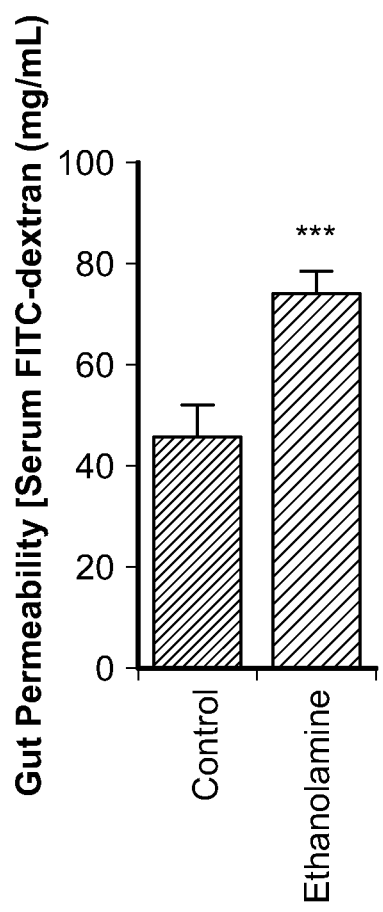
FIG. 2G shows that oral administration of ethanolamine (100 mg/kg body weight, one dose) in mice significantly increased leaky gut (FITC-dextran assay).
Figure 2H:
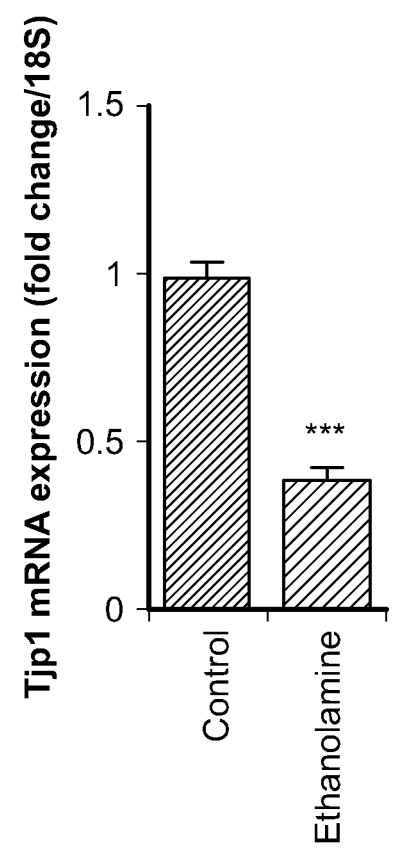
FIG. 2H shows that oral administration of ethanolamine (100 mg/kg body weight, one dose) in mice significantly reduced expression of mRNA in the ileum compared to non-treated controls. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 2I:
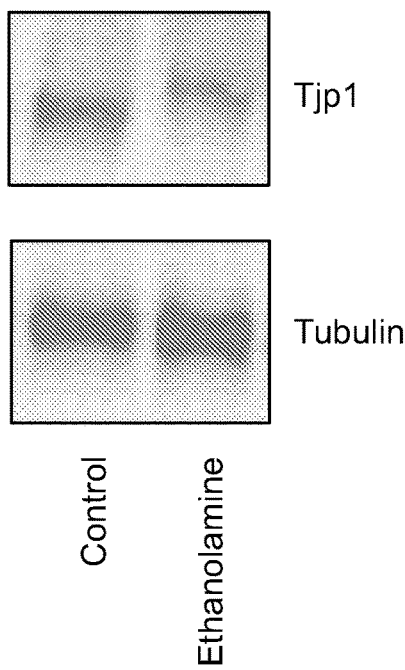
FIG. 2I shows that oral administration of ethanolamine (100 mg/kg body weight, one dose) in mice significantly reduced expression of protein in the ileum compared to non-treated controls. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 2J:
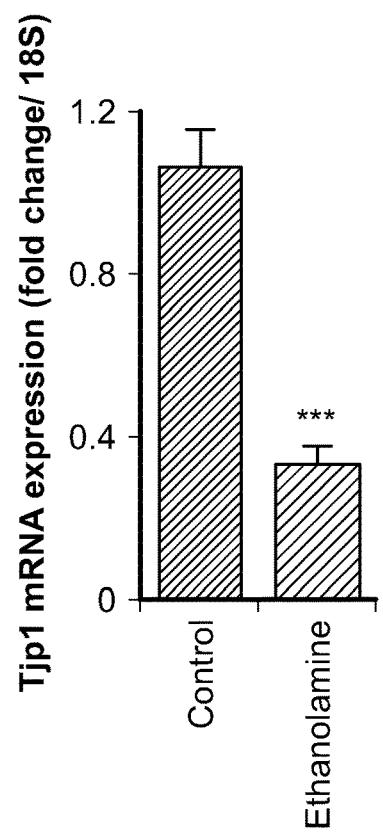
FIG. 2J shows that oral administration of ethanolamine (100 mg/kg body weight, one dose) in mice significantly reduced expression of mRNA in the colon compared to non-treated controls. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 2K:
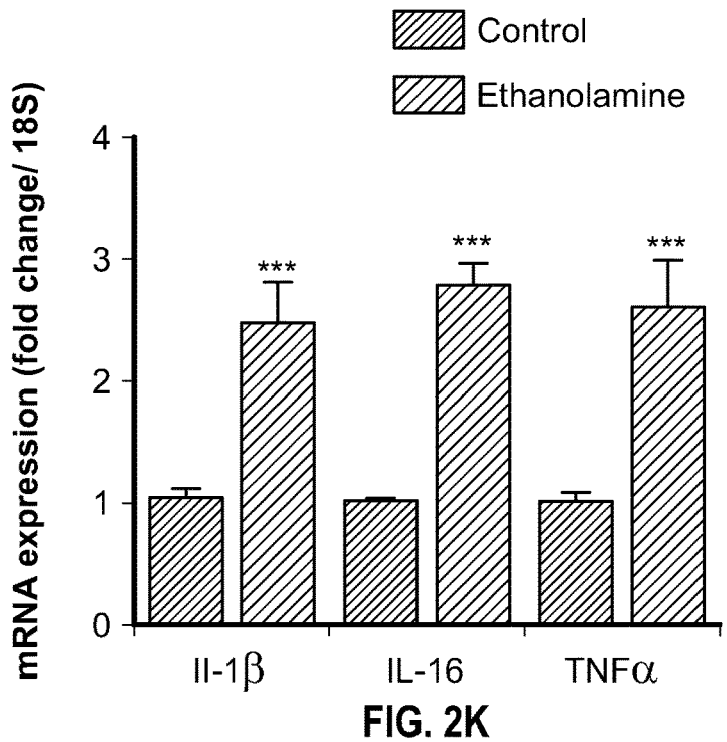
FIG. 2K shows that the ethanolamine treatment in mice also significantly increased the expression of inflammatory markers (IL-1 β, IL-6 and TNF α) in the intestine (ileum) compared to controls. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 12A:
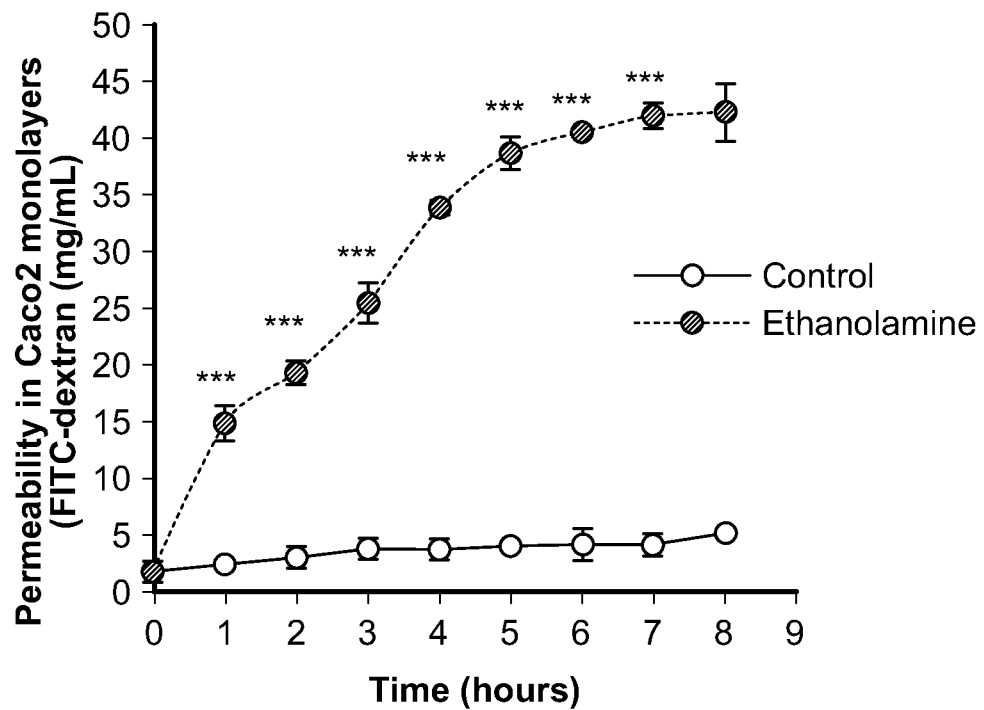
FIG. 12A shows that ethanolamine treatment significantly increased the diffusion of FITC dextran and reduced the TEER in the gut permeability assays in the monolayers of Caco2 cells over the time (up to 8 hrs). Values presented are mean of Caco2 culture experiments performed in triplicates and repeated 2-3 times, and error bars as standard error of means. P values with ***<0.001 are statistically significant.
Figure 12B:
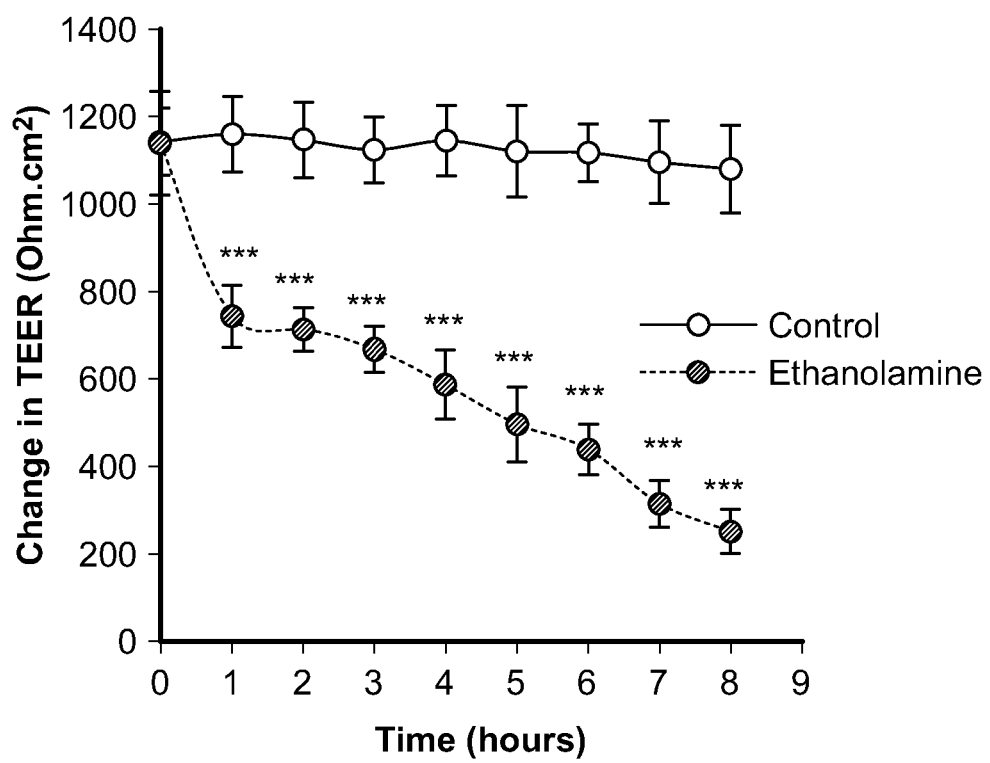
FIG. 12B shows that ethanolamine treatment reduced the TEER in the gut permeability assays in the monolayers of Caco2 cells over the time (up to 8 hrs). Values presented are mean of Caco2 culture experiments performed in triplicates and repeated 2-3 times, and error bars as standard error of means. P values with ***<0.001 are statistically significant.
Figure 12C:
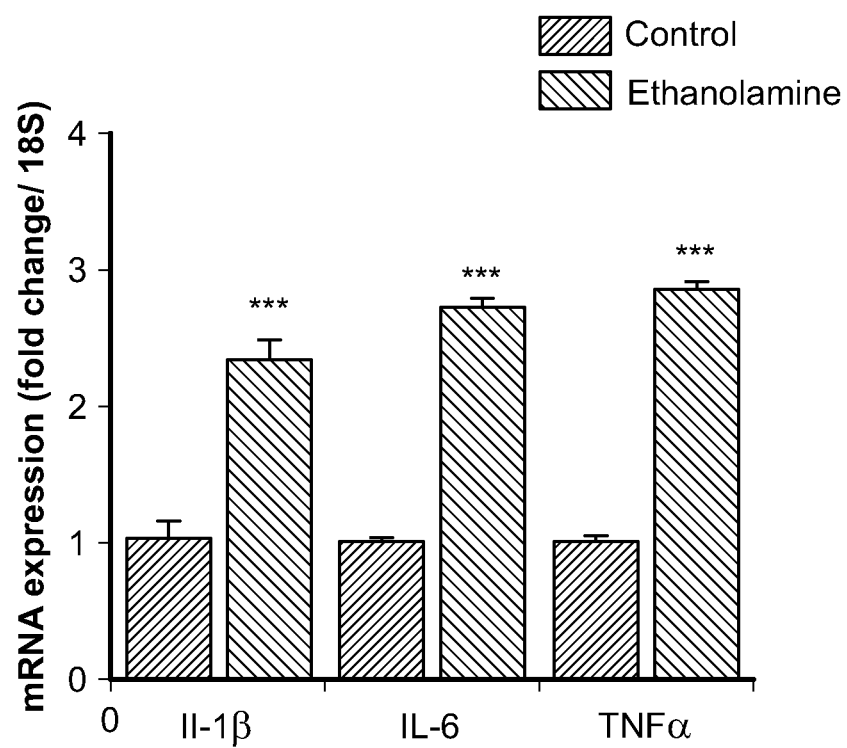
FIG. 12C shows that the ethanolamine treatment also significantly reduced the expression of inflammatory markers like IL-1, IL-6, and TNF-α. Values presented are mean of Caco2 culture experiments performed in triplicates and repeated 2-3 times, and error bars as standard error of means. P values with ***<0.001 are statistically significant.

Interestingly, among them, ethanolamine showed the highest reduction in the expression of Tjp1 in the enteroids and Caco2 cell monolayers (FIGS. 2C-2D), and significantly increased in the permeability of FITC-dextran and epithelial integrity (TEER) in Caco2 cell monolayers (FIGS. 2E-2F; FIGS. 12A-12B). Further, ethanolamine treatment to mice also significantly increased intestinal permeability, reduced expression of Tjp1, and increased inflammatory markers (FIGS. 2G-2K; FIG. 12C). These results indicated that obese/T2D accumulated higher ethanolamine which in turn reduced the expression of Tjp1 to weaken intestinal barrier functions, causing leaky gut and inflammation.

Figure 3A:
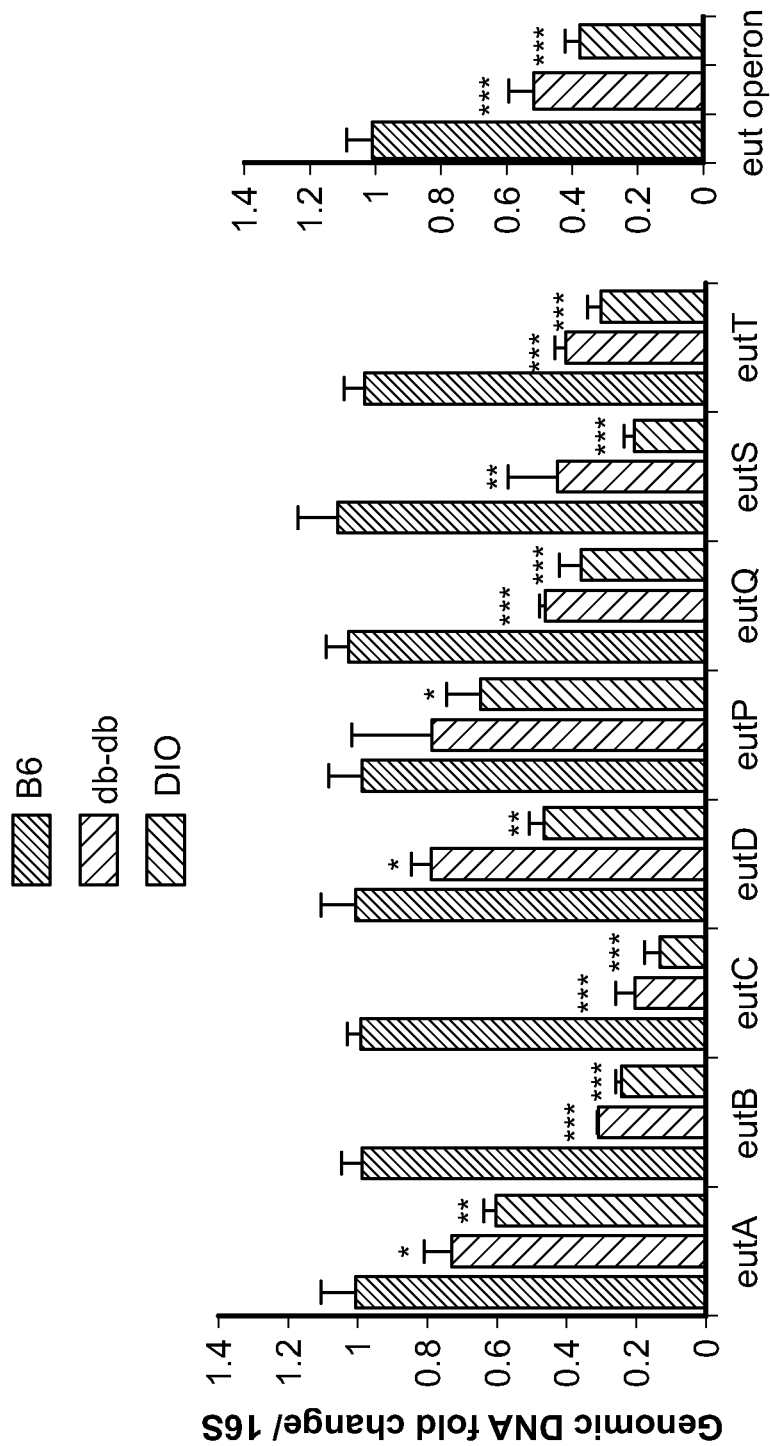
FIG. 3A shows that an ethanolamine abundance in the gut of obese mice and humans increases due to its under metabolization by microbiota. The expression of ethanolamine utilizing operon genes (eutA, eutB, eutC, eutD, eutP, eutQ, eutS, eutT and aggregate of all gene as eut operon) was significantly decreased in the feces of db/db and DIO mice compared to control (B6). Values presented are mean of n=6-8 mice and n=10 lean and n=10 obese subjects in each group and error bars are standard error of means. P values with *<0.05; <0.01 and *<0.001 are statistically significant.
Figure 3B:
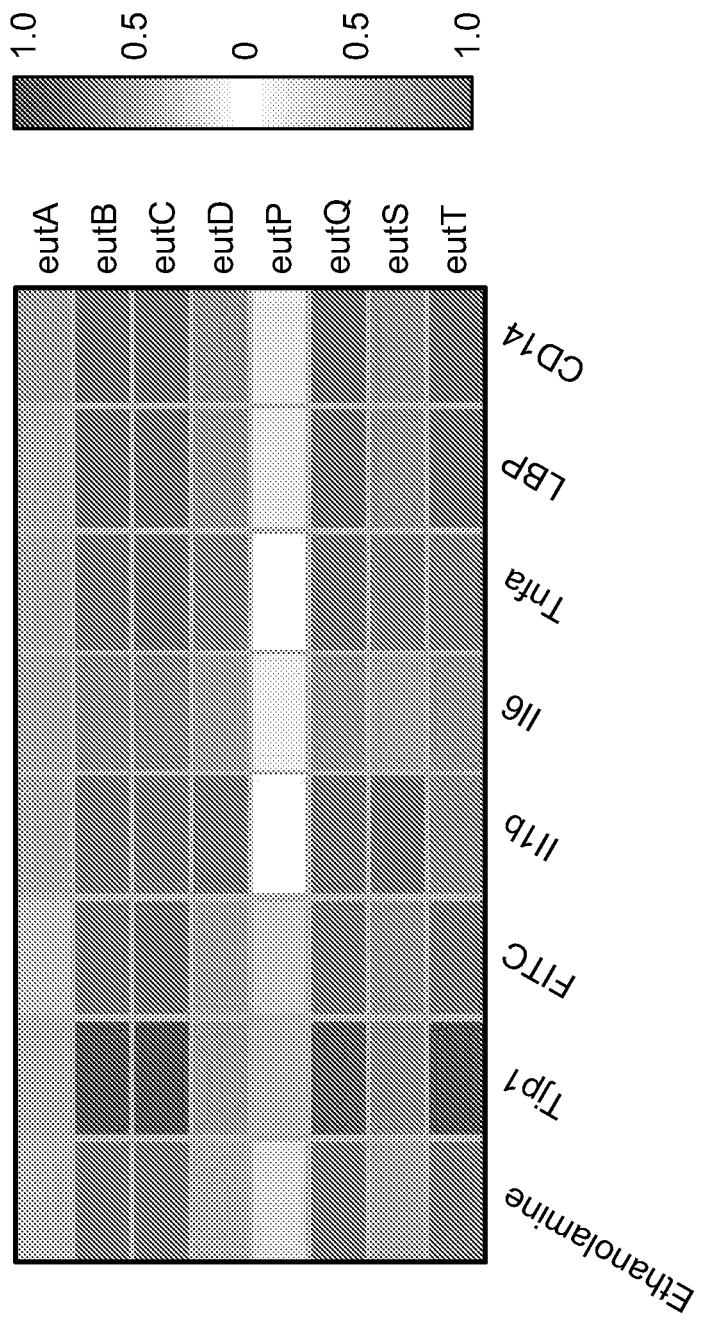
FIG. 3B shows that the reduced expression of these genes was negatively correlated with ethanolamine abundance, as well as markers of leaky gut (FITC-dextran leakiness, LBP and sCD14) and inflammatory markers (IL-1 β, IL-6 and TNF-α) and positively correlated with the expression of Tjp1 in the mice intestine. Values presented are mean of n=6-8 mice and n=10 lean and n=10 obese subjects in each group and error bars are standard error of means. P values with *<0.05; <0.01 and *<0.001 are statistically significant.
Figure 3C:
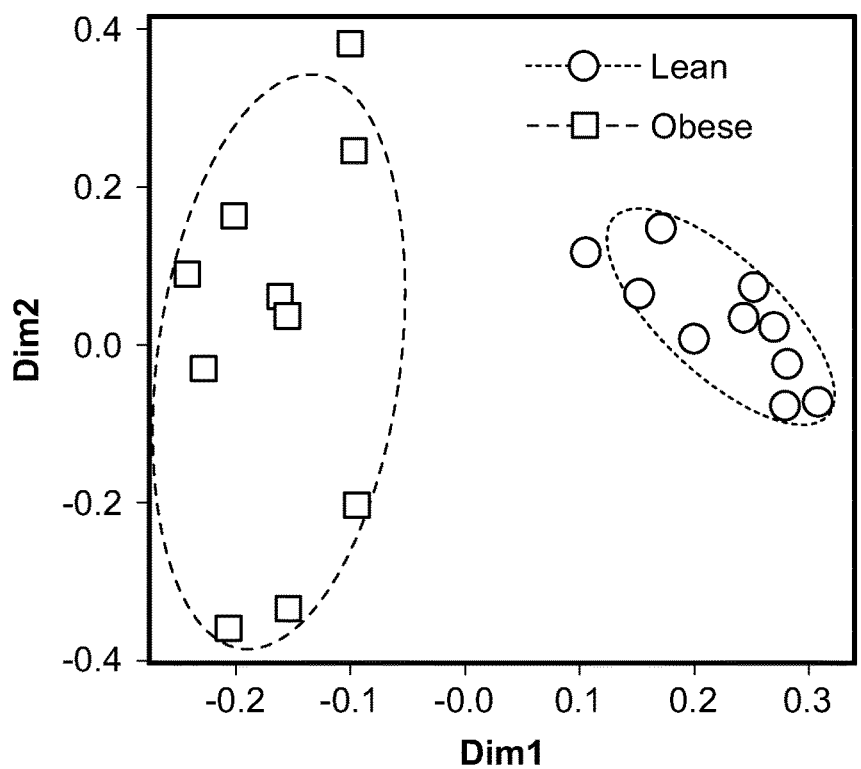
FIG. 3C shows PCA analyses (FIG. 3C) which show that metabolite signature was significantly different in 10 lean compared 10 obese subjects. Values presented are mean of n=6-8 mice and n=10 lean and n=10 obese subjects in each group and error bars are standard error of means. PCA shows individual sample values. P values with *<0.05; <0.01 and *<0.001 are statistically significant.
Figure 3D:
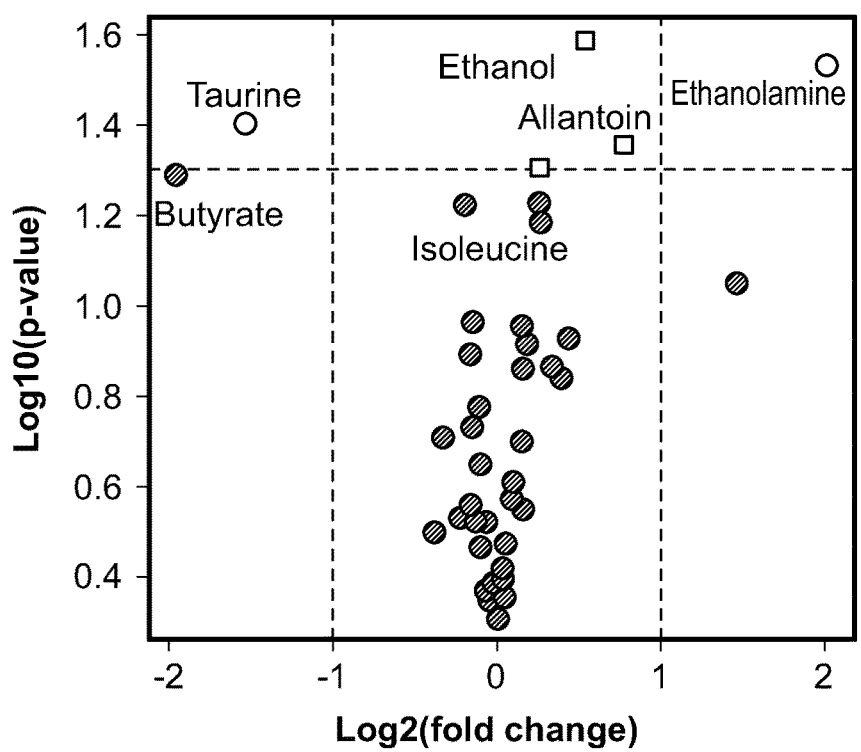
FIG. 3D shows differential abundance analyses in volcano graph which shows that ethanolamine abundance was significantly higher in the gut of obese compared to lean subjects. Values presented are mean of n=6-8 mice and n=10 lean and n=10 obese subjects in each group and error bars are standard error of means. Volcano shows individual sample values. P values with *<0.05; <0.01 and *<0.001 are statistically significant.
Figure 3E:
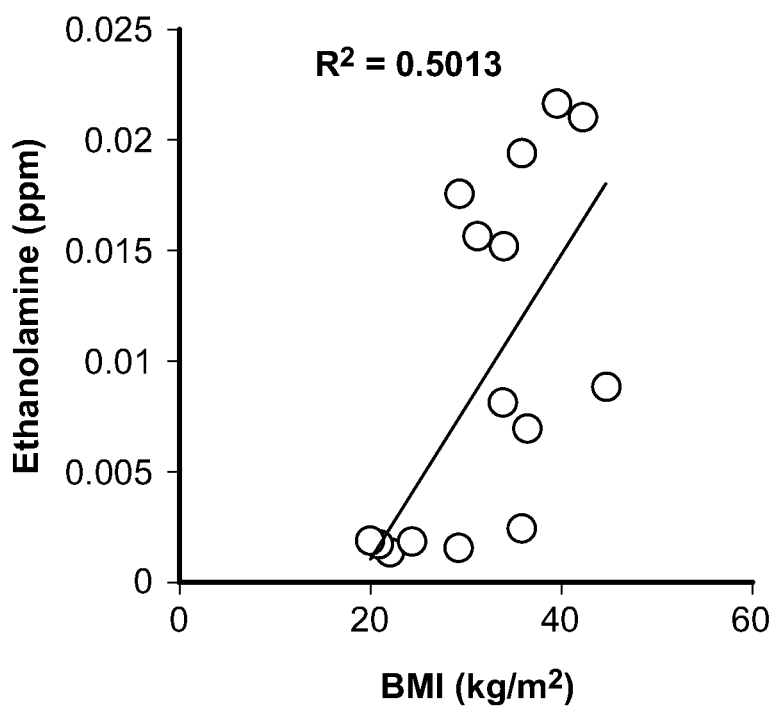
FIG. 3E shows that increased ethanolamine abundance shows strong positive correlation. Values presented are mean of n=6-8 mice and n=10 lean and n=10 obese subjects in each group and error bars are standard error of means. Correlation analyses show individual sample values. P values with *<0.05; <0.01 and *<0.001 are statistically significant.
Figure 3F:
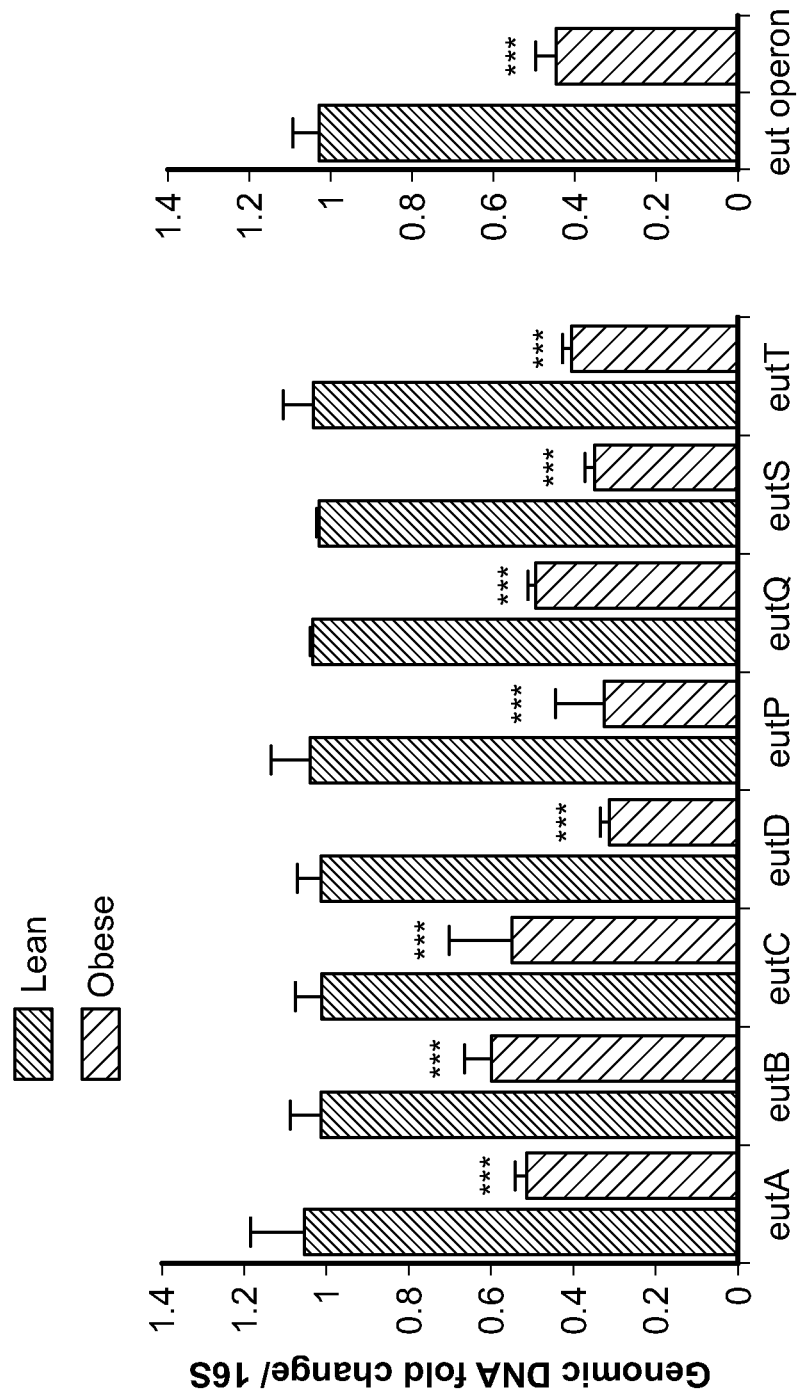
FIG. 3F shows increased ethanolamine abundance shows reduced ethanolamine utilizing operon genes. Values presented are mean of n=6-8 mice and n=10 lean and n=10 obese subjects in each group and error bars are standard error of means. P values with *<0.05; <0.01 and *<0.001 are statistically significant.
Figure 3G:
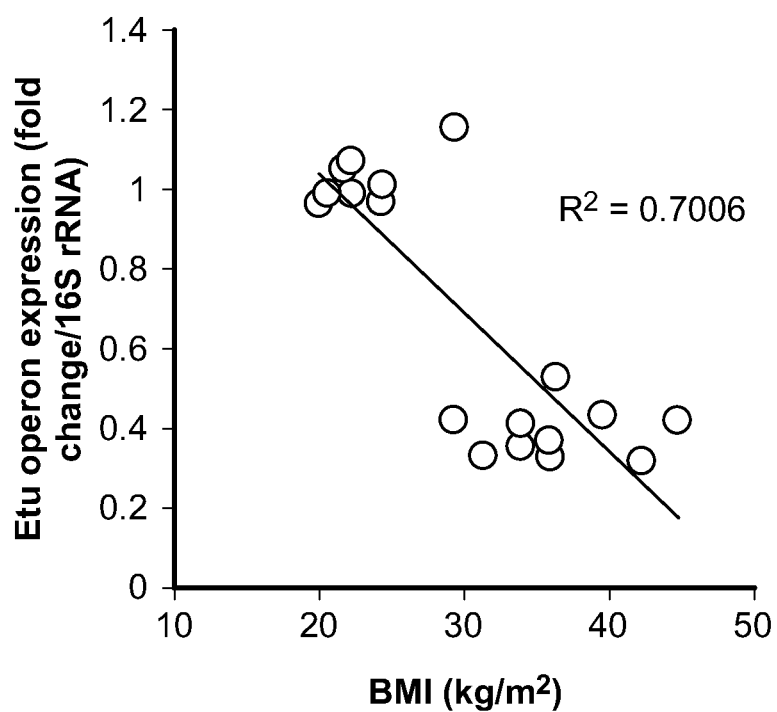
FIG. 3G shows a negative correlation with BMI in human subjects. Values presented are mean of n=6-8 mice and n=10 lean and n=10 obese subjects in each group and error bars are standard error of means. Correlation analyses show individual sample values. P values with *<0.05; <0.01 and *<0.001 are statistically significant.
Figure 13A:
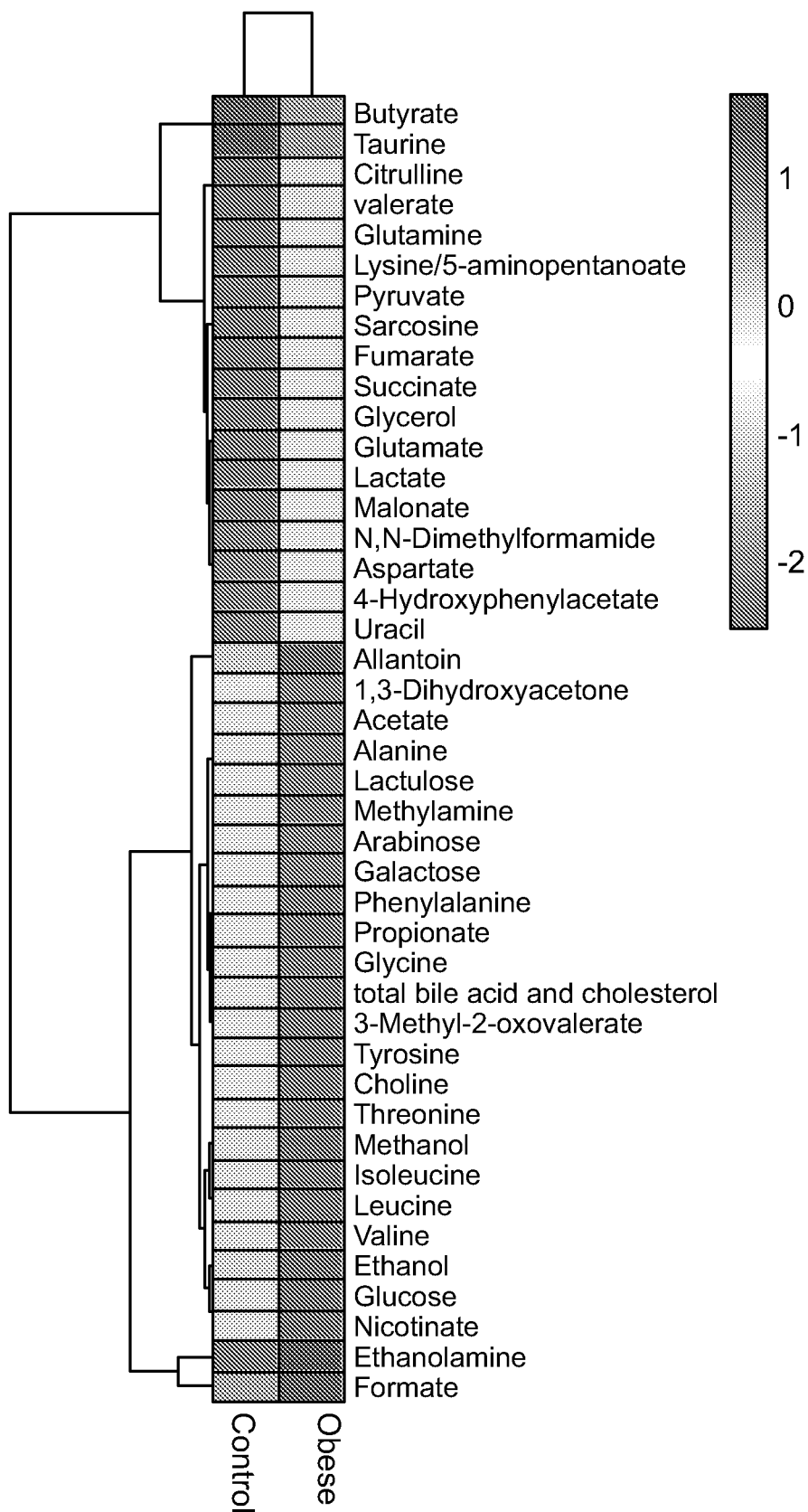
FIG. 13A shows a heatmap depicting the metabolites in lean controls versus obese human subjects.
Figures 13B, 13C:
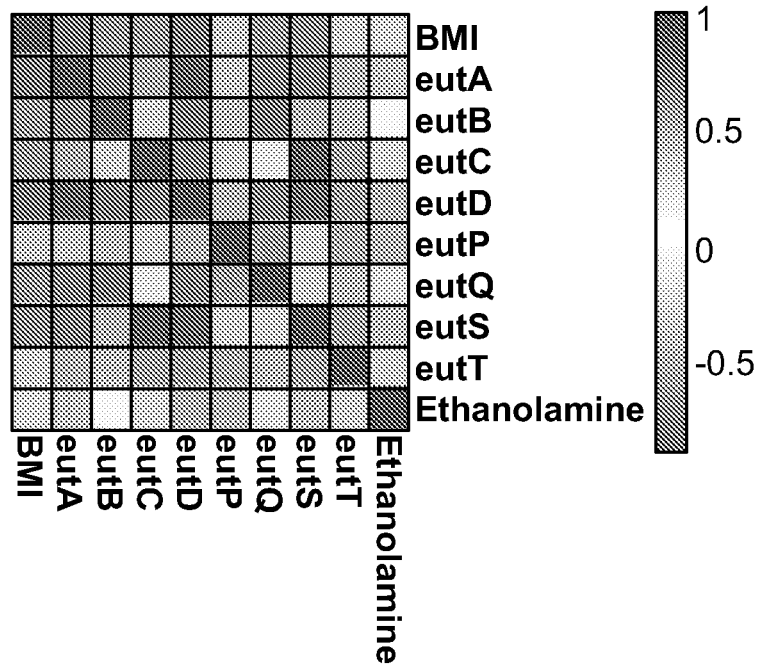
FIG. 13B shows demographics of human subjects from whom fecal samples were collected.
FIG. 13C shows a correlation heatmap between ethanolamine and ethanolamine utilizing operon genes in human fecal samples.

Ethanolamine was increased in obese/T2D gut due to decreased ethanolamine metabolizing bacteria. This example showed that obese/T2D gut has higher ethanolamine, which promotes leaky gut by reducing Tjp1. The abundance of bacteria expressing ethanolamine, utilizing ("metabolizing") (Eut) operon genes (i.e., eutA, eutB, eutC, eutD, eutP, eutQ, eutS and eutT) was significantly lower in the stools of obese/T2D mice compared to their controls (FIG. 3A); which was negatively correlated with ethanolamine, and markers of leaky gut and inflammation, and positively correlated with mRNA levels Tjp1 in db/db and DIO mice (FIG. 3B). As expected, our non-targeted metabolomics analyses showed that lean and obese humans' gut had significantly distinct metabolite signatures (FIG. 3C); and interestingly, the abundance of ethanolamine was significantly higher in the gut of obese subjects compared to lean (FIG. 3D; FIG. 13A), which was positively correlated with body mass index (BMI; FIG. 3E). In addition, Eut operon expression was also lower in the stools of obese subjects than lean subjects (FIG. 3F), which was negatively correlated with BMI (FIG. 3G; FIG. 13C). These results suggested that the microbiota in obese/T2D gut has reduced abundance of ethanolamine metabolizing bacteria, leading to higher ethanolamine accumulation. These found phenotypes were similar in mice and humans, showing clinically important promise.

Figure 4A:
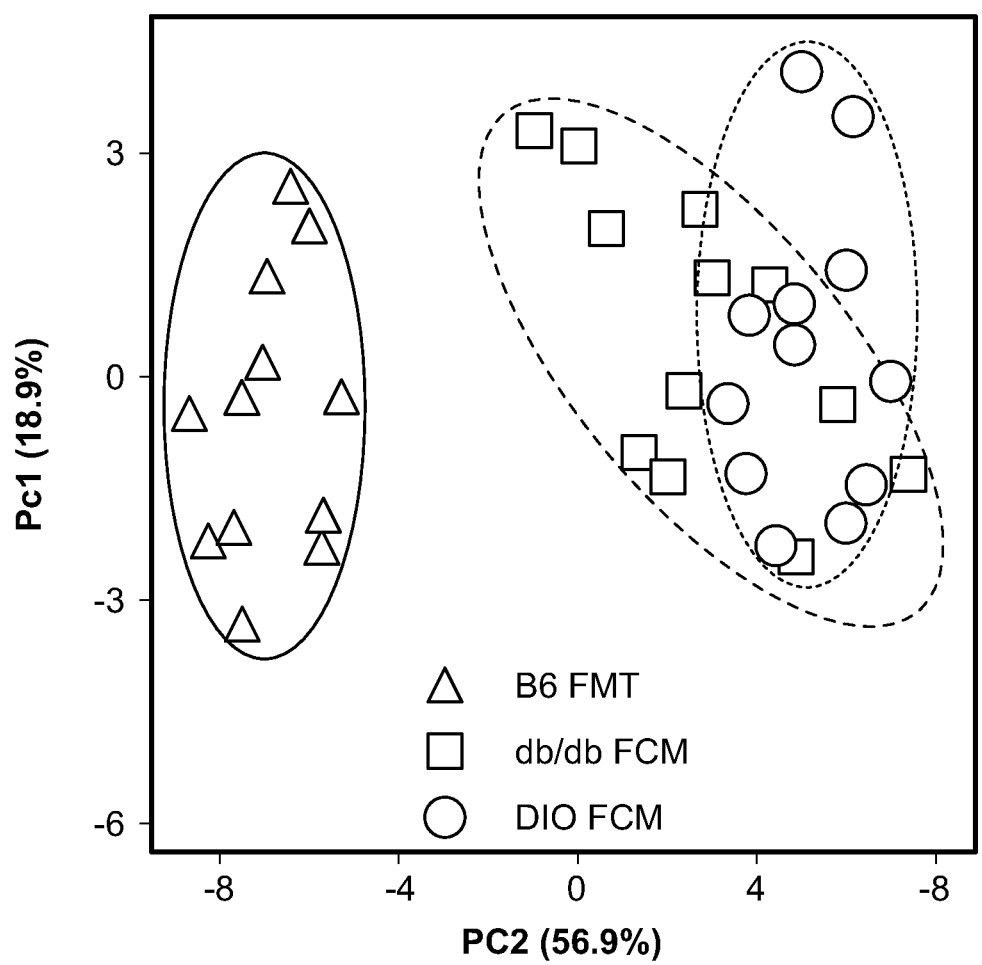
FIG. 4A shows that ethanolamine and obese microbiota enhance expression of miR101a-3p, which in turn induces leaky gut by reducing Tjp1 expression. PCA graph of global miRNA profiles from enteroids treated with FCMs of db/db and DIO show significantly distinct miRNA expression profiles compared to controls. Values presented are mean of n=6-8 mice in each group and error bars are standard error of means. PCA (a), and random forest analyses (b) show individual sample values. P values with *<0.05; <0.01 and *<0.001 are statistically significant.
Figure 4B:
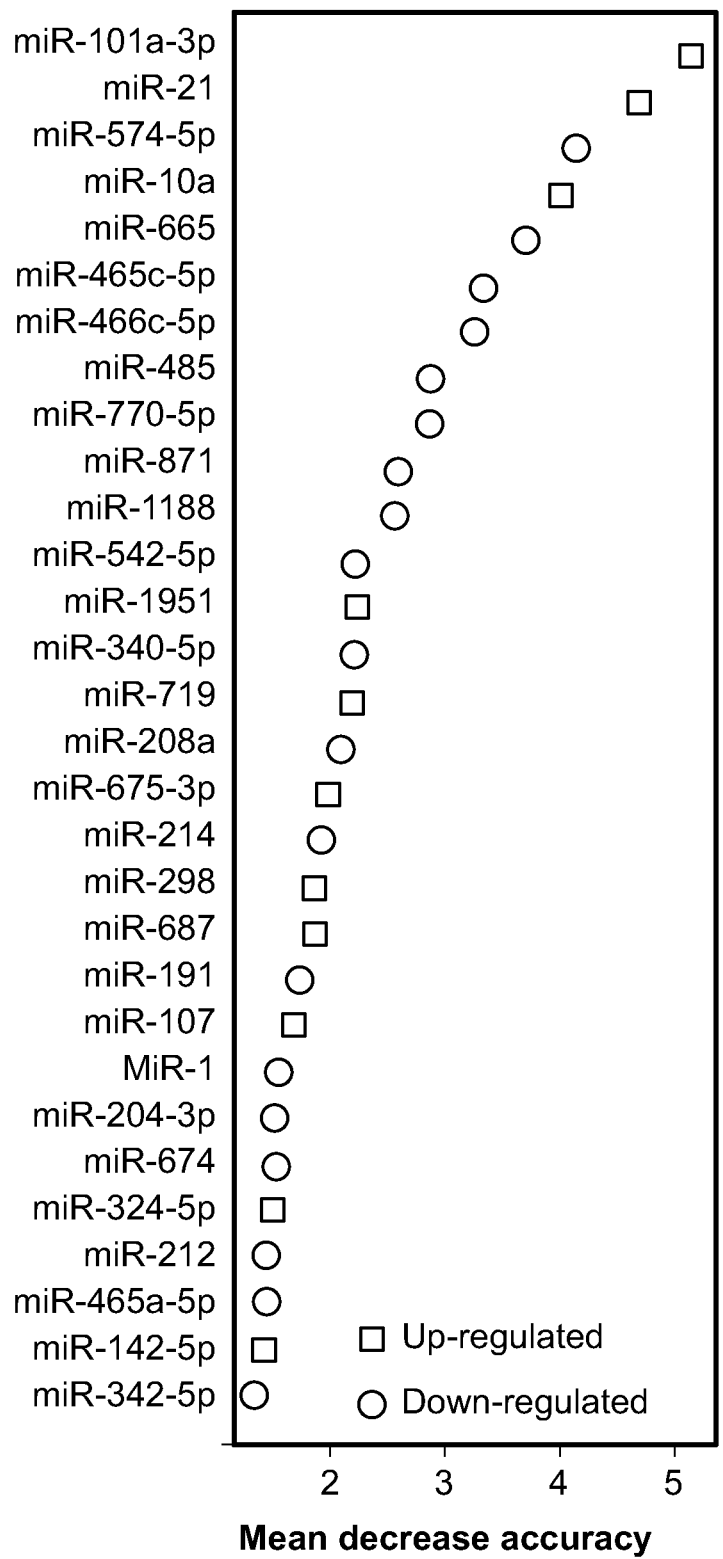
FIG. 4B shows that Random Forest analyses of miRNA data revealed that miR101a-3p expression was significantly increased enteroids treated with FCMs of db/db and DIO mice compared to B6 controls. Values presented are mean of n=6-8 mice in each group and error bars are standard error of means. PCA (a), and random forest analyses (b) show individual sample values. P values with *<0.05; <0.01 and *<0.001 are statistically significant.
Figure 4K:
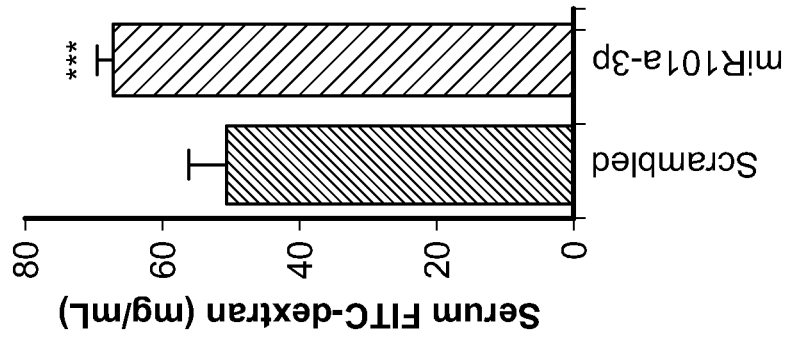
FIG. 4K shows that an enema of lentivirus expressing miR101a-3p mimetic significantly increased FITC-dextran in serum in the mice gut compared to the scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 4L:
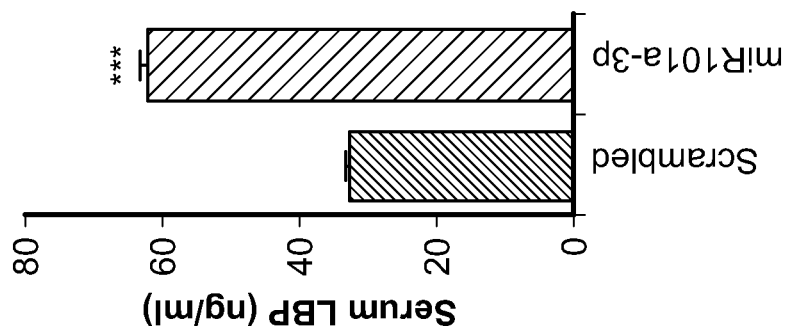
FIG. 4L shows that an enema of lentivirus expressing miR101a-3p mimetic significantly increased LBP in serum in the mice gut compared to the scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 4M:
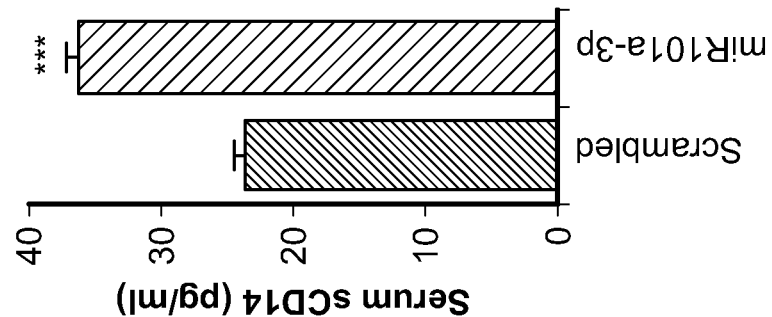
FIG. 4M shows that an enema of lentivirus expressing miR101a-3p mimetic significantly increased sCD14 in serum in the mice gut compared to the scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 4N:
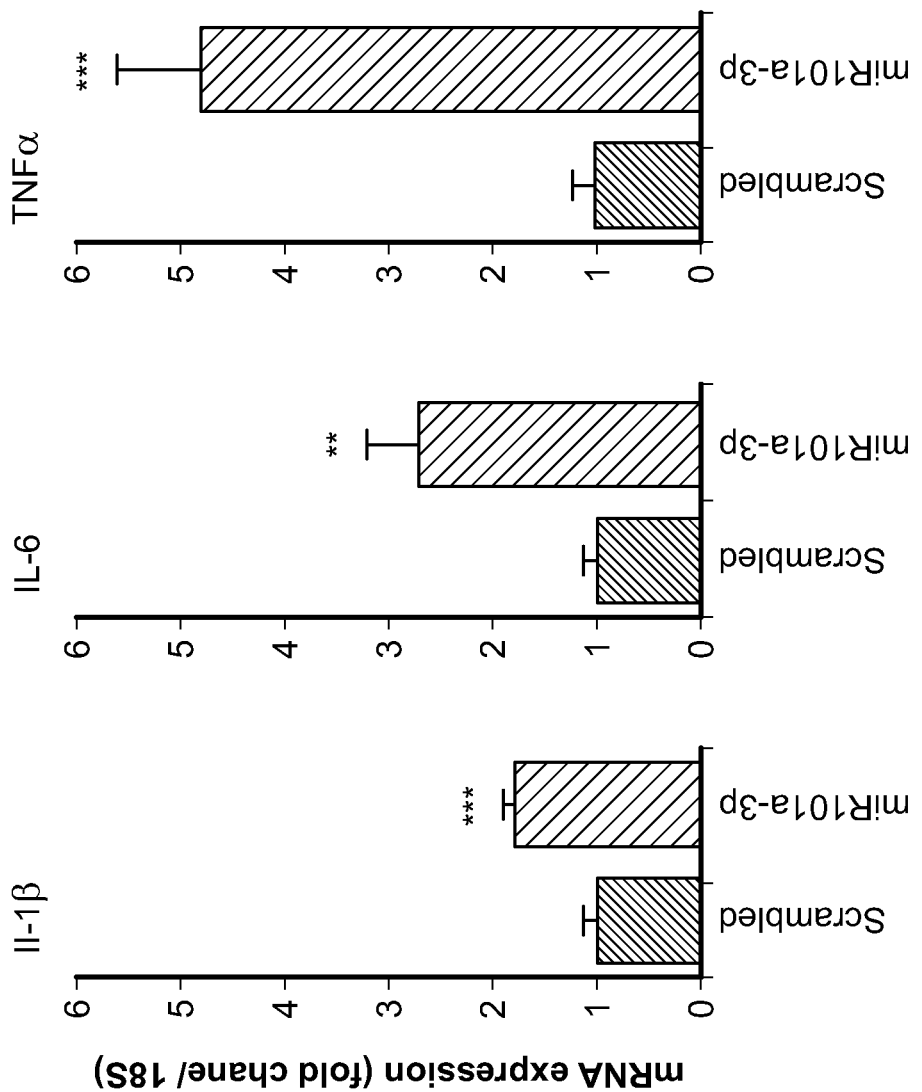
FIG. 4N shows that an enema of lentivirus expressing miR101a-3p mimetic significantly increased inflammation (IL-β, IL-6 and TNF-α [FIG. 4N]) in the mice gut compared to the scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 4O:
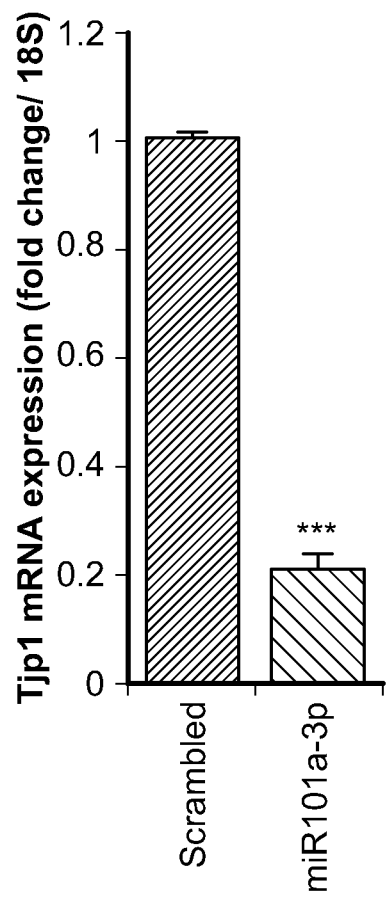
FIG. 4O shows that an enema of lentivirus expressing miR101a-3p mimetic significantly reduced mRNA in the mice gut compared to their scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 4P:
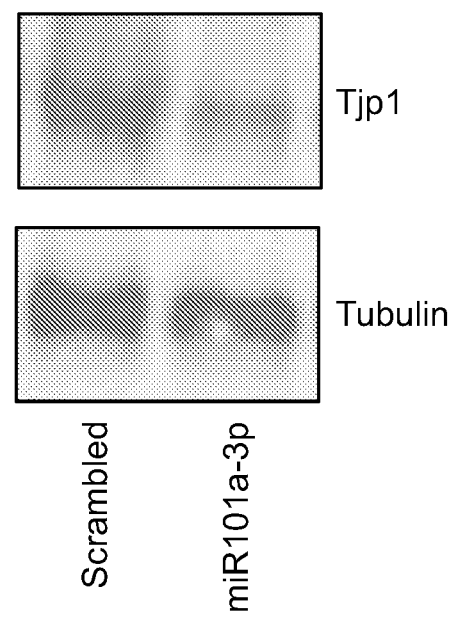
FIG. 4P shows that an enema of lentivirus expressing miR101a-3p mimetic significantly increased reduced protein of Tjp1 in the mice gut compared to the scrambled miR lentivirus infected mice. Values presented are mean of n=6-8 mice in each group and error bars are standard error of means. PCA (a), and random forest analyses (b) show individual sample values. P values with *<0.05; <0.01 and *<0.001 are statistically significant.
Figure 14A:
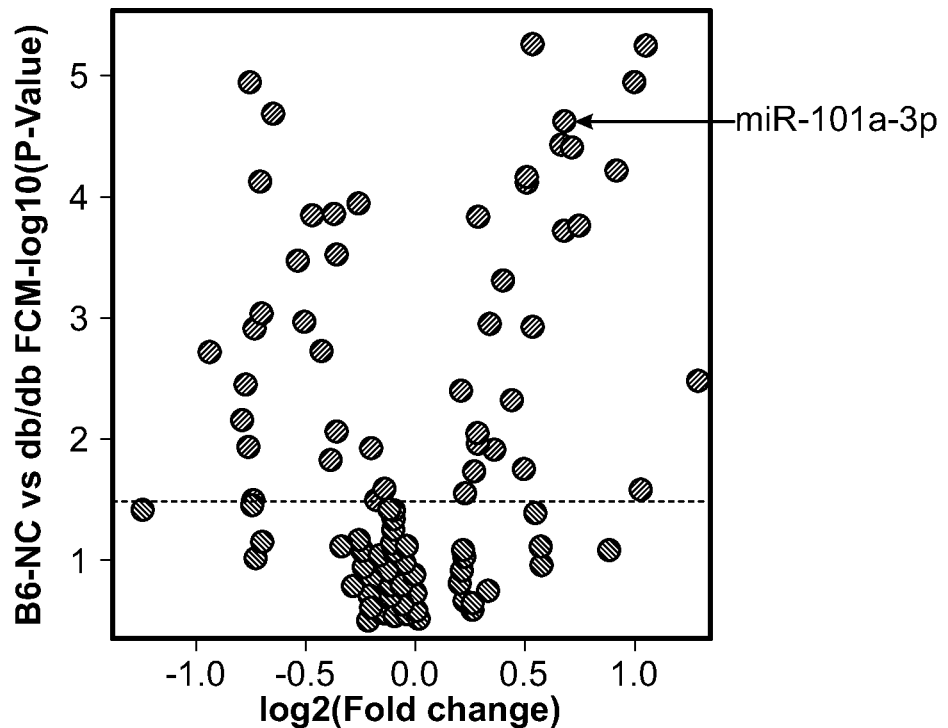
FIG. 14A shows the expression of miRNAs in the enteroids treated with FCMs of db/db compared to B6 control FCMs. Values presented are means of enteroid culture experiments performed in triplicates and repeated 2-3 times.
Figure 14B:
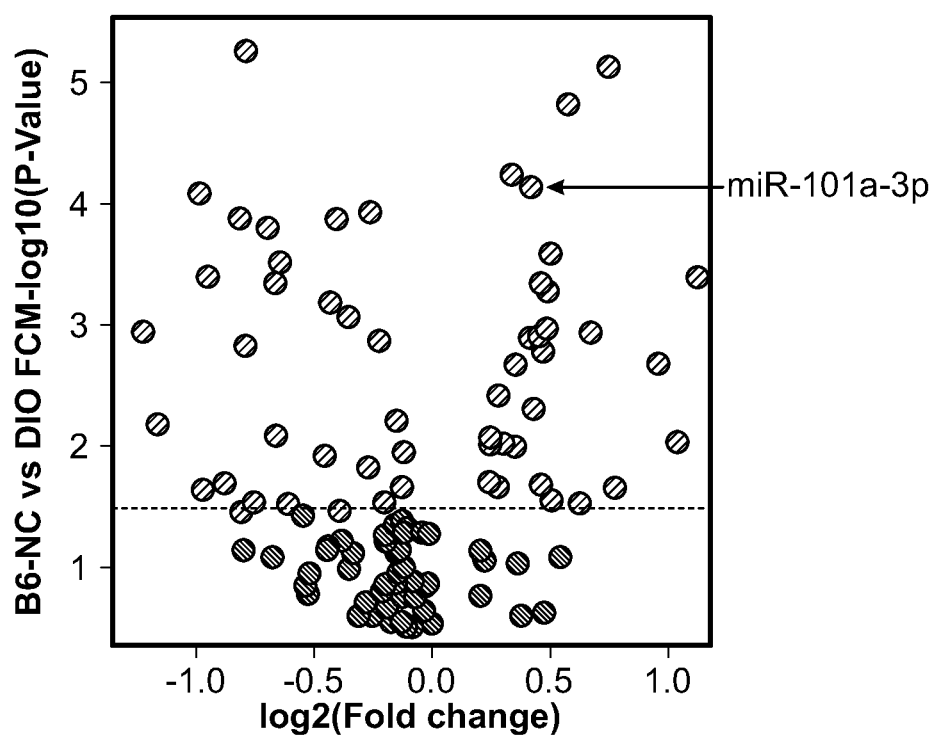
FIG. 14B shows the expression of miRNAs in the enteroids treated with FCMs of DIO compared to B6 control FCMs. Values presented are means of enteroid culture experiments performed in triplicates and repeated 2-3 times.
Figure 15A:
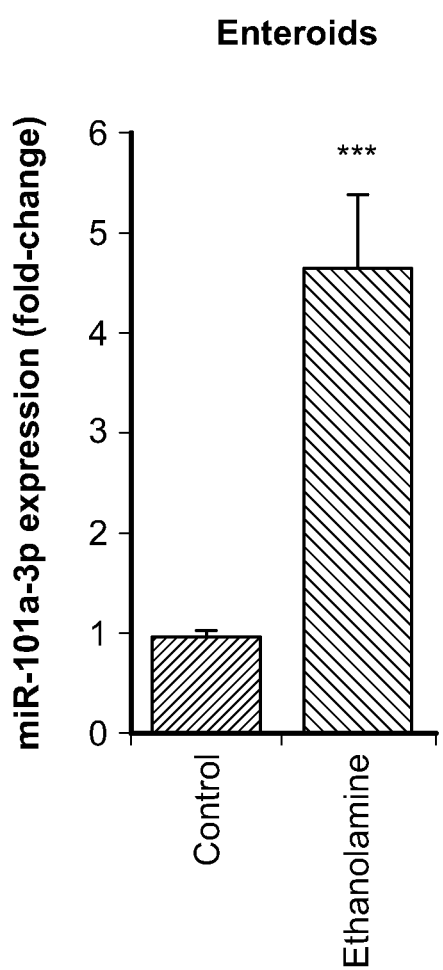
FIG. 15A shows that ethanolamine treatment in enteroids (FIG. 15A) significantly increased the expression of miR101a-3p. Values presented are mean of enteroids and Caco2 culture experiments performed in triplicates and repeated 2-3 times, and error bars as standard error of means. P values with ***<0.001 are statistically significant.
Figure 15B:
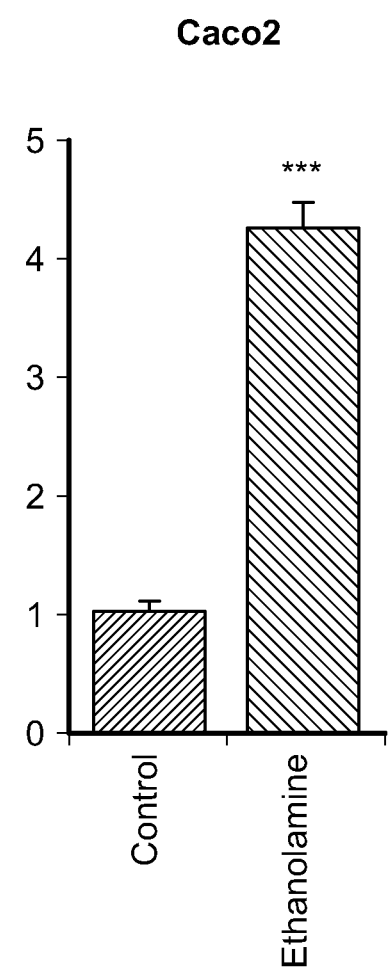
FIG. 15B shows that ethanolamine treatment in Caco2 cells (FIG. 15B) significantly increased the expression of miR101a-3p. Values presented are mean of enteroids and Caco2 culture experiments performed in triplicates and repeated 2-3 times, and error bars as standard error of means. P values with ***<0.001 are statistically significant.
Figures 16A, 16B:
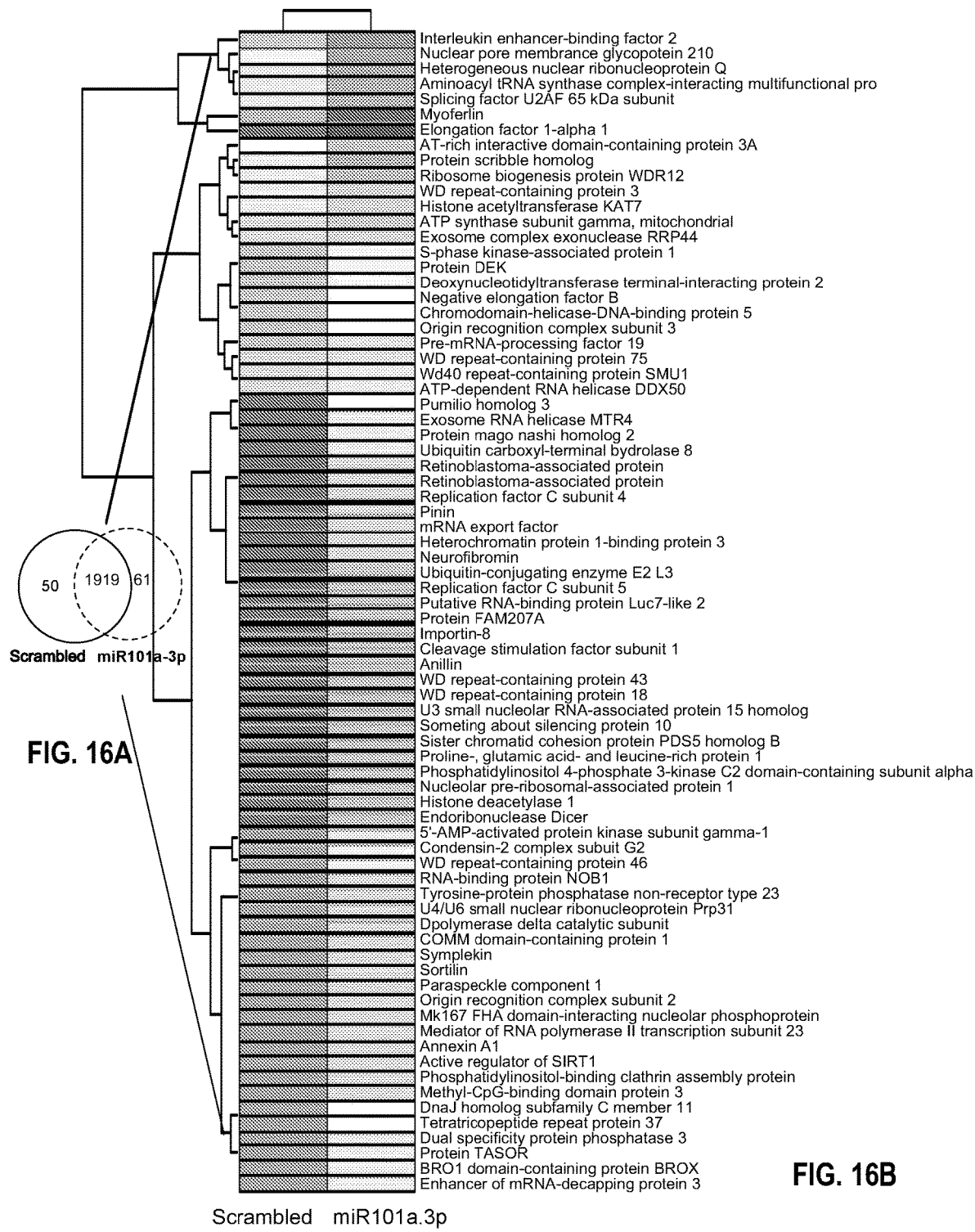
FIG. 16A shows the number of proteins detected in the global proteomics analyses pulled down in miR101a-3p promoter transfected cells compared to scrambled transfected cells.
FIG. 16B shows the abundance of proteins detected in the global proteomics analyses in fold change in heat map.
Figure 18A:
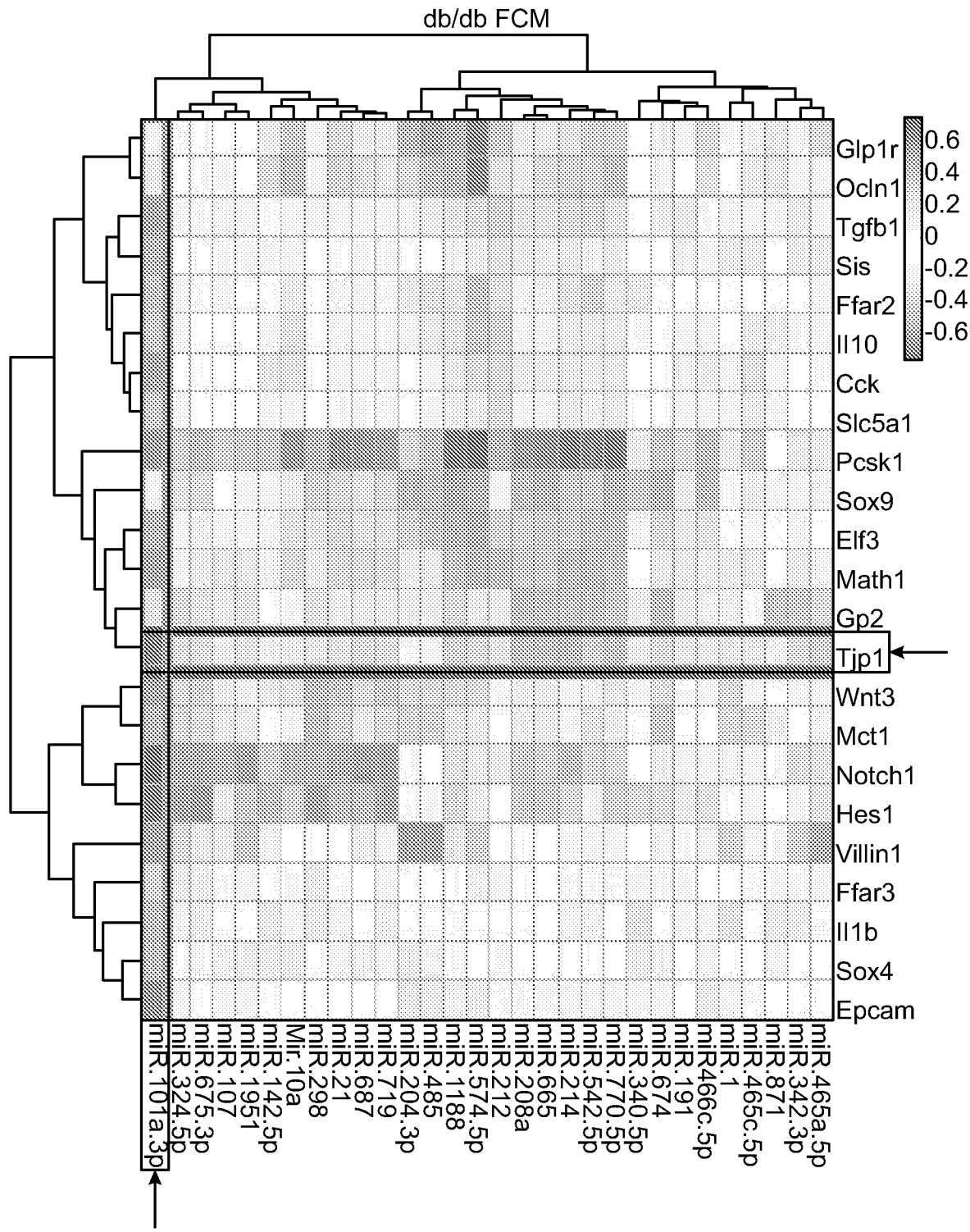
FIG. 18A shows a Correlation heatmap of expression of intestinal epithelia specific genes and top miRNA in enteroids treated with FCMs of db/db than control B6 FCM. Values presented are mean (n=6-8 mice per group) and error bars as standard error of means. Enteroids and Caco2 culture experiments were performed in triplicates and repeated 2-3 times. P values with ***<0.001 are statistically significant.
Figure 18B:
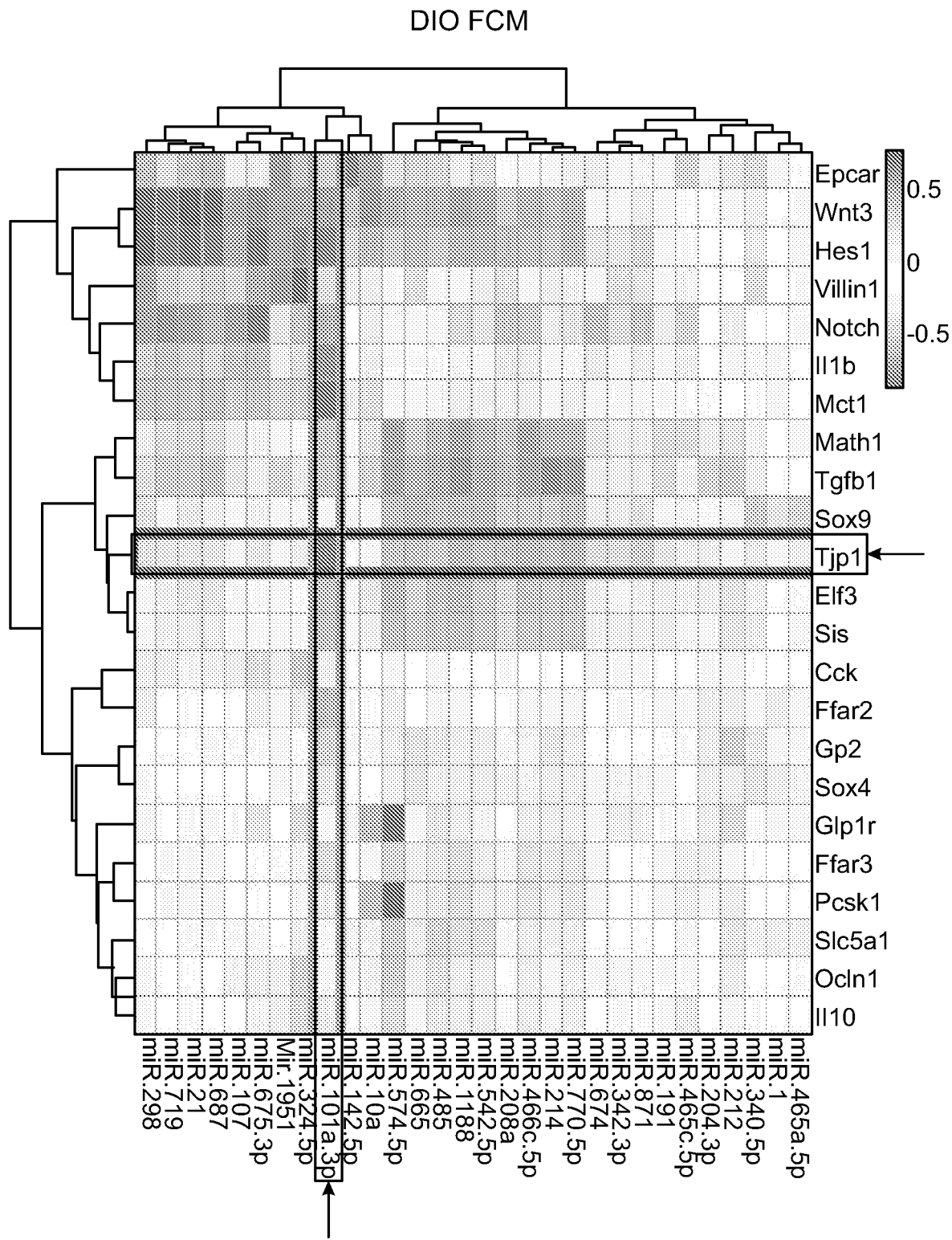
FIG. 18B shows a Correlation heatmap of expression of intestinal epithelia specific genes and top miRNA in enteroids treated with FCMs of DIO feces than control B6 FCM. Values presented are mean (n=6-8 mice per group) and error bars as standard error of means. Enteroids and Caco2 culture experiments were performed in triplicates and repeated 2-3 times. P values with ***<0.001 are statistically significant.
Figure 18C:
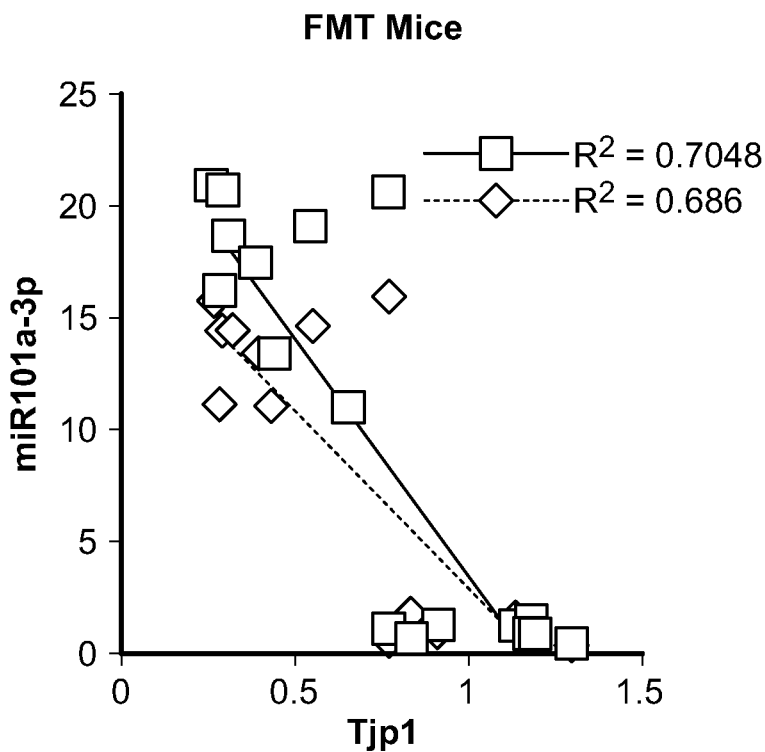
FIG. 18C shows a Correlation analyses between Tjp1 with miR101a-3p expression in intestines of FMT recipients. Values presented are mean (n=6-8 mice per group) and error bars as standard error of means. Enteroids and Caco2 culture experiments were performed in triplicates and repeated 2-3 times. P values with ***<0.001 are statistically significant.
Figure 18D:
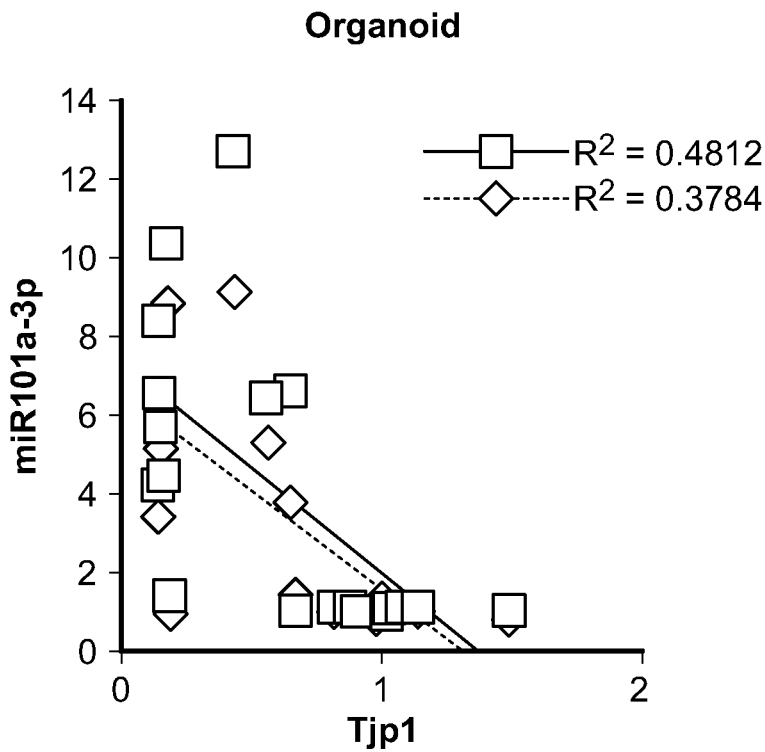
FIG. 18D shows a Correlation analyses between Tjp1 with miR101a-3p expression in FCM treated enteroids versus controls. Values presented are mean (n=6-8 mice per group) and error bars as standard error of means. Enteroids and Caco2 culture experiments were performed in triplicates and repeated 2-3 times. P values with ***<0.001 are statistically significant.
Figure 18E:
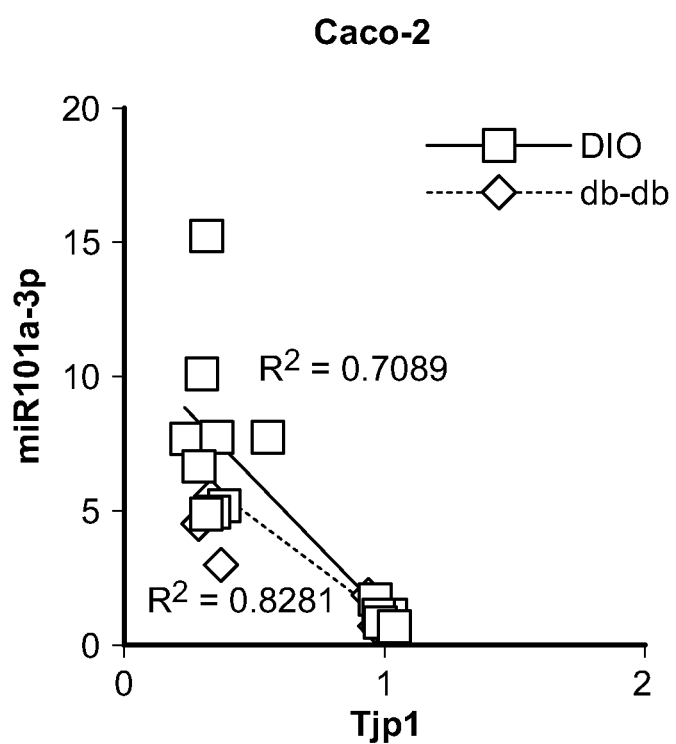
FIG. 18E shows a Correlation analyses between Tjp1 with miR101a-3p expression in Caco2 cells versus controls. Values presented are mean (n=6-8 mice per group) and error bars as standard error of means. Enteroids and Caco2 culture experiments were performed in triplicates and repeated 2-3 times. P values with ***<0.001 are statistically significant.

Obese/T2D microbiota and ethanolamine promoted leaky gut by elevating miR101a-3p expression in the gut. To further determine how obese/T2D microbiota induced ethanolamine reduces Tjp1 and cause leaky gut, a hypothesis that microbiota and its metabolite-ethanolamine modulate epigenetic factors like miRNAs induce leaky gut was tested. Our unbiased, global miRNA expression analyses revealed that the enteroids treated with DIO and db/db FCMs show significantly distinct miRNA signatures compared to their controls (FIG. 4A). Further, random forest analyses revealed that the expression of miR101a-3p was highest in enteroids treated with obese/T2D FCMs compared to controls (FIG. 4B; FIGS. 14A-14B), a result confirmed by real-time PCR analyses in FCM treated enteroids and Caco2 cells (FIGS. 4C-4D). The expression of miR101a-3p was also significantly higher in ileum and colon of fecal donor db/db and DIO and their FMT recipient mice, compared to their controls (FIGS. 4E, 4H). Intriguingly, ethanolamine treatment also increased the expression of miR101a-3p expression in mouse intestine as well as in enteroids and Caco2 cell monolayers (FIGS. 4I, 4J; FIGS. 15A-15B), suggesting that the obese/T2D microbiota and ethanolamine induced the expression of miR101a-3p in gut epithelial cells. Further, the enema of miR101a-3p expressing lentivirus in mice also significantly increased leaky gut and inflammation along with reduced expression of Tjp1 in the intestine compared to scrambled lentivirus treated controls (FIGS. 4K-4P). Overall, these results demonstrated that the obese/T2D microbiota mediated elevated ethanolamine promoted expression of miR101a-3p in gut epithelial cells, which induces leaky gut.

Figures 5G, 5H, 5I:
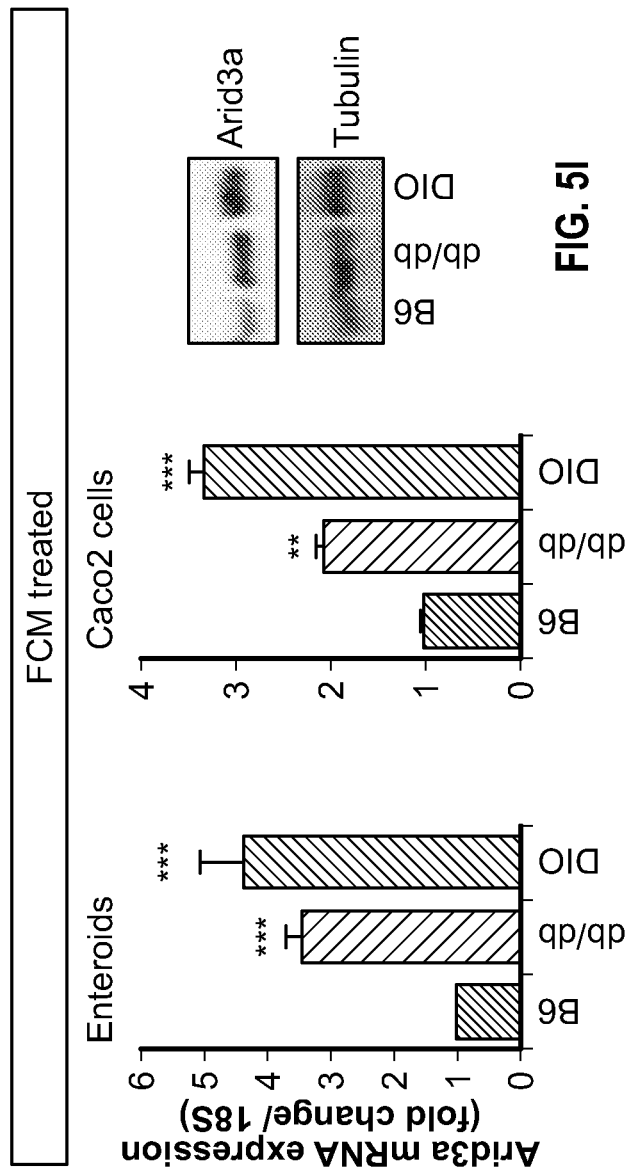
FIG. 5G shows that obese/T2D FCMs treatments significantly increased the expression of Arid3a in the enteroids.
FIG. 5H shows that obese/T2D FCMs treatment significantly increased the expression of Caco2 cells compared to controls.
FIG. 5I shows that obese/T2D FCMs treatments significantly increased the expression of Caco2 cells compared to controls.

Ethanolamine elevated miR101a-3p expression by activating its promoter activity. Ethanolamine treatment significantly increased the promoter luciferase activity of miR101a-3p in Caco2 cells (FIG. 5A), which suggested that ethanolamine increases miR101a-3p by activating its promoter. To further demonstrate which DNA region(s) of miR101a-3p promoter (2000 bp long) (Huang et al., 2017) contributes in ethanolamine induced activation, cells transfected with vector containing sequence of −1 to −1000 bp region exhibited the highest luciferase activity upon ethanolamine treatment, but moderate and no effects in cells transfected with −1 to −1500 bp and −1 to 500 bp fragments, respectively (FIG. 5B). These results indicated that the promoter region between −1 to −500 does not participates in ethanolamine mediated activation of miR101a-3p promoter while fragment −1 to −1000 and −1 to −1500 show the highest to moderate activation. Thus −500 to −1000 bp fragment participates in ethanolamine-induced activation of this promoter.

Figures 5O, 5P:
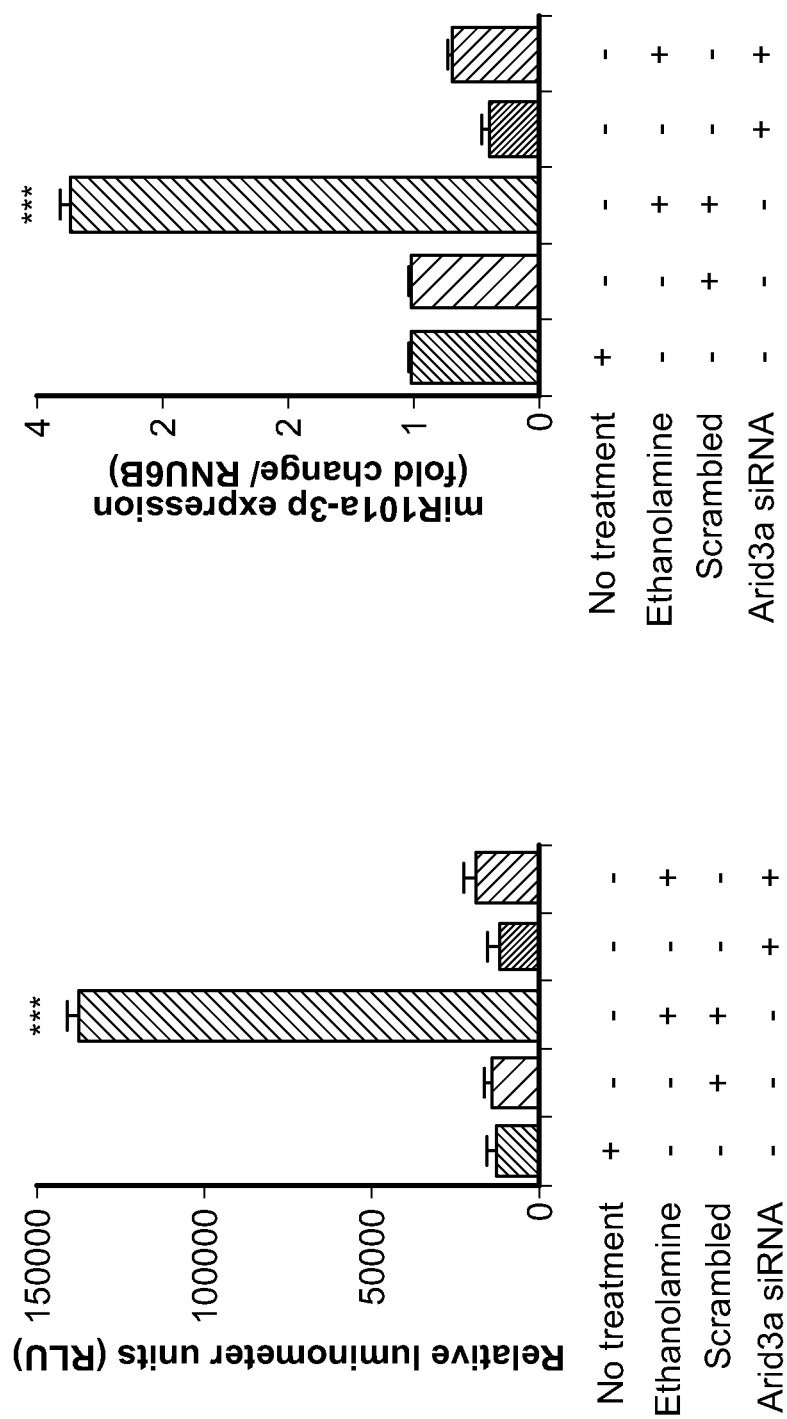
FIG. 5O shows that ethanolamine mediated activation of miR101a-3p promoter activity was abolished in ARID3a siRNA transfected Caco2 cells compared to scrambled siRNA transfected cells. Values presented are mean of n=6-8 mice and n=2-3 repeated triplicate enteroids and Caco2 culture experiments in each group and error bars are standard error of means. P values with *<0.05; <0.01 and *<0.001 are statistically significant.
FIG. 5P shows that miR101a-3p expression was abolished in ARID3a siRNA transfected Caco2 cells compared to scrambled siRNA transfected cells. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 5Q:
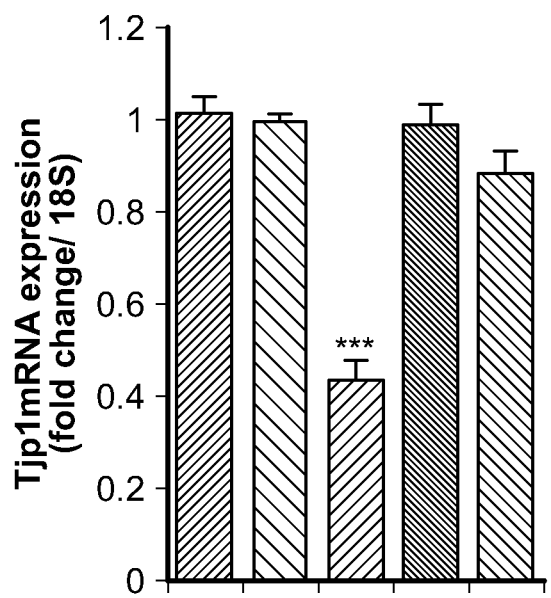
FIG. 5Q shows that suppression in Tjp1 expression was abolished in ARID3a siRNA transfected Caco2 cells compared to scrambled siRNA transfected cells. Values presented are mean of n=6-8 mice and n=2-3 repeated triplicate enteroids and Caco2 culture experiments in each group and error bars are standard error of means. P values with *<0.05; <0.01 and *<0.001 are statistically significant.
Figure 6A:
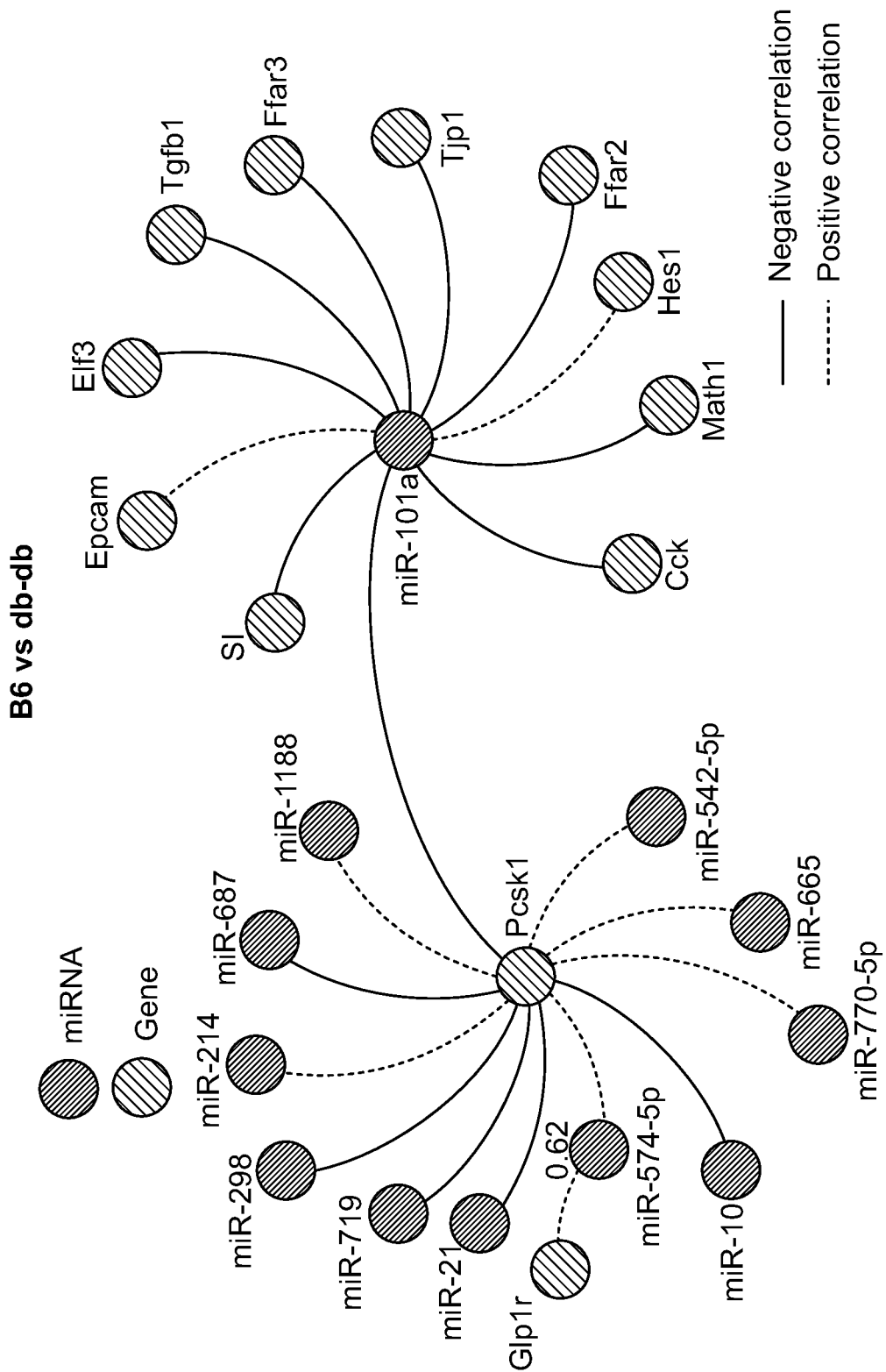
FIG. 6A shows that ethanolamine induced miR101a-3p which in turn reduced Tjp1 expression by decreasing its mRNA stability. Correlation networking analyses of miRNA and intestinal cell specific gene expression profiles in intestines from obese/T2D FMT recipient mice, and enteroids and Caco2 cells treated with obese/T2D FCMs show that miR101a-3p shows highest negative correlation. Values presented are mean of n=2-3 repeated triplicate of Caco2 culture experiments in each group and error bars are standard error of means. P values with *<0.05; <0.01 and *<0.001 are statistically significant.
Figure 6B:
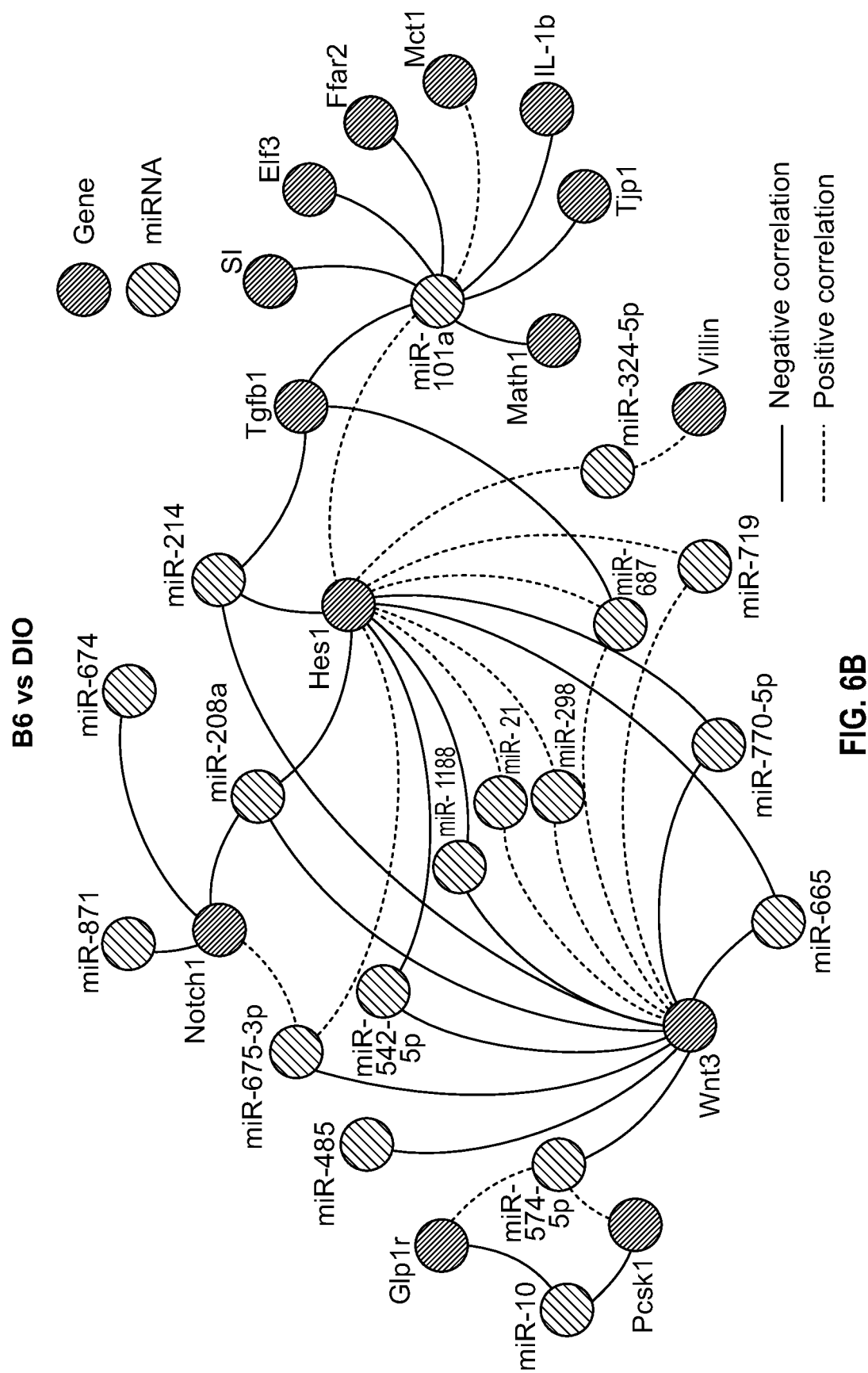
FIG. 6B shows correlation networking analyses of miRNA and intestinal cell specific gene expression profiles in intestines from obese/T2D FMT recipient mice, and enteroids and Caco2 cells treated with obese/T2D FCMs show that Tjp1 shows highest negative correlation. Values presented are mean of n=2-3 repeated triplicate of Caco2 culture experiments in each group and error bars are standard error of means. P values with *<0.05; <0.01 and *<0.001 are statistically significant.
Figure 6C:
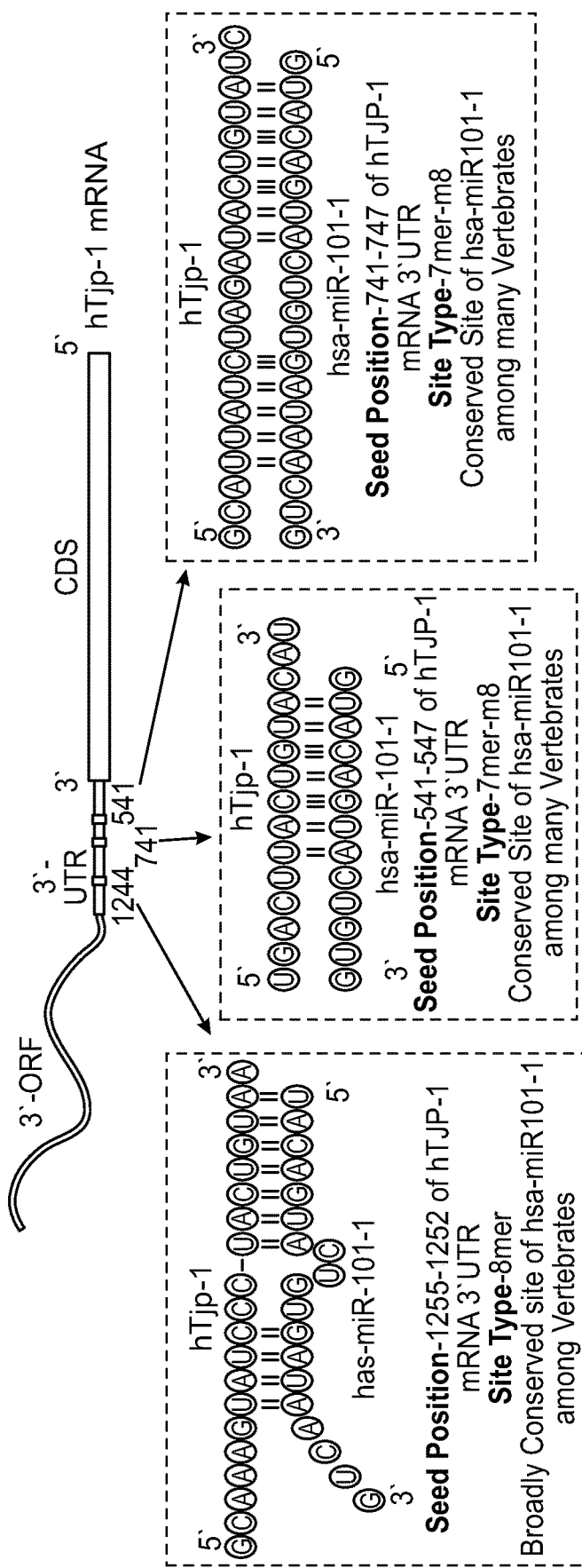
FIG. 6C is a representation of three miR101a-3p binding sites on human Tjp1 mRNA 3' UTR sequence (seed positions). Values presented are mean of n=2-3 repeated triplicate of Caco2 culture experiments in each group and error bars are standard error of means. P values with *<0.05; <0.01 and *<0.001 are statistically significant.
Figure 19A:
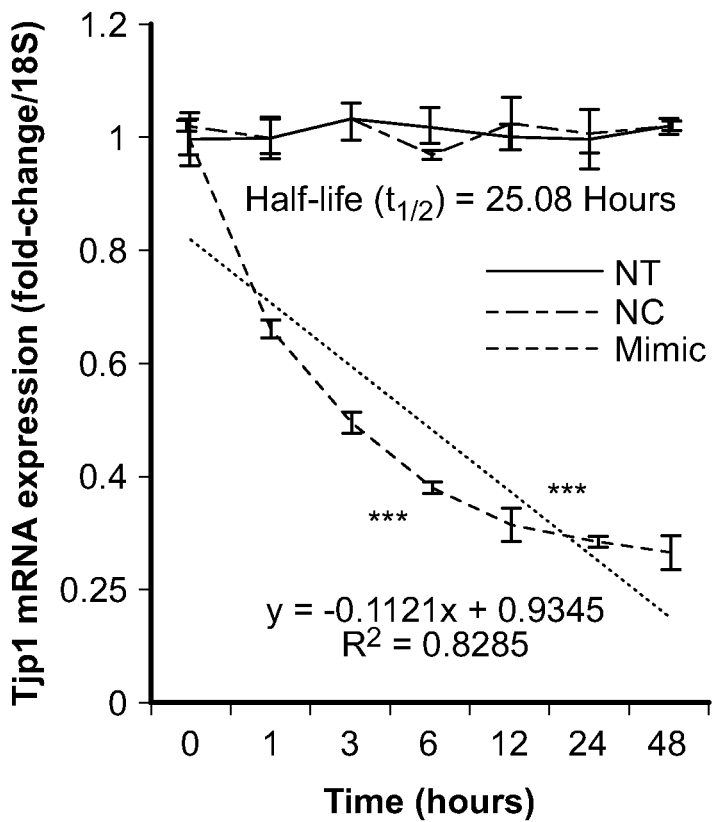
FIG. 19A shows Tjp1 mRNA stability was significantly decreased Caco2 cells treated with miR101a-3p mimetic (mimic) compared to their controls. Values presented are mean of Caco2 culture experiments performed in triplicates and repeated 2-3 times, and error bars as standard error of means. P values with ***<0.001 are statistically significant.
Figure 19B:
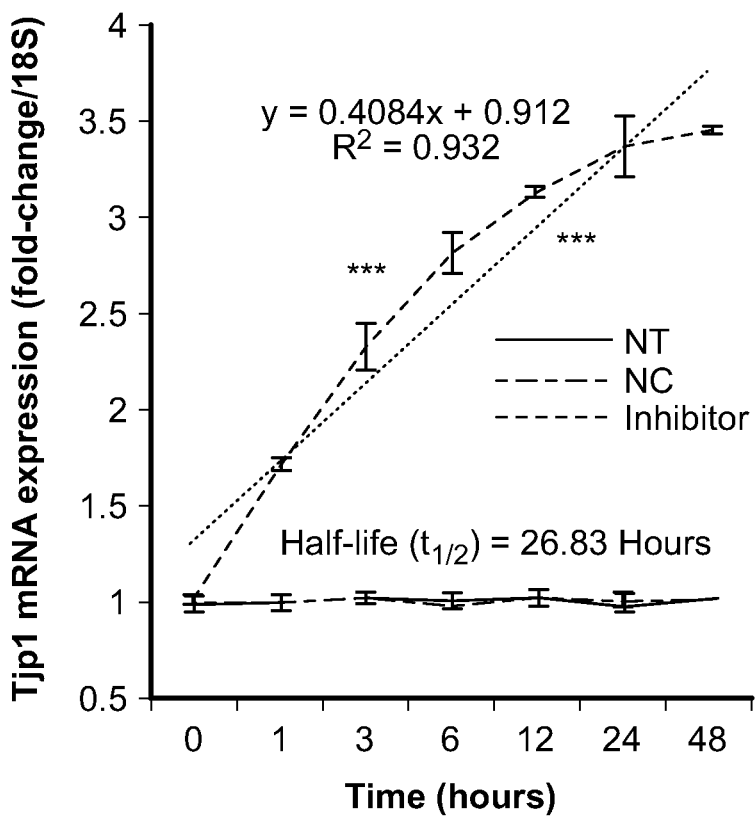
FIG. 19B shows Tjp1 mRNA stability was significantly reversed by miR101a-3p inhibitor compared to their controls. Values presented are mean of Caco2 culture experiments performed in triplicates and repeated 2-3 times, and error bars as standard error of means. P values with ***<0.001 are statistically significant.
Figure 20A:
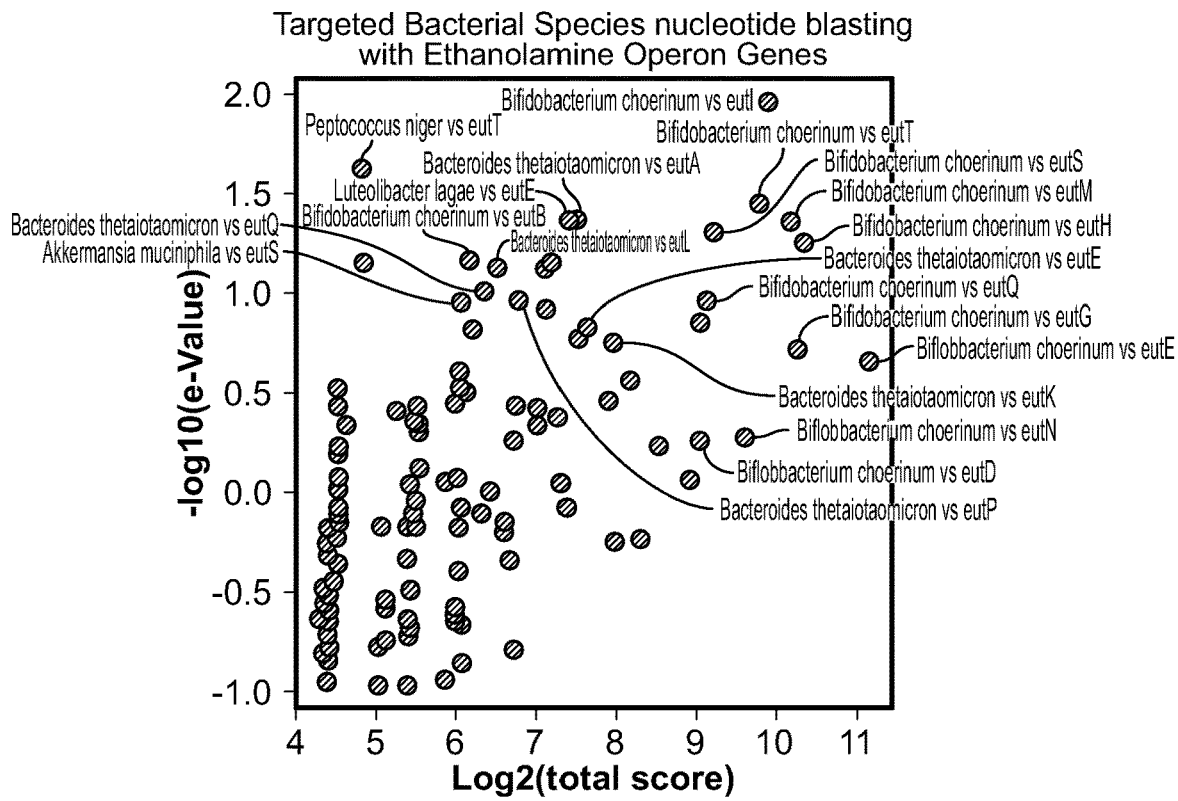
FIG. 20A shows in-silico prediction analyses depicting that Eut operon presents in bacterial species using nucleotide based BLAST analyses.
Figure 20B:
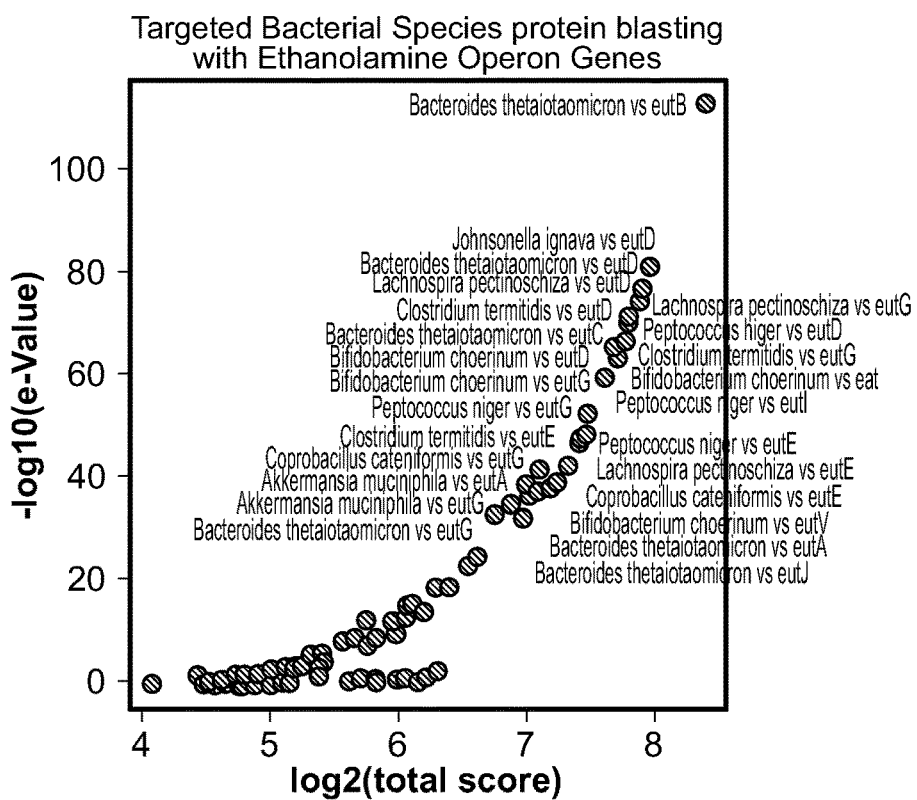
FIG. 20B shows in-silico prediction analyses depicting that Eut operon presents in bacterial species using protein based BLAST analyses.
Figure 20C:
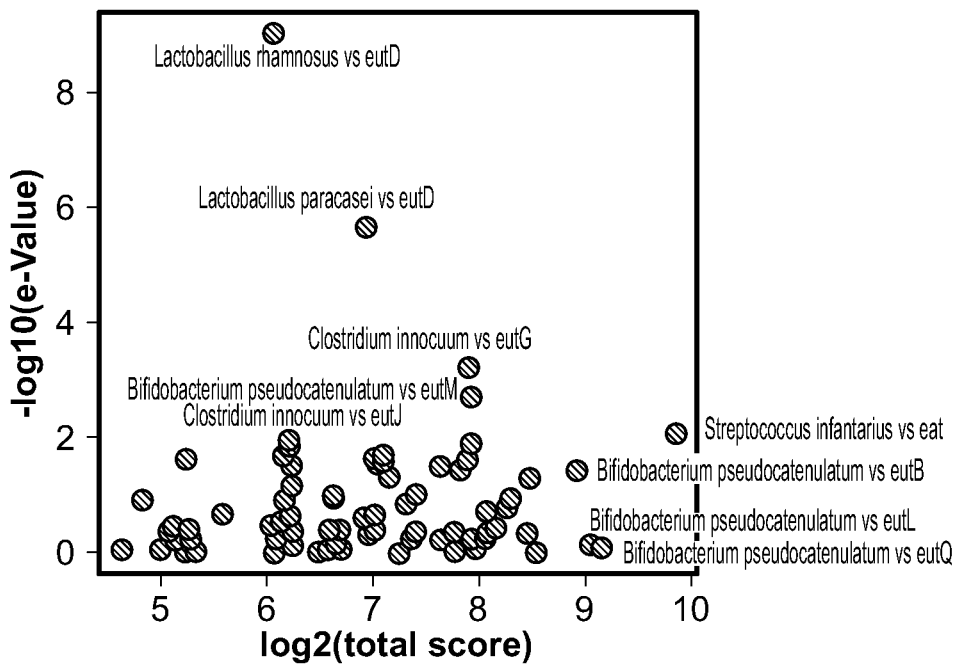
Figure 20D:
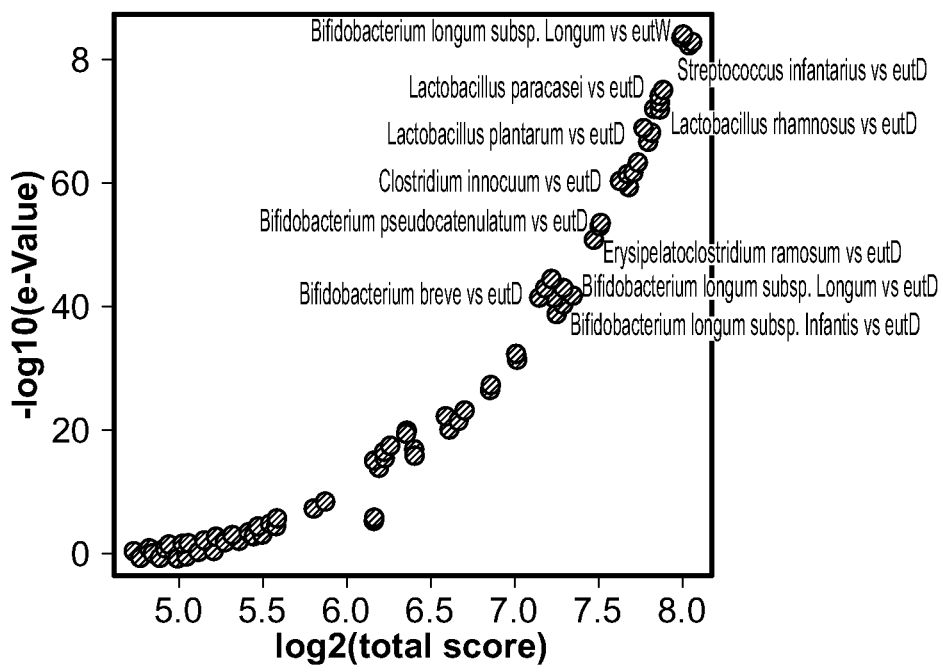

Ethanolamine activated miR101a-3p promoter by enhancing ARID3a binding. To further discover how ethanolamine induced miR101a-3p promoter, an unbiased promoter-protein binding pull-down assay was performed, using −500 to −1000 bp fragment of miR101a-3p promoter and non-targeted proteomic analyses and found that a transcription factor-ARID3a was abundant in miR101a-3p promoter transfected pull-down samples compared to scrambled promoter transfected controls (FIG. 5C and FIGS. 9A-9C). Further, in-silico analyses on search engines such as oPOSSOM V3 and ConTra V3 found that ARID3a has a predictive binding sequence on the miR101a-3p promoter (FIGS. 17A-17B). Interestingly, ARID3a expression was significantly higher in the intestines of DIO and db/db, their FMT recipients as well as in enteroids and Caco2 cell monolayers treated with DIO and db/db FCMs and/or ethanolamine (FIGS. 5D-5N). ARID3a siRNA transfected Caco2 cells showed no increase in the miR101a-3p promoter luciferase activity, miR101a-3p expression, and Tjp1 mRNA upon ethanolamine treatment compared to scrambled controls (FIGS. 5O-5P), indicating that the ethanolamine effects on miR101a-3p promoter are mediated through ARID3a binding. Altogether, these results demonstrated that the elevated ethanolamine in the gut activates ARID3a binding on miR101a-3p promoter to increase miR101a-3p expression, which in turn reduces Tjp1 expression.

miR101a-3p reduced Tjp1 expression by decreasing its mRNA stability. The correlation network analyses, combining miRNA profiles and gene expression data from intestines of FMT recipients, FCM treated enteroids, and Caco2 cells versus controls, revealed the highest negative correlation between miR101a-3p and Tjp1 (FIGS. 6A-6B; FIGS. 18A-18E), suggesting that increased miR101a-3p expression is linked with decreased Tjp1 expression. miRNA target analyses also revealed that the 3'-untranslated region (3'-UTR) of Tjp1 mRNA consisted of three potential miR101a-3p binding sites (FIG. 6C), indicating that miR101a-3p can directly bind to the Tjp1 mRNA to change its expression. Further, Caco2 cells transfected with miR101a-3p mimetic significantly reduced the mRNA levels of Tjp1 while miR101a-3p inhibitor reversed these changes (FIG. 6D); suggesting that the miR101a-3p reduces Tjp1 mRNA stability. The overexpression of miR101a-3p mimetic in Caco2 cells remarkably reduced the stability of Tjp1 mRNA while miR101a-3p inhibitor reversed it (FIGS. 6E-6F; FIGS. 19A-19B). In addition, the effect of ethanolamine in reducing Tjp1 expression was elapsed in miR101a-3p inhibitor treated cells. These results indicate that the microbiota/ethanolamine induced miR101a-3p binds to Tjp1 mRNA and reduces its stability, resulting in a diminished Tjp1 expression.

Figure 7A:
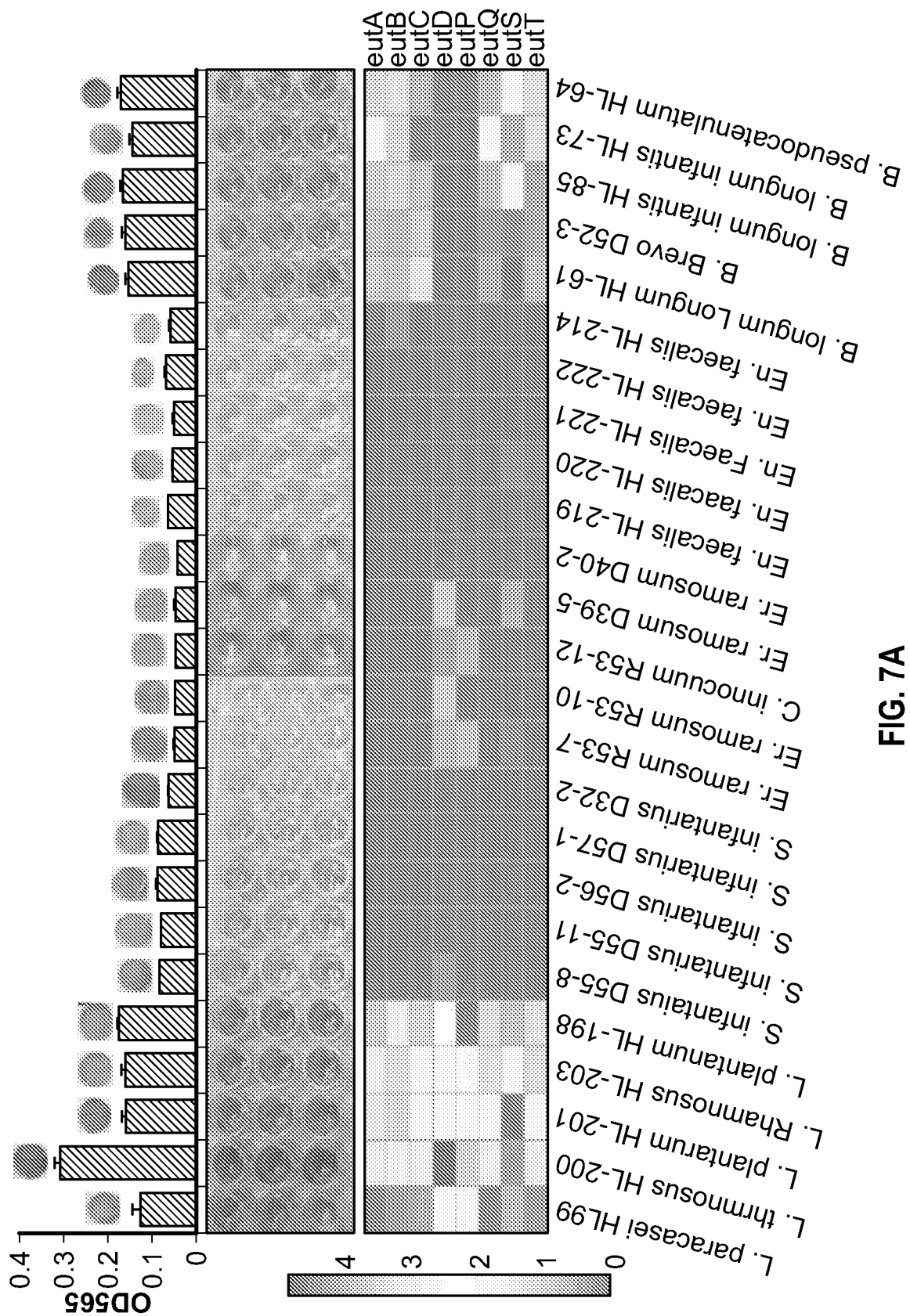
FIG. 7A shows that a probiotic therapy restored ethanolamine metabolizing capacity in microbiota, which in turn mitigated leaky gut by restoring homeostasis in ARID3a/miR101a-3p/Tjp1 axis. A) Screening of ethanolamine metabolizing capacity of human origin probiotics using a colorimetry assay and measuring expression of ethanolamine utilizing operon genes, to find *Lactobacillus rhamnosus* HL-200 as a potential ethanolamine metabolizer.
Figures 7H, 7I, 7J:
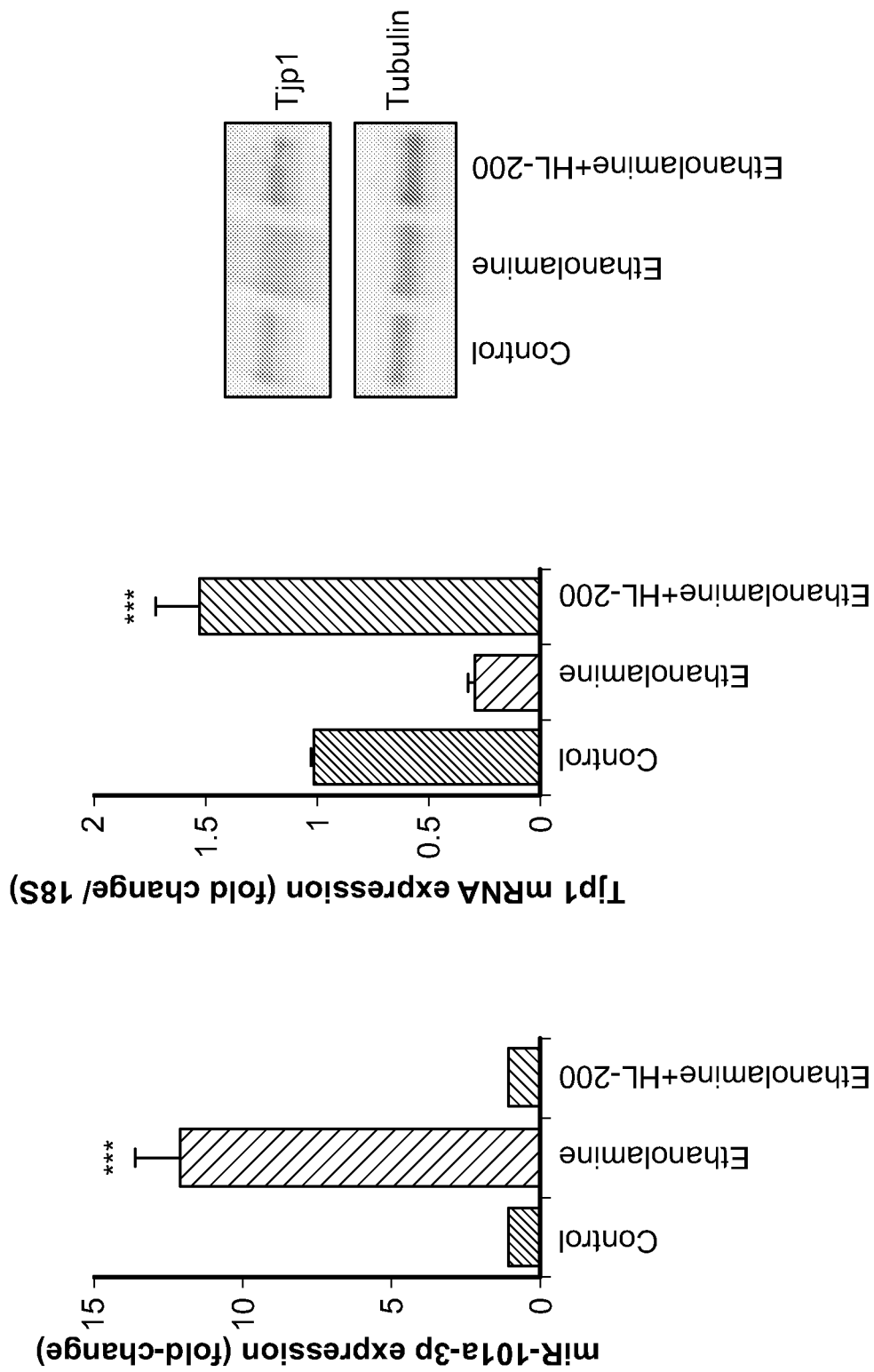
FIG. 7H shows that feeding of HL-200 to mice significantly reduced expression of miR101a-3p in the gut compared to controls.
FIG. 7I shows that feeding of HL-200 to mice significantly reduced expression of Tjp1 mRNA in the gut compared to controls.
FIG. 7J shows that feeding of HL-200 to mice significantly reduced expression of Tjp1 protein in the gut compared to controls.
Figure 7K:
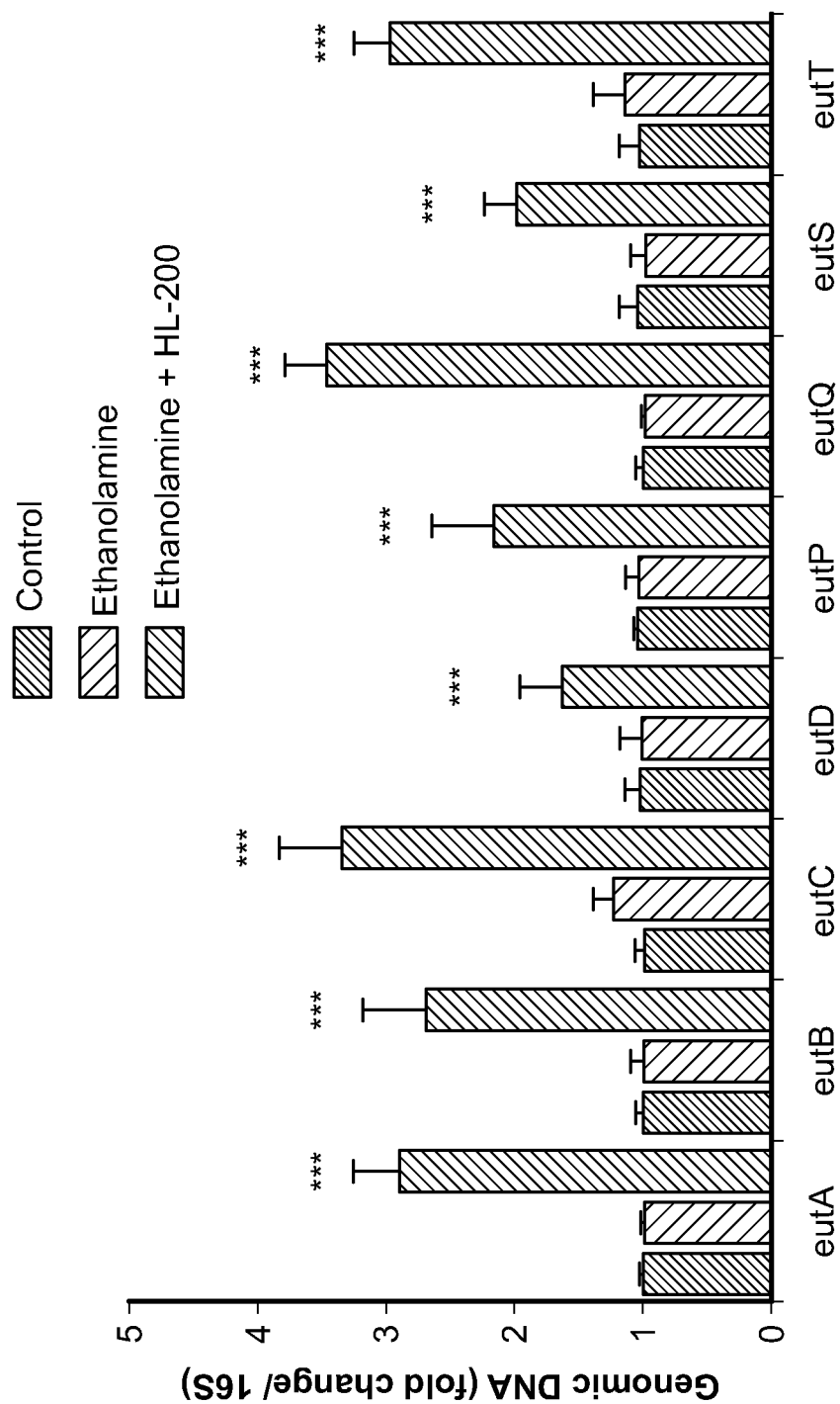
FIG. 7K shows a significant increase in expression of ethanolamine utilizing operon genes in the gut compared to controls.
Figure 7N:
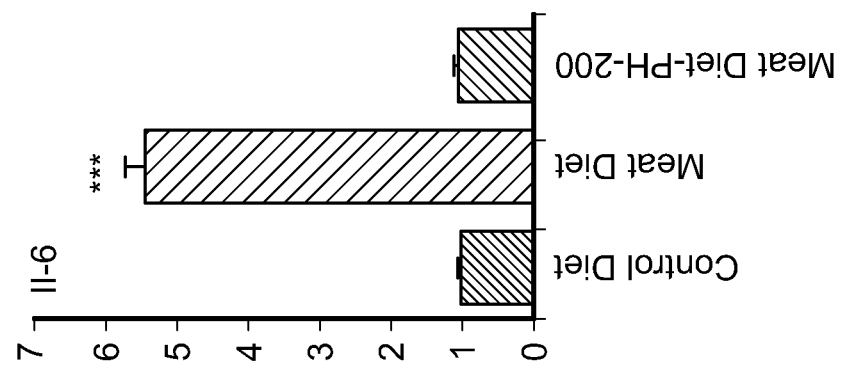
FIG. 7N shows that meat supplemented diet significantly increased inflammation (Il-6).
Figure 7M:
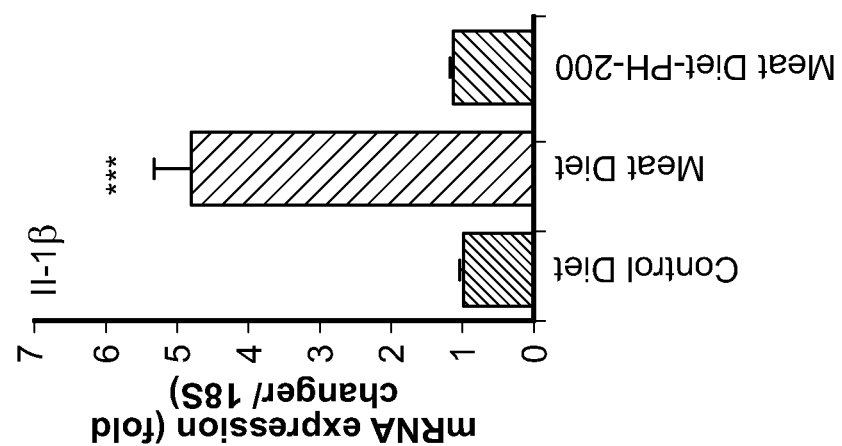
FIG. 7M shows that meat supplemented diet significantly increased inflammation (Il-1 $\beta$).
Figure 7L:
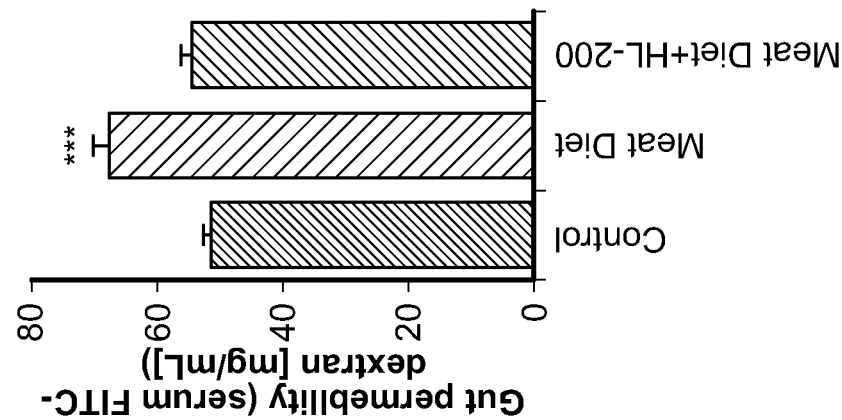
FIG. 7L shows that meat supplemented diet significantly increased leaky gut.

Restoring ethanolamine metabolizing capacity in microbiota using a human origin probiotic therapy reduced leaky gut and inflammation. The results showed that ethanolamine increased in obese/T2D gut was due to its under metabolization by microbiota, and such a raised ethanolamine stimulates ARID3a binding on miR promoter to elevate miR101a-3p, which reduces Tjp1 and causes leaky gut. It was tested whether recovering microbiome capacity to metabolize ethanolamine could reverse these abnormalities in gut. The non-targeted in-silico prediction analyses revealed that the several commensals like Lactobacilli, Bifidobacteria, Akkermansia, Bacteroides and *Clostridium* often express Eut operon (FIGS. 20A-20D; FIG. 21) and discovered that the abundance of such bacteria were significantly lower in the gut of obese/T2D mice. (Nagpal et al., 2018; Nagpal et al., 2020). An array of novel human-origin strains of *Lactobacillus* and Bifidobacteria for ethanolamine metabolizing ability and found that *Lactobacillus* (*L.*) *rhamnosus* HL-200 (HL-200) strain exhibited the highest activity to metabolize ethanolamine (FIG. 7A, upper panel). Analysis also demonstrated the highest expression of Eut operon among tested strains (FIG. 7A, lower panel). Further, we showed that one week feeding of the HL-200 significantly decreased ethanolamine-induced leaky gut and inflammation along with decreased miR101a-3p and increased Tjp1 expressions in the mouse gut (FIGS. 7B-7K, FIGS. 22A-22E). The feeding of meat-supplemented diet also significantly increased leaky gut and inflammation along expression of miR101a-3p and Tjp1 by restoring ethanolamine operon genes expression compared to isocaloric diet fed mice, suggesting that the meat-based diet can over-supply ethanolamine, which can further exacerbate its abundance in gut, especially when it is being under metabolized. However, such abnormalities were not seen in the mice pre-fed (1-week) with HL-200 (FIGS. 7L-7Q). Overall, these results demonstrated that the increased ethanolamine derived from diet or host gut can be reduced by replenishing the ethanolamine metabolizing capacity of microbiota, using probiotics HL-200 therapy to reverse leaky gut and inflammation.

Discussion

Low grade chronic inflammation is a key driver of obesity and T2D pathophysiology. (Monlun et al., 2018; Scheithauer et al., 2020). While many sources of inflammation exist, treatable and safe targets are elusive. Evidence indicates that leaky gut, which allows the release of proinflammatory molecules from the gut to the systemic circulation is an understudied target of inflammation in the patients with obesity and T2D. Hyperglycemia induces a breakdown of tight junction barriers and leaky gut. (Thaiss et al., 2018). However, leaky gut is also present in a variety of disorders in non-diabetic patients such as inflammatory bowel diseases; and, in fact, leaky gut and low grade inflammation are a hallmark of aging-related disorders. (Franceschi et al., 2018; Odenwald et al., 2016; Kennedy et al., 2014). Microbiota abnormalities co-occur with leaky gut and inflammation; however, precise mechanisms as to whether and how abnormalities in microbiota contribute to a leaky gut and inflammatory syndrome of obesity/T2D remain largely unknown. The transplantation of the intestinal microbiota from obese/T2D mice models (db/db and HFD-induced obese [DIO] mice) to normoglycemic, lean, and conventional mice, significantly increased leaky gut and inflammation in the recipient mice, thus confirming the causal role of such microbiota in instigating leaky gut and inflammation. Interestingly, these effects were independent of the blood glucose levels as obese/T2D microbiota were transplanted in normoglycemic and normal weight mice, indicating hyperglycemia was not the main driver for a leaky gut. The transplantation of obese/T2D microbiota reduced the expression of Tjp1/Zo1 and Occludin (Ocln), suggesting that they induce leaky gut by dampening barrier function through reduced expression of tight junction proteins. Fecal conditioned media (FCM) recapitulated the effects of FMT on leaky gut and inflammation; this result supports previous observations, demonstrating that microbial metabolites are of key importance to explain the impact of the gut microbiota perturbations on health (Yadav, 2016); thus, FCM can be used as an alternative model to investigate microbiota mediated mechanisms on the intestinal epithelial disruptions. Through our unbiased and non-targeted metabolic approaches, we have discovered a single metabolite-ethanolamine, which significantly accumulates in the gut of obese/T2D gut, induces leaky gut, and reduces expression of Tjp1 in in-vitro, ex-vivo and in-vivo models. Our results establish that a microbial metabolite, such as ethanolamine, can dampen intestinal barrier functions by reducing expression of Tjps, and thus recapitulating the effect of obese/T2D FMTs on gut barrier.

As a further step to deciphering the fine mechanism involved in such results, un-biased and non-targeted global microRNA expression analyses have revealed that the expression of miR101a-3p was significantly increased in the gut of obese/T2D FMTs recipient mice as well as in obese/T2D FCMs, ethanolamine treated enteroids, and human intestinal epithelial cells. Also, a lentiviral vector-based increase in miR101a-3p accumulation reduced Tjp1 expression and increased leaky gut. Further, in-silico miRNA target analysis revealed that the Tjp1 mRNA have miR101a-3p binding sites thus miR101a-3p reduces Tjp1 mRNA stability. These results corroborated that miR101a-3p expression induced by gut microbiota dysbiosis through ethanolamine reduces the Tjp1 expression by reducing its mRNA stability. The miR101a-3p regulates a myriad of cellular processes in cancer biology and other human diseases (Wang et al., 2018; Hackl et al., 2010; Lippi et al., 2016); This example unveils miR101a-3p's role in regulating gut permeability and sensing microbiota signals through ethanolamine. Our further un-biased promoter pulldown chromatin immunoprecipitation assay has led to the discovery that the transcription factor-ARID3a46,47 binds on miR101a-3p promoter and increases its expression in response to ethanolamine and/or microbiota transplantation. These results have evidenced, for the first time, that a microbial metabolite such as ethanolamine in obese/T2D gut enhances ARID3a binding on the promoter of miR101a-3p, which, in turn, destabilizes mRNA stability of Tjp1, thus reducing Tjp1 expression and finally inducing leaky gut. These results open future opportunities to test whether miR101a-3p inhibitor-based therapy (Chakraborty et al., 2021) may show efficacy against leaky gut and its associated diseases.

Ethanolamine is a common constituent of animal/human and bacterial cells and remains a valuable source of carbon and/or nitrogen for several bacteria capable of its catabolism. (Patel et al., 2017). Ethanolamine is highly prevalent in the gut because it is the derivative of the cell membrane phospholipid phosphatidylethanolamine of host and bacteria produced during rich turnover of intestinal epithelial cells. (Patel et al., 2017). Thus, increased ethanolamine in the gut could be due to over-consumption of animal products/meat-based diet, increased intestinal cellular turnover, and/or reduced ethanolamine metabolization by the gut microbiota. Notably, HFD (including lard as an ethanolamine source) and meat-based diet feeding increased leaky gut and reduced Tjp1 expression. Previously, it was shown that obese/T2D mice gut have higher cellular turn-over gene program. (Nagpal et al., 2018). In the present study, ethanolamine levels were significantly increased in the gut of non-meat supplemented normal chow fed db/db mice, thus indicating that a higher cellular turn-over alone could increase the levels of ethanolamine in the obese/T2D gut. Ethanolamine is consumed by bacteria that express ethanolamine operon genes like EutA, EutB and EutC, and the expression of these genes was significantly reduced in the obese/T2D mice feces, suggesting that the obese/T2D microbiota yielded a reduced capacity to metabolize ethanolamine, which, in turn, increased its abundance in the gut. Similarly, significantly decreased expression of ethanolamine metabolizing operon genes in the feces of obese humans suggested that the increased abundance of ethanolamine, due to reduced ethanolamine metabolizing capacity of microbiota, could be a clinically important hallmark of elevated leaky gut and inflammation in obese humans. Interestingly, these results also indicated that gut microbiota also worked like a garbage remover by metabolizing detrimental metabolites like ethanolamine, thus reducing their detrimental effects on gut epithelia.

Probiotics are live bacteria that confer beneficial effects on host health by potentially modulating gut microbiota. (Yadav et al., 2013; Nagpal et al., 2018; Mishra et al., 2019; Ahmadi et al., 2020; Yadav et al., 2013; Yadav et al., 2007). In efforts to restore ethanolamine metabolizing capacity of gut microbiota metabolizing probiotic therapy, human origin probiotic lactobacilli strains were screened for their ethanolamine metabolizing capacity. The unbiased screening found that *Lactobacillus* (*L*.) *rhamnosus* HL-200 isolated from human gut showed the highest ethanolamine metabolizing capacity. Notably, restoring ethanolamine metabolizing capacity in the gut, using HL-200 probiotic therapy, reduced the adverse effects of ethanolamine and/or meat supplemented diet on leaky gut and inflammation by maintaining higher expression of Tjp1 and strengthening intestinal epithelial barrier functions. The definite demonstration of their activity and identification of the mechanisms involved have remained a huge challenge. This example provides substantial support to the impact of HL-200 probiotics-based approach for counteracting leaky gut and inflammation.

This example offers a compelling and comprehensive mechanism to account for the leaky gut and subsequent inflammation observed in patients with obesity/T2D. It also shows a unique property of gut microbiota as a garbage cleaner for end products such as ethanolamine of gut dead cells, preventing their adverse effects on gut barrier. This example has shown how a decline in ethanolamine metabolization capacity of microbiota in humans and mice induces leaky gut and inflammation. This example presents strategies to restore such ethanolamine metabolizing capacity of microbiota by using a human-origin probiotic therapy.

Methods

Animal studies. C57BL/6J (B6) mice and Leptin receptor knock-out (db/db) mice were purchased from Jackson Laboratory (Bar Harbor, ME, USA) and were acclimatized for 2 weeks in our vivarium by maintaining under 12 h light-dark cycle before start of experiment. At the age of 4 weeks, the mice (n=5) were divided into 4 groups—1) B6-NC: Control B6 fed with Normal Chow; 2) B6-LFD: fed with low fat diet (LFD, 10% kcal fat; Research Diets Inc); 3) db/db: fed with normal chow and 4) diet induced obese (DIO): B6-mice fed with high fat diet (HFD, 60% kcal fat, Research Diets Inc). At the age of 16 weeks, fecal samples were collected from each group for microbiome, metabolite, FMTs and FCM studies. For FMT studies, B6 mice (n=9; age of 8 weeks) were divided into three groups (n=6-8 in each group)—1) B6-FMT, 2) db/db-FMT and 3) DIO-FMT); and after gut cleansing process using antibiotics and polyethylene glycol (Ahmadi et al., A human-origin probiotic cocktail ameliorates aging-related leaky gut, 2020; Ahmadi et al., Metformin reduced aging-related leaky gut, 2020; Wang et al., 2020) the recipient mice were administered with B6, db/db and DIO fecal slurry, respectively for 7 days. In addition, lentiviral particle carrying mimetic-miR101a-3p were administered through enema twice a week in B6 mice and compared with scramble lentivirus ingested controls (n=5 in each group). For probiotic therapy experiments, the B6 mice were also treated with 500 mM ethanolamine (Ethn) and probiotics HL-200 and their combination for 7 days and compared with PBS only administered controls. Also, meat diet with and without probiotics HL-200 were fed to B6 mice (n=9 in each group) for 1 week and compared with control diet fed controls. All the animal experiments and procedures were approved by the IACUC of Wake Forest School of Medicine and University of South Florida.

Leaky gut assay. Four-hour pre-fasted mice were orally administered with 1 g/kg body weight FITC (Fluroescein isothiocyanate)-dextran (4 kDa; Sigma Aldrich); and blood was collected after 4 hrs. Serum was isolated to measure the appearance of FITC fluorescence at 485 nm excitation and at 530 nm emission, using fluorescence 96-well plate reader (PolarStar Omega), which was calculated using FITC-dextran standard curve. (Nagpal et al., 2018; Ahmadi et al., A human-origin probiotic cocktail ameliorates aging-related leaky gut, 2020; Ahmadi et al., Metformin reduced aging-related leaky gut, 2020; Ahmadi et al., 2019).

Microbiota analyses. Genomic DNA was extracted from mice feces using the Qiagen DNA Stool Mini Kit (Qiagen), and the V4 region of bacterial 16S rDNA was amplified using primers 515 F (barcoded) and 806 R. (Caporaso et al., 2010). After being purified and quantified with AMPure® magnetic purification beads (Agencourt) and Qubit-3 fluorimeter (InVitrogen), respectively. Equal amounts (8 pM) of the amplicons were applied for sequencing using the Illumina MiSeq sequencer (Miseq reagent kit v3). The sequences were de-multiplexed, quality filtered, clustered, and analyzed with the Quantitative Insights into Microbial Ecology (QIIME) and R-based analytical tools. (Caporaso et al., 2010; Navas-Molina et al., 2013; Kuczynski et al.).

Metabolomics analysis. Global metabolomics was performed, using NMR spectrometry in the fecal samples, using a method described by Gratton et al. (Kuczynski et al., 2011) with slight changes. The extracted water samples were mixed with phosphate buffer containing 10% D2O and 0.1 mM Trimethylsilyl propionate (TSP). NMR experiments were carried out on a Bruker Ascend 400 MHz high-resolution NMR (Bruker Biospin) using a 1D first increment of a NOESY (noesygpprld) with water suppression and a 4-s recycle delay. All NMR spectra were phased and referenced to TSP in TopSpin 4.06 (Bruker BioSpin). The NMR spectra were analyzed in Amix 3.9 and a manual pattern was created using the metabolites peaks range determined by Chenomx 8.4 (Chenomx Inc) to extract the metabolites peak intensities. Total intensity normalization was applied before further data analysis.

Enteroids development and treatments. To develop mouse enteroids, entire small intestine was collected from mice and flushed with pre-cooled Dulbecco's phosphate buffered saline (DPBS). The lengthwise cut-opened ileum was washed with cooled PBS and fragmented into 2 mm small pieces, then transferred to a 50-ml conical flask containing cleaned pre-cooled PBS. Tissue fragments were incubated in the 25 ml of pre-warmed Trypsin (Gibco) on a rocking platform for 15 minutes. After removing the trypsin, tissue pieces were washed with 10 ml pre-cold PBS with 0.1% bovine serum albumin and filtered in a 50 ml conical tube through a 70 µm cell strainer (Falcon). These pieces were then centrifuged at 290×g for 5 min at 4° C., and the intestinal crypt-containing pallets were suspended in the 10 mL cold DMEM: F-12 (Gibco) and centrifuged at 500×g for 10 minutes followed by resuspending in 150 µL IntestiCult Organoid Growth Medium (StemCell) with 50 m/mL gentamicin (Gibco). The Matrigel Matrix (Corning) was added to the suspension and the mixture of 50 µL was used to form a dome at the center of a prewarmed 24-well culture plate and incubated at 37° C. and 5% CO2 for 30 minutes to allow the Matrigel to set. To maintain the cultures, the IntestiCult Organoid Growth Medium was changed three times/week, and images were captured by from day 1 to 12. On day 10, the organoids were treated with fecal condition media (FCM), metabolites, and ethanolamine with three replicates in each group. The organoids were harvested after 2 days of treatment(s) for miRNA, mRNA, and protein analyses. Experiments were repeated three times.

FCM preparation. Fresh feces collected from mice were snap frozen in liquid nitrogen and crushed, using a mortar and pestle. The fine powered feces (100 mg) were suspended in 100 mL cold DMEM (Gibco) media and kept on a shaker at a speed of 200 rpm for 1 hour to mix properly in a cold room. The suspended media was filtered two times through 0.45 µm filters (Corning), followed by two times through 0.22 µm sterile syringe filters in sterile conditions. The 1:40 diluted FCM was used to treat the intestinal organoids and cells.

Transepithelial electric resistance (TEER) assay in Caco-2 cell monolayers. Human intestinal epithelial Caco-2 cells (American Type Culture Collection) were seeded on apical chamber made of polyester membrane filters with 0.4 µm pore size of 12-well transwell plates (Costar) at a density of $3\times10^5$/well. The culture medium from both apical and basolateral compartment were changed every two days. The cells were allowed to fully differentiate for 21 days; and fully differentiated cells were challenged with FCM and metabolites for next 8 hours with continuous measuring of TEER values, using an EVOM2 Epithelial Voltometer (WPI) according to the manufacturer's instruction. The blank inert resistance value (the insert with only culture media) was subtracted from the measured resistance value of each sample and final resistance in ohm×cm2 was calculated by multiplying the sample resistance by the area of the membrane.

FITC-dextran permeability assay in Caco-2 cell monolayers. Fully differentiated Caco2 cells up to 21 days, the FITC-dextran 4 (3-5 kDa; Sigma Aldrich) solution (1 mg/ml) was added on the apical (upper) side of the monolayers along with treatments of corresponding FCM and metabolites. The basolateral side media was collected to determine the FITC levels, using fluorescent reader and standard curve, as described earlier. (Ahmadi et al., A human-origin probiotic cocktail ameliorates aging-related leaky gut, 2020).

Western Blots. Total proteins from tissues, organoids, and cells were extracted, using homogenized lysis buffer as mentioned in previous publications. (Nagpal et al., 2018; Yadav et al., 2013; Ahmadi et al., A human-origin probiotic cocktail ameliorates aging-related leaky gut, 2020; Ahmadi et al., Metformin reduced aging-related leaky gut, 2020; Wang et al., 2020; Yadav et al., 2011). Proteins were resolved by SDS-PAGE electrophoresis and transferred to PVDF membrane for Western blotting. Membranes were developed with primary antibodies tight junction protein-1 (Tjp-1) (Tjp1 (Zo-1), Invitrogen) and Arid3a (Santa Cruz Biotechnology), followed by secondary antibody and developing with chemi-luminiscent kit (ECL, Thermo Scientific) and imaged on PXi with the GeneSys software (SynGene). Tubulin was used as the internal loading control.

RNA isolation and gene expression analyses. Total and small RNAs were isolated from tissue, enteroids, and cells collected and stored in RNAlater solution at −80° C. using RNeasy Mini Kit. Total RNA from bacterial cells were extracted, using RNAprotect bacteria reagent and RNeasy Mini Kit (Qiagen). The complementary DNA (cDNA) was synthesized from total and small RNAs, using High-Capacity cDNA reverse transcription kit (Applied Biosystems). The normalized cDNA of each sample was used to run the qRT-PCR, using 7900 real time PCR machine (Applied Biosystem) using SYBR Green master mix (Applied Biosystem) and gene specific primers. Relative gene expression rate was analyzed, using $\Delta\Delta CT$ method normalized by 18S as internal control. All the reactions were performed at least in triplicates.

miRNA profiling and expression analyses. For miRNA profiling, the total small RNA was extracted from enteroids treated with FCMs of B6, db/db and DIO, using miRNeasy Mini kit (Qiagen) and analyzed by the NanoString nCounter miRNA Assays, using 50-100 ng of total RNA from each sample in four replicates, and using eight positive control probes and 8 negative control probes. Data were analyzed, using nSolver analysis software version 4.0. For each miRNA background correction count was carried out by subtracting mean +2 standard deviations of eight negative control probes as a cut off. The miRNA of count 50 or more after background correction was further used for analysis. The individual miRNA expression was quantified, using qRT-PCR by converting small RNAs to cDNA using TaqMan MicroRNA Reverse Transcription kit (Applied Biosystems) and TaqMan 2X Universal PCR Master Mix, No AmpErase UNG (Applied Biosystem) on 7900 real-time PCR machine. Taqman primers were used for specific miRNAs, and RNU6B was used as an internal control; and relative expression was calculated using ΔΔCT method.

miRNA transfection to Caco-2 cells. Caco-2 cells were grown up to 80-90% confluency and were transfected with miRIDIAN mimetic negative control #1, miRIDIAN mimetic mmu-miR-101a-3p and miRIDIAN hairpin inhibitor mmu-miR-101a-3p (Dharmacon), using Lipofectamine 3000 transfection kit (Invitrogen). The cells were harvested after 48 hours for miRNA, mRNA, and protein expression analyses.

Lentivirus transfection to mice. B6 mice were anesthetized with 3.75% isofluorane and were administered with Lentivirus carrying miR101a-3p inhibitor, mimetics and scrambled miRNA sequence through enema. Prior to instillation, mice were given an enema of 100 μl 50% ethanol (v/v in ddH2O); and then after 2 hrs, 100 μl of vehicle or viral vector solution containing a titer of 0.5×10⁸ transducing units (TU) administered intrarectally through a 1.2 mm diameter catheter. The mice were inverted for 30 seconds after administration of enema to prevent leakage. After measuring leaky gut, mice were euthanized to collect tissues for further analyses.

Promoter luciferase assay. Caco-2 cells were seeded onto a 96-well plate at a density of 2×10⁴ cells/well and transfected with miR101a-3p promoter pMK-RQ (KanR) reporter vector of 4 different nucleotide sequence (−1 to −500, −1 to −1000, −1 to −1500 and −1 to −2000) from its TSS (Transcription start site) and pMK-RQ (control vector using Lipofectamine 3000 transfection kit (Invitrogen). The TSS of miR101a-3p is located at position: chr1 65067704 (genome version hg38) as reported earlier. (Huang et al., 2017). The cells were collected at various time point (0, 1, 3, 5, 7 and 10 hrs) after transfection. The expression level of the firefly luciferase reporter gene was measured using Pierce Firefly Luciferase Glow Assay Kit.

mRNA stability assay. Caco-2 cells are transfected with mimetic miR-101a-3p and inhibitor miR-101a-3p, and cDNA was synthesized after harvesting the transfected cells at 0, 1, 3, 6, 12, 24 and 48 hrs timepoints. The half-life of the Tjp1 mRNA expression was calculated using a formulae: $E(t)=E0\times(1/2)^{(t/t1/2)}$, where, 'E(t)' stands for expression of Tjp1 at time point 't' after transfection with mimetic miR-101a-3p and inhibitor miR-101a-3p, 'E0' stands for the initial expression level of Tjp1 before transfection, 't' stands for the time elapsed after transfection, 't½' stands for the half-life in the Tjp1 expression on transfection with mimetic miR-101a-3p and inhibitor miR-101a-3p.

Chromatin immunoprecipitation protein-DNA pulldown assay. Fully differentiated 21-day old Caco-2 cells were treated with 10 μM ethanolamine for 48 hrs., then washed cells were treated with PBS buffer containing inhibitors (PBSI)—0.5 mM PMSF (Phenylmethylsulphonyl fluoride), 1 mM sodium vanadate, 0.5 mM Dithiotreitol, 1 μg/mL Leupeptin, 25 mM β-glycerophosphate, 10 mM sodium fluoride, then were harvested and suspended in 2 package cell volume of buffer A with inhibitors (10 mM 4-(2-hydroxyethyl)-1-piperazineethanesulfonic acid, 1.5 mM magnesium chloride, 10 mM potassium chloride, 300 mM sucrose, 0.5% NP-40) and kept on ice for 10 minutes. After vortexing briefly, and centrifuging at 2600 g for 30 s, the supernatant was discarded. Cell pellets were resuspended in ⅔ package cell volume with buffer B containing inhibitors (20 mM HEPES, pH 7.9, 1.5 MgCl2, 420 mM sodium chloride, 0.2 mM EDTA, 2.5% glycerol). After sonication, and centrifugation at 10,400 g for 5 mins, the supernatant was isovolumetrically diluted with buffer D containing inhibitors (20 mM HEPES, pH 7.9, 100 mM potassium chloride, 0.2 mM EDTA, 8% glycerol). Total protein (400 μg) of nuclear extract was normalized among the samples and two drops (40 μl) of streptavidin-agarose bead were suspended and 4 μg of 5'-biotynylated-pmiR101a-3p (−1000 to −500 bp promoter sequence of miR101a-3p and scrambled sequence as control) in 500 μl of PBSI. After rocking this mixture for 2 hrs. and centrifuging it at 550 g for 1 min, the supernatant was discarded. The pellet was washed with PBSI for 3 times and was resuspended in 40 μl of 2× Laemmli sample buffer and incubated for 95° C. for 5 min to obtain beads.

Beads were placed onto the polyethylene filter in the Pierce 0.8 mL Centrifuge Columns (Thermo Scientific) and were washed three times by adding 200 μL of washing buffer (50 mM ammonium bicarbonate solution) and centrifugation at 1,000×g for 1 min for each time. The bottom end of the column was capped, and 200 μL of washing buffer containing 10 mM dithiothreitol solution was added. With the top capped, the column was agitated on a tube rotator for 1 hour at 37° C. The bottom cap was removed, and the tube was centrifuged at 1,000×g for 1 min to remove supernatant. Beads were then incubated in 200 μL of 30 mM iodoacetamide solution for 45 minutes at room temperature in the dark. Beads were washed with 200 μL of washing buffer three times. 200 μL of digestion buffer (50 mM ammonium bicarbonate solution containing sequencing grade modified trypsin) was added, and the tube was incubated overnight at 37° C. Enzyme reaction was quenched by adding 10 μL of 20% formic acid and the column was centrifuged to collect flow-through in the collection tube. Beads were washed with 100 μL of 50% acetonitrile containing 0.1% formic acid twice and the flow-through was combined with the initial eluent. Beads were washed again with 80% acetonitrile containing 0.1% formic acid, and flow-through was collected in the same tube. Solution was dried under vacuum and then prepared in 5% acetonitrile with 1% formic acid and were injected in a LC-MS/MS system consisting of an Orbitrap Velos Pro Mass Spectrometer (Thermo Scientific) and a Dionex Ultimate-3000 nano-UPLC system (Thermo Scientific, Waltham, MA). Peptides were separated on an Acclaim PepMap 100 (C18, 5 μm, 100 Å, 100 μm×2 cm) trap column and an Acclaim PepMap RSLC (C18, 2 μm, 100 Å, 75 μm×50 cm) analytical column employing a linear gradient consisting of water with 0.1% formic acid (A) and acetonitrile with 0.1% formic acid (B) where the gradient was from 5% B at 0 min to 40% B at 105 min. MS spectra were acquired by data dependent scans consisting of MS/MS scans of the ten most intense ions from the full MS scan with dynamic exclusion option, which was 30 seconds. To identify proteins, spectra were searched against the UniProt human protein FASTA database (20,258 annotated entries, February 2018), using the Sequest HT search engine with the Proteome Discoverer v2.2 (Thermo Scientific). Search parameters were as follows: FT-trap instrument; parent mass error tolerance, 10 ppm; fragment mass error tolerance, 0.6 Da (monoisotopic); enzyme, trypsin (full); number maximum missed cleavages, 2; variable modifications, +15.995 Da (oxidation) on methionine; static modification, +57.021 Da (carbamidomethyl) on cysteine.

Bacterial ethanolamine metabolization screening. Twenty-five human origin probiotic strains were screened for their ethanolamine metabolizing capabilities. Bacterial streaks were grown for 48 hrs. in the MRS agar media plates containing 10 mM ethanolamine. Then plates were overlaid with 5 ml 500 mM ethanolamine MRS agar and incubated at 37° C. for 1 hr., followed by adding 5 ml of 2,4-dinitrophenylhydrazine in each plate and further incubate for 3 mins. Then the solution was discarded, and 5 ml of 5 M potassium hydroxide was added. Pink to purple zones were developed around the bacterial streaks, demonstrating the conversion of ethanolamine to acetaldehyde was quantified.

Ethanolamine operon quantification. Genomic DNA was extracted from feces and bacterial cells, using the Qiagen DNA Stool Mini Kit. After normalizing equal amount of DNA, the qRT-PCR analyses were performed, using powerUp SYBR Green master mix and ethanolamine metabolizing operon genes. The gene expression was calculated by using MET method while normalized with 16S rRNA as internal control.

Statistical Analyses. Different datasets were analyzed by student's T-test and one-two ANOVA, as appropriate. Alpha-diversity indices and bacterial abundance between the two groups were compared, using unpaired two-tailed Student's t-test. LEfSE (Linear discriminatory analysis [LDA] Effect Size) was used to identify unique bacterial taxa. Differences in beta-diversity were tested by permutational multivariate analysis of variance (PERMANOVA), a permutation-based multivariate analysis of variance to a matrix of pairwise distance to partition the inter-group and intra-group distance. Hierarchical clustering and heat-maps based on average linkage on Euclidean distance, depicting the patterns of abundance and log values were constructed within R v6.0, using the 'heatmap.2', pheatmap and "ggplots" packages.

Random forest analysis (RFA) and principal component analysis (PCA) were analyzed in R programming v6.0 using packages "randomForest", "ggplot2", "caret", "psych", "ggbiplots", "nnet" and "devtools". PCA was applied using all features of the NMR spectra with PLS-tool box (Eigenvector Research, Inc.) in Matlab (MathWorks). Welch t-test was applied for statistical significance analysis for metabolites in Amix 3.9 (Bruker Biospin) and a false discovery rate (FDR) were applied to control the family wised error. The heatmaps, Volcano Plot, Pathway analysis for pathways, and dendrogram were carried out in MetaboAnalyst 3.0. Unless otherwise stated, all the values presented herein are means ±SEM. $P<0.05$ was considered statistically significant.

Other advantages which are obvious, and which are inherent to the invention, will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods and compositions of the appended claims are not limited in scope by the specific methods and compositions described herein, which are intended as illustrations of a few aspects of the claims and any methods and compositions that are functionally equivalent are intended to fall within the scope of the claims. Various modifications of the methods and compositions in addition to those shown and described herein are intended to fall within the scope of the claims. Various modifications of the methods and compositions in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method of treating increased gut permeability, comprising administering a therapeutically effective amount of *Lactobacillus rhamnosus* strain HL-200 to a mammalian patient with ethanolamine-induced leaky gut;
    wherein *Lactobacillus rhamnosus* strain HL-200 metabolizes ethanolamine.

2. The method of claim 1, wherein the patient has diabetes.

3. The method of claim 2, wherein the diabetes is Type 2 diabetes.

4. The method of claim 1, wherein the therapeutically effective amount of *L. rhamnosus* strain HL-200 is administered to the patient orally.

5. The method of claim 4, wherein the therapeutically effective amount of *L. rhamnosus* strain HL-200 is in a tablet, troche, pill, or capsule.

6. The method of claim 4, wherein the therapeutically effective amount of *L. rhamnosus* strain HL-200 is in a solution, suspension, or emulsion.

7. The method of claim 6, wherein the suspension is a bacterial suspension.

8. The method of claim 1, wherein the therapeutically effective amount of *L. rhamnosus* strain HL-200 comprises a pharmaceutical or nonpharmaceutical formulation comprising a combination of *L. rhamnosus* strain HL-200 and a pharmaceutically acceptable carrier.

9. The method of claim 8, wherein the pharmaceutically acceptable carrier comprises a binder, excipient, disintegrating agent, sweetening agent, lubricant, flavoring agent, inert diluent, assimilable edible carrier, or any combination thereof.

10. The method of claim 1, further comprising administering one or more additional compounds chosen from probiotics, prebiotics, postbiotics, milk proteins, plant proteins, fibers, vitamins, herbs, minerals, or amino acids.

11. The method of claim 5, wherein the therapeutically effective amount of *L. rhamnosus* strain HL-200 is from $10^5$ to $10^{12}$ CFU in the pill.

12. The method of claim 1, wherein the therapeutically effective amount of *L. rhamnosus* strain HL-200 is from $10^5$ to $10^{12}$ CFU per day.

13. The method of claim 1, wherein the therapeutically effective amount of *L. rhamnosus* strain HL-200 is from $10^5$ to $10^{12}$ CFU/kg.

* * * * *